(12) United States Patent
Furuya

(10) Patent No.: US 10,752,625 B2
(45) Date of Patent: *Aug. 25, 2020

(54) METHOD OF MAKING TETRAHYDRONAPHTHYRIDINYL NONANOIC ACID COMPOUNDS

(71) Applicant: SciFluor Life Sciences, Inc., Cambridge, MA (US)

(72) Inventor: Takeru Furuya, Cambridge, MA (US)

(73) Assignee: SciFluor Life Sciences, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/288,309

(22) Filed: Feb. 28, 2019

(65) Prior Publication Data

US 2019/0194195 A1 Jun. 27, 2019

Related U.S. Application Data

(63) Continuation of application No. 15/941,604, filed on Mar. 30, 2018, now Pat. No. 10,253,025.

(60) Provisional application No. 62/518,705, filed on Jun. 13, 2017, provisional application No. 62/479,075, filed on Mar. 30, 2017.

(51) Int. Cl.
*C07D 471/04* (2006.01)
*C07D 401/06* (2006.01)

(52) U.S. Cl.
CPC ......... *C07D 471/04* (2013.01); *C07D 401/06* (2013.01)

(58) Field of Classification Search
CPC .............................. C07D 471/04; C07D 403/14
USPC .......................................... 546/122; 544/333
See application file for complete search history.

(56) References Cited

U.S. PATENT DOCUMENTS

| | | | |
|---|---|---|---|
| 9,518,053 B2 | 12/2016 | Askew et al. | |
| 9,717,729 B2 | 8/2017 | Askew et al. | |
| 9,790,222 B2 | 10/2017 | Askew et al. | |
| 10,253,025 B2 | 4/2019 | Furuya | |
| 2016/0075698 A1 | 3/2016 | Askew et al. | |

FOREIGN PATENT DOCUMENTS

| | | |
|---|---|---|
| WO | WO 2014/124302 A1 | 8/2014 |
| WO | WO 2016/134223 A2 | 8/2016 |

OTHER PUBLICATIONS

Christiansen Michael A. et al. "BOTPPI, a new Wittig salt for the synthesis of 12-(S)-hydroxy-eicosatetraenoic acid", Tetrahedron Letters, vol. 4806, 53, No. 36, 2012, p. 4805-4808.

Coleman P. et al. "Nonpeptide [alpha]v[beta]3 antagonists. Part 11: Discovery and preclinical evaluation of potent [alpha]v[beta] 3 antagonists for the prevention and treatment of osteoporosis", Journal of Medicinal Chemistry, vol. 47, No. 20, 2004, p. 4829-4837.

Tanaka N. et al. "[2-(omega-Phenylalkyl)phenoxy]alkylamines Synthesis and Dual Dopamine2 (D2) and 5-Hydroxytryptamine2 (5-HT2) Receptor Antagonistic Activities", Chemical and Pharmaceutical Bulletin, vol. 46, No. 4, 1998, p. 639-646.

Taylor S. et al. "Competitive intramolecular cyclizations of epoxides to aromatic and double bond positions", The Journal of Organic Chemistry, vol. 55, No. 13, 1990, p. 4202-4207.

*Primary Examiner* — Charanjit Aulakh
(74) *Attorney, Agent, or Firm* — Cooley LLP; Heidi A. Erlacher; Chen Chen

(57) ABSTRACT

The present application relates to methods of preparing a compound of formula I:

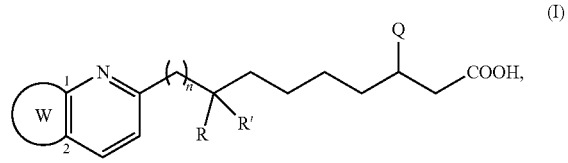

(I)

or a pharmaceutically acceptable salt or solvate thereof.

18 Claims, 2 Drawing Sheets

METHOD OF MAKING TETRAHYDRONAPHTHYRIDINYL NONANOIC ACID COMPOUNDS

RELATED APPLICATIONS

This application is a continuation of U.S. application Ser. No. 15/941,604, filed Mar. 30, 2018 (now allowed), which claims the benefit of and priority to U.S. Provisional Application No. 62/518,705, filed Jun. 13, 2017, and U.S. Provisional Application No. 62/479,075, filed Mar. 30, 2017, the contents of each of which are incorporated herein by reference in their entireties.

BACKGROUND

Fibrosis is characterized by excessive accumulation of collagen in the extracellular matrix of the involved tissue. It is a long-standing and challenging clinical problem for which no effective treatment is currently available. The production of collagen is a highly regulated physiological process, the disturbance of which may lead to the development of tissue fibrosis. The formation of fibrous tissue is part of the normal beneficial process of healing after injury. In some cases, however, abnormal accumulation of fibrous material can severely interfere with the normal function of the affected tissue or even cause loss of function of the affected organ. A variety of compounds have been identified as anti-fibrosis agents via different mechanisms of action, including the suppression of collagen expression.

Age-related macular degeneration (AMD) is the leading cause of blindness in people over 55; and diabetic retinopathy (DR) is the leading cause in people under 55. Both diseases are characterized by new blood vessel growth. Macular edema and Diabetic macular edema (DME) occur when fluid and protein deposits collect on or under the macula caused by leaking macular capillaries. Thrombosis of central retinal vein (CRV) and its branches is the second most prevalent vascular pathology after DR, and results in abrupt decrease in visual acuity and is accompanied by macular edema. Thus, anti-angiogenesis treatments are useful in combating all these conditions.

Integrins are heterodimeric transmembrane proteins through which cells attach and communicate with extracellular matrices and other cells. αv integrins are key receptors involved in mediating cell migration and angiogenesis. αv integrins have been shown to be involved in a number of diseases and conditions including ocular angiogenesis and fibrosis of organs. Expression of αv integrins is upregulated in various diseases or conditions, such as AMD and DR, and in mouse model of oxygen-induced retinopathy (OIR) or retinopathy of prematurity (ROP) model. Also, αvβ3 is expressed in new vessels after photocoagulation, but not in normal choroidal vessels, in the laser-induced choroidal neovascularization model for AMD. Administration of αv integrin antagonists (e.g., a cyclic RGD peptide) has been shown to inhibit retinal and choroidal neovascularization. Angiogenesis inhibitors targeting vascular endothelial growth factor (VEGF), other growth factors (e.g., fibroblast growth factor (FGF), platelet-derived growth factor (PDGF)), chemokines (e.g., IL8, SDF1, G-CSF), receptors (e.g., CXCR1, FGF-R, P1GFR, PDGFR, Tie-receptors), intracellular mediators (e.g., c-kit kinase, PI3 kinase, PKC), and extracellular mediators (e.g., integrins, cadherins), as well as inhibitors of pro-angiogenic targets (e.g., phosphoinositide 3 kinase), have been investigated for the treatment of AMD and DR. However, application of these drugs is limited.

Thus, there continues to be a need for compounds, compositions, and methods for treating fibrosis, AMD, DR, DME, and macular edema following retinal vein occlusion, that are safe, effective, and conveniently administered. The present application addresses the need.

SUMMARY

The present application relates to a method of making a compound of formula I:

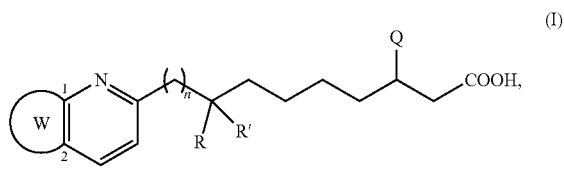

or a pharmaceutically acceptable salt or solvate thereof, comprising:

Step 1: reacting Compound A:

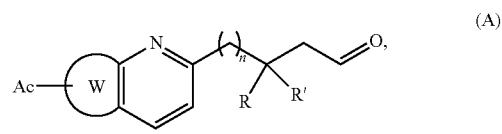

wherein "Ac" refers to an acetyl group and is a substituent on W, with Compound B:

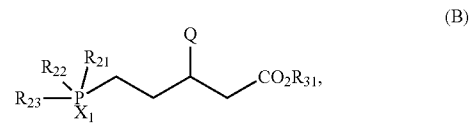

wherein $X_1$ is halogen, and $R_{21}$, $R_{22}$, $R_{23}$, and $R_{31}$ are each independently selected from the group consisting of optionally substituted alkyl, optionally substituted alkenyl, optionally substituted alkynyl, and optionally substituted aryl, to form Compound 1:

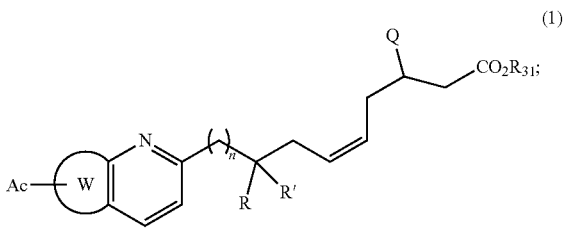

and

Step 2: reducing Compound 1:

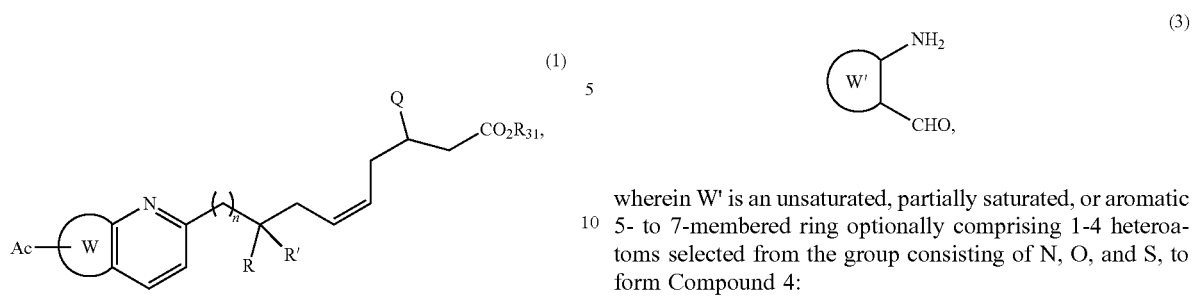

optionally in the presence of a catalyst, to form the compound of formula I: wherein:

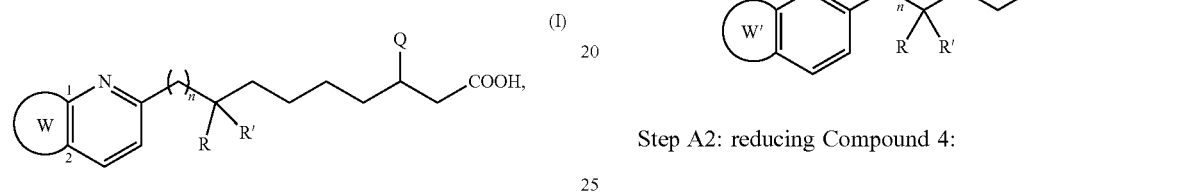

Q is

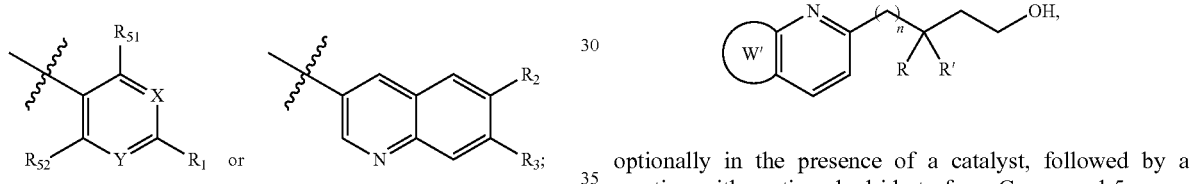

X is $CR_4$ or N;
Y is $CR_4$ or N;
$R_1$ is H, F, Cl, $C_1$-$C_4$ alkyl substituted with 1, 2, 3, 4, 5, 6, 7, 8, or 9 fluorine atoms, or $C_1$-$C_4$ alkoxy substituted with 0, 1, 2, 3, 4, 5, 6, or 7 fluorine atoms;
$R_2$ and $R_3$ are each independently H, F, $CH_2F$, $CHF_2$, or $CF_3$, provided that one of $R_2$ and $R_3$ is not H;
each $R_4$ is independently H, $CH_2F$, $CHF_2$, or $CF_3$; and
$R_{51}$ and $R_{52}$ are each independently H, F, or Cl;
W is fused to the pyridyl moiety at positions 1 and 2, and W is a 5- to 7-membered ring optionally comprising 1-4 heteroatoms selected from the group consisting of N, O, and S;
n is 1 or 2; and
R and R' are each independently H or F, or R and R', together with the carbon atom to which they are attached, form a 3- or 4-membered carbocyclic or heterocyclic ring.

In some embodiments, the method further comprises one or more steps selected from:

Step A1: reacting Compound 2: with Compound 3:

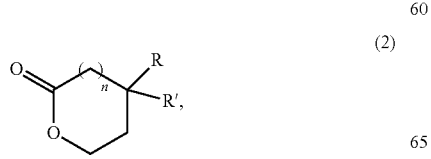

wherein W' is an unsaturated, partially saturated, or aromatic 5- to 7-membered ring optionally comprising 1-4 heteroatoms selected from the group consisting of N, O, and S, to form Compound 4:

(4)

Step A2: reducing Compound 4:

(4)

optionally in the presence of a catalyst, followed by a reaction with acetic anhydride to form Compound 5:

(5)

and

Step A3: converting Compound 5:

(5)

to Compound A:

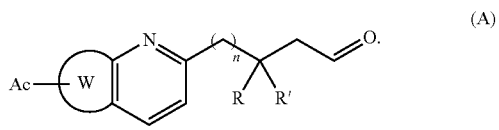

In some embodiments, the method comprises one or more steps selected from:

Step B1: reacting Compound 6a:

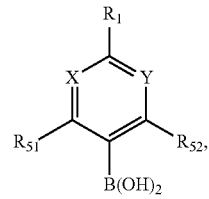
(6a)

with Compound 7:

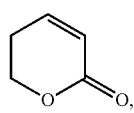
(7)

to form Compound 8a:

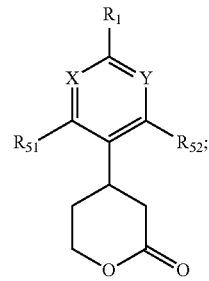
(8a)

Step B2: converting Compound 8a:

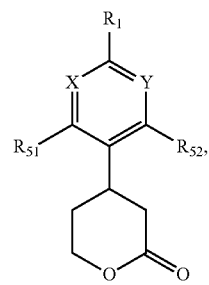
(8a)

to Compound 9a:

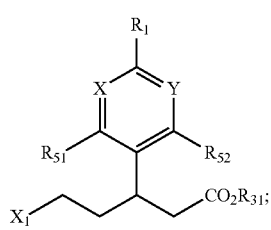
(9a)

Step B3: reacting Compound 9a:

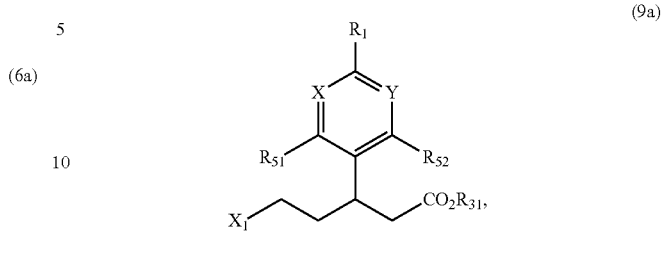
(9a)

with a phosphine compound

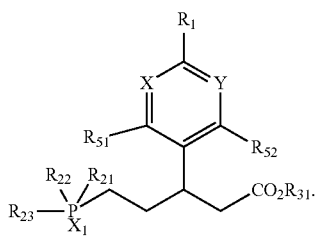
(7)

to form Compound B1:

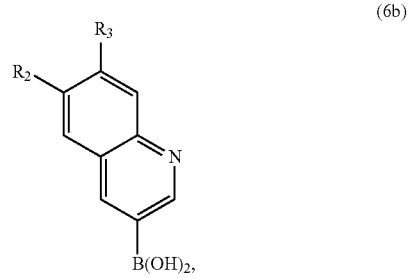
(B1)

In some embodiments, the method further comprises one or more steps selected from:

Step C1: reacting Compound 6b:

(6b)

with Compound 7:

(7)

to form Compound 8b:

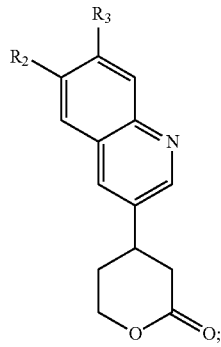

Step C2: converting Compound 8b:

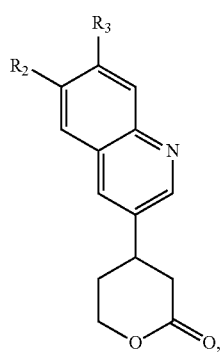

to Compound 9b:

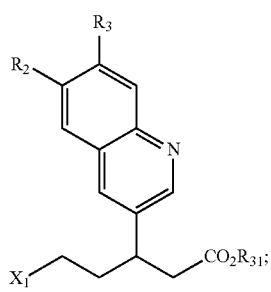

Step C3: reacting Compound 9b:

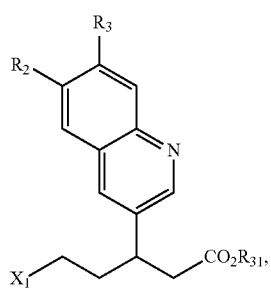

with a phosphine compound

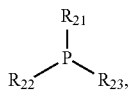

to form Compound B2:

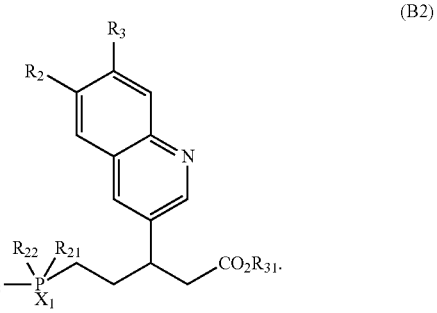

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present application, suitable methods and materials are described below. All publications, patent applications, patents, and other references mentioned herein are incorporated by reference. The references cited herein are not admitted to be prior art to the present application. In the case of conflict, the present specification, including definitions, will control. In addition, the materials, methods, and examples are illustrative only and are not intended to be limiting.

Other features and advantages of the disclosure will be apparent from the following detailed description and claims.

DETAILED DESCRIPTION

Methods of the Present Disclosure

Figure 1:
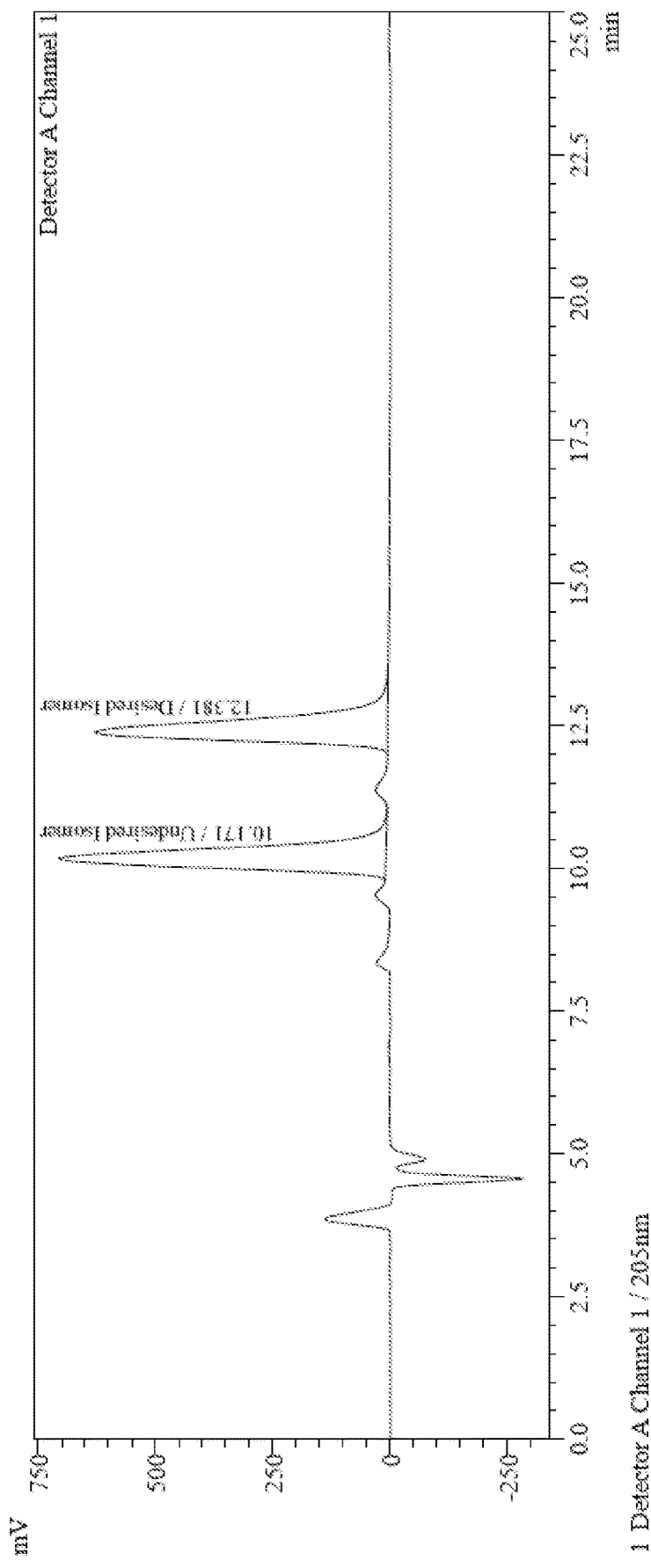
FIG. 1 sets forth a chromatogram of racemic 9-(5,6,7,8-tetrahydro-1,8-naphthyridin-2-yl)-3-(3-(trifluoromethyl) phenyl)nonanoic acid prepared by the methods of the present disclosure.
Figure 2:
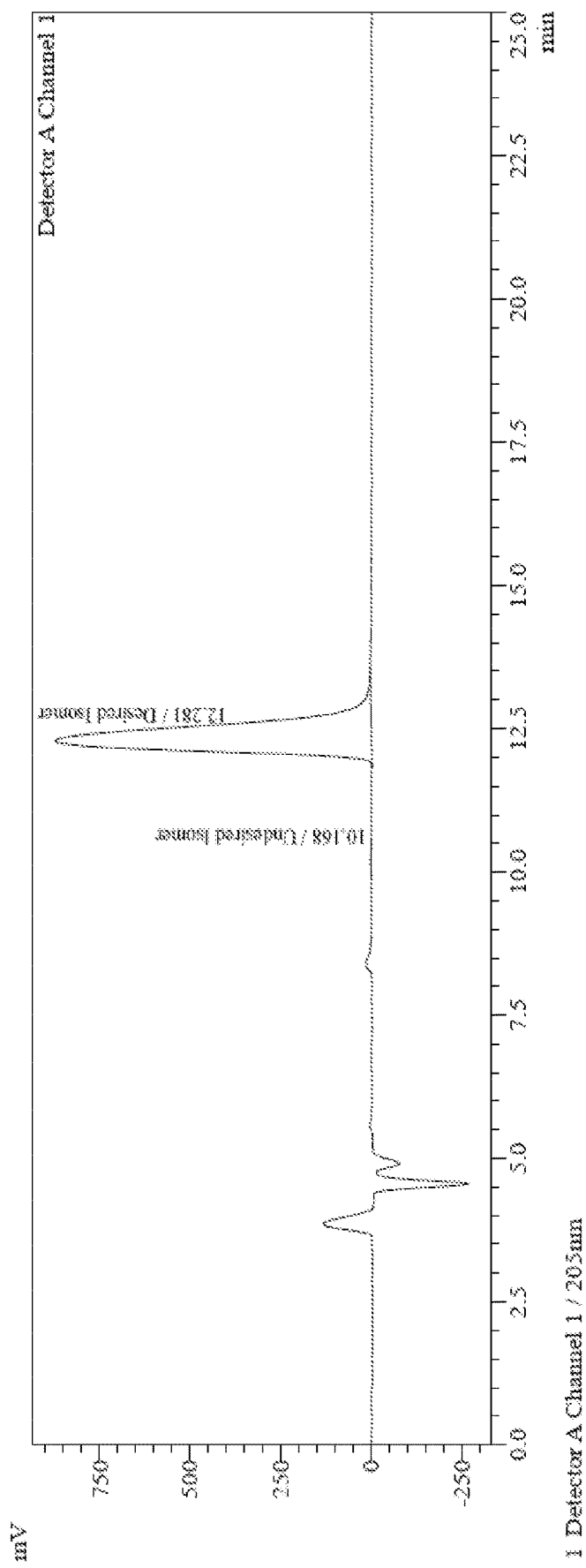
FIG. 2 sets forth a chromatogram of (S)-9-(5,6,7,8-tetrahydro-1,8-naphthyridin-2-yl)-3-(3-(trifluoromethyl)phenyl) nonanoic acid 2-amino-iso-butanol salt prepared by the methods of the present disclosure.

In one aspect, the present disclosure provides a method of making a compound of formula I:

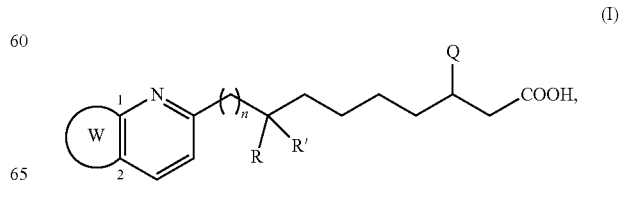

or a pharmaceutically acceptable salt or solvate thereof, comprising:

Step 1: reacting Compound A:

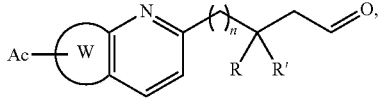
(A)

wherein "Ac" refers to an acetyl group and is a substituent on W, with Compound B:

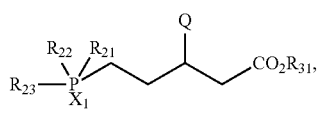
(B)

wherein $X_1$ is halogen, and $R_{21}$, $R_{22}$, $R_{23}$, and $R_{31}$ are each independently selected from the group consisting of optionally substituted alkyl, optionally substituted alkenyl, optionally substituted alkynyl, and optionally substituted aryl, to form Compound 1:

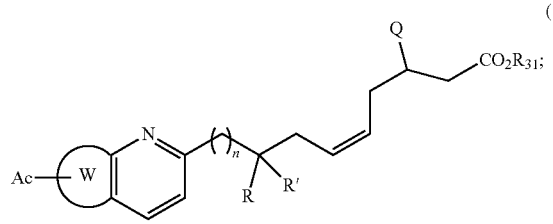
(1)

and

Step 2: reducing Compound 1:

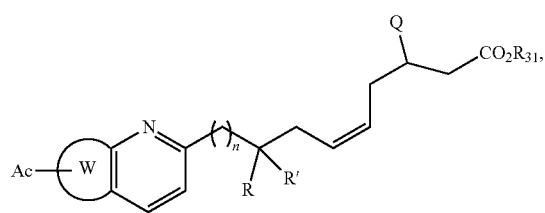
(1)

optionally in the presence of a catalyst, to form the compound of formula I:

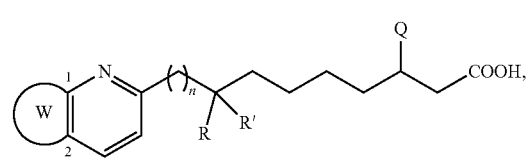
(I)

wherein:
Q is

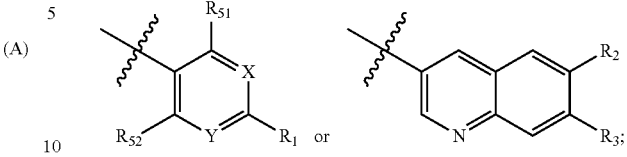

X is $CR_4$ or N;
Y is $CR_4$ or N;
$R_1$ is H, F, Cl, $C_1$-$C_4$ alkyl substituted with 1, 2, 3, 4, 5, 6, 7, 8, or 9 fluorine atoms, or $C_1$-$C_4$ alkoxy substituted with 0, 1, 2, 3, 4, 5, 6, or 7 fluorine atoms;
$R_2$ and $R_3$ are each independently H, F, $CH_2F$, $CHF_2$, or $CF_3$, provided that one of $R_2$ and $R_3$ is not H;
each $R_4$ is independently H, $CH_2F$, $CHF_2$, or $CF_3$; and
$R_{51}$ and $R_{52}$ are each independently H, F, or Cl;
W is fused to the pyridyl moiety at positions 1 and 2, and W is a 5- to 7-membered ring optionally comprising 1-4 heteroatoms selected from the group consisting of N, O, and S;
n is 1 or 2; and
R and R' are each independently H or F, or R and R', together with the carbon atom to which they are attached, form a 3- or 4-membered carbocyclic or heterocyclic ring.

In some embodiments, the compound of formula I comprises at least one fluorine atom.

In some embodiments, n is 1. In some embodiments, n is 2.

In some embodiments, R and R' are each H. In some embodiments, R and R' are each F. In another aspect, R is H and R' is F.

In some embodiments, R and R', together with the carbon atom to which they are attached, form a 3- or 4-membered carbocyclic or heterocyclic ring. In some embodiments, R and R', together with the carbon atom to which they are attached, form a 4-membered heterocyclic ring. In some embodiments, the 4-membered heterocyclic ring is an oxetane ring. For example, the oxetane ring is an oxetan-3-yl ring or oxetan-2-yl ring.

In some embodiments, Q is

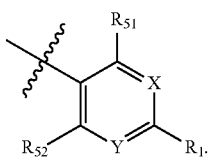

In some embodiments, X is N and Y is $CR_4$. In some embodiments, X and Y are each $CR_4$. In some embodiments, X and Y are each N. In some embodiments, at least one $R_4$ is H. In some embodiments, at least one $R_4$ is $CH_2F$, $CHF_2$, or $CF_3$. In some embodiments, at least one $R_4$ is $CF_3$.

In some embodiments, $R_1$ is H. In some embodiments, $R_1$ is F, Cl, $C_1$-$C_4$ alkyl substituted with 1, 2, 3, 4, 5, 6, 7, 8, or 9 fluorine atoms, or $C_1$-$C_4$ alkoxy substituted with 0, 1, 2, 3, 4, 5, 6, or 7 fluorine atoms. In some embodiments, $R_1$ is F or Cl. In some embodiments, $R_1$ is $C_1$-$C_4$ alkyl substituted with 1, 2, 3, 4, 5, 6, 7, 8, or 9 fluorine atoms, or $C_1$-$C_4$ alkoxy substituted with 0, 1, 2, 3, 4, 5, 6, or 7 fluorine atoms.

In some embodiments, $R_1$ is straight chain $C_1$-$C_4$ or branched $C_3$-$C_4$ alkyl, and is substituted with 1, 2, 3, 4, 5, 6, 7, 8, or 9 fluorine atoms. In some embodiments, $R_1$ is methyl, ethyl, propyl, or butyl, and is substituted with 1, 2, 3, 4, 5, 6, 7, 8, or 9 fluorine atoms. In some embodiments, $R_1$ is methyl substituted with 1, 2, or 3 fluorine atoms. In some embodiments, $R_1$ is $CF_3$. In some embodiments, X is N, Y is CH, and $R_1$ is $CF_3$.

In some embodiments, $R_1$ is straight chain $C_1$-$C_4$ or branched $C_3$-$C_4$ alkoxy, and is substituted with 0, 1, 2, 3, 4, 5, 6, or 7 fluorine atoms. In some embodiments, $R_1$ is methoxy, ethoxy, propoxy, or butoxy, and is substituted with 0, 1, 2, 3, 4, 5, 6, or 7 fluorine atoms. In some embodiments, $R_1$ is methoxy substituted with 0, 1, 2, or 3 fluorine atoms. In some embodiments, $R_1$ is $OCH_3$, $OCH_2F$, $OCHF_2$, or $OCF_3$. In some embodiments, $R_1$ is $OCHF_2$ or $OCF_3$. In some embodiments, X is N, Y is CH, and $R_1$ is $OCHF_2$ or $OCF_3$. In some embodiments, X and Y are each N, and $R_1$ is $OCHF_2$ or $OCF_3$.

In some embodiments, $R_{51}$ and $R_{52}$ are each H. In some embodiments, one of $R_{51}$ and $R_{52}$ is H, and the other is F or Cl. In some embodiments, one of $R_{51}$ and $R_{52}$ is H, and the other is F. In some embodiments, $R_{51}$ and $R_{52}$ are each F or Cl.

In some embodiments, Q is

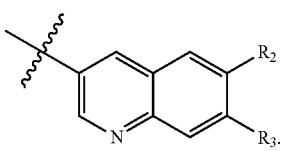

In some embodiments, $R_2$ is F. In some embodiments, $R_2$ is F and $R_3$ is H. In some embodiments, $R_2$ is $CH_2F$, $CHF_2$, or $CF_3$. In some embodiments, $R_2$ is $CF_3$. In some embodiments, $R_2$ is $CF_3$ and $R_3$ is H.

In some embodiments, $R_3$ is F. In some embodiments, $R_3$ is F and $R_2$ is H. In some embodiments, $R_3$ is $CH_2F$, $CHF_2$, or $CF_3$. In some embodiments, $R_3$ is $CF_3$. In some embodiments, $R_3$ is $CF_3$ and $R_2$ is H.

In some embodiments, $R_2$ and $R_3$ are each F.

In some embodiments,

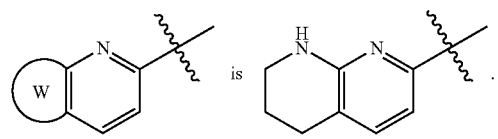

In some embodiments,

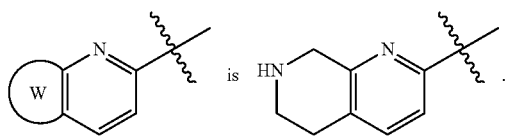

In some embodiments,

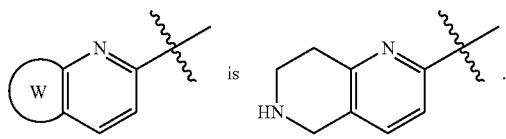

In some embodiments,

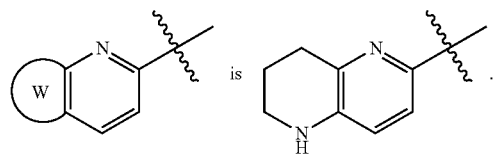

In some embodiments, the compound of formula I is an R isomer, wherein the chiral center is the carbon to which Q is attached. In some embodiments, the compound of formula I is an S isomer, wherein the chiral center is the carbon to which Q is attached.

In some embodiments, the compound of formula I is selected from the group consisting of:

(A1)

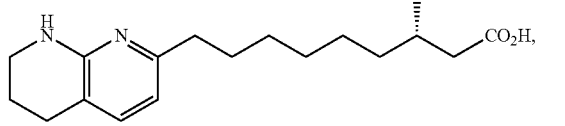

(A2)

(A3)

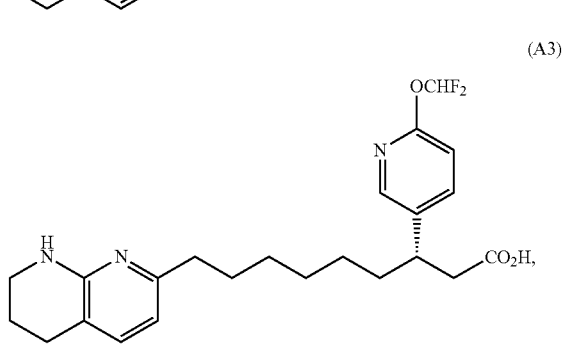

(A4)
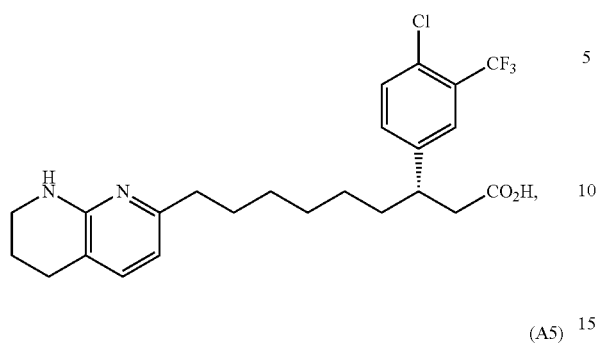
(A5)
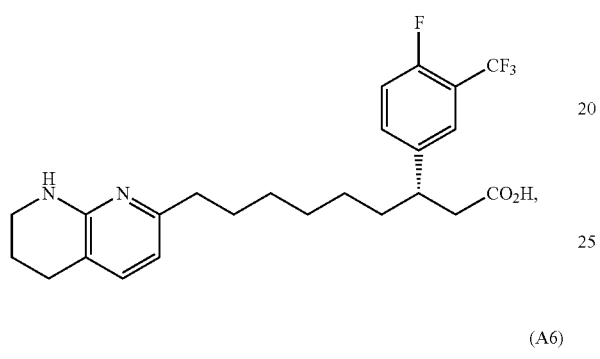
(A6)
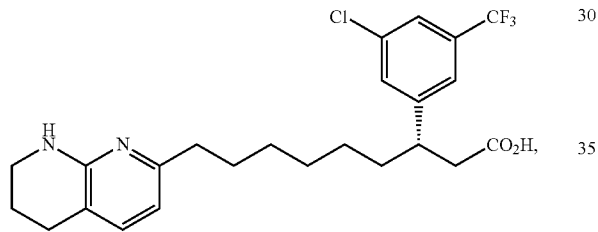
(A7)
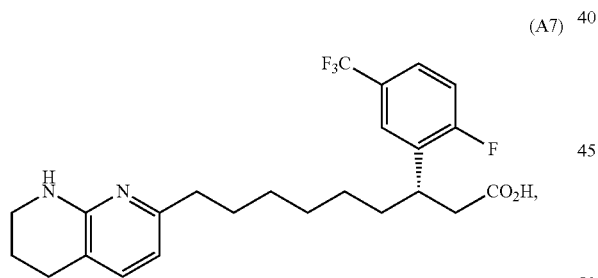
(A8)
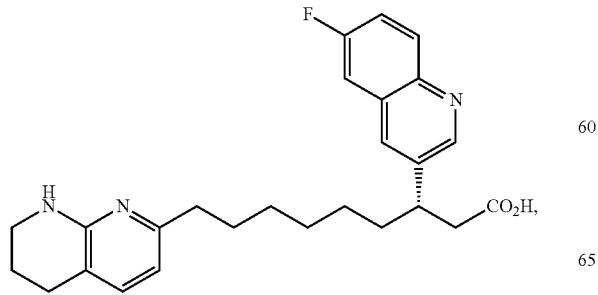
(A9)
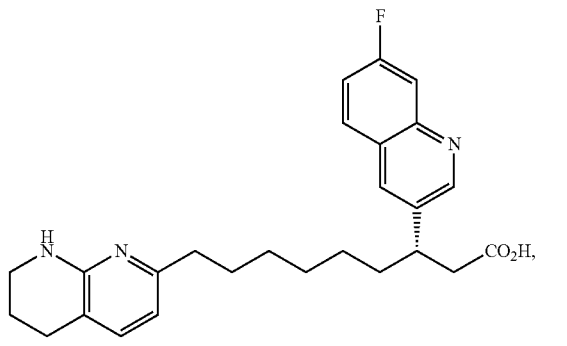
(A10)
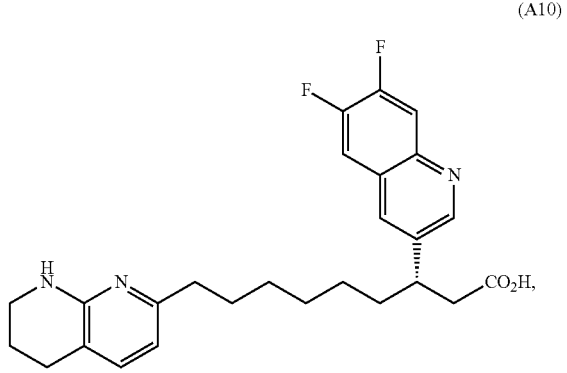
(A11)
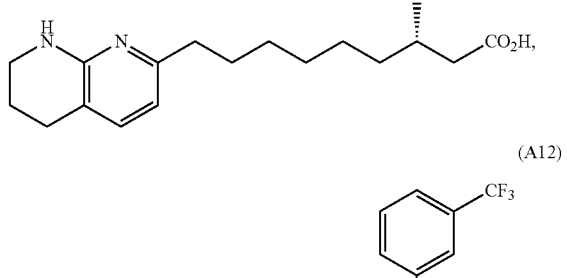
(A12)
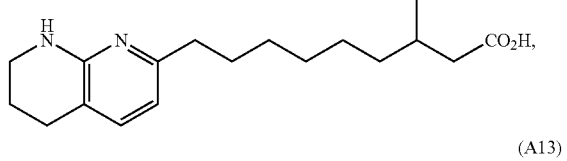
(A13)
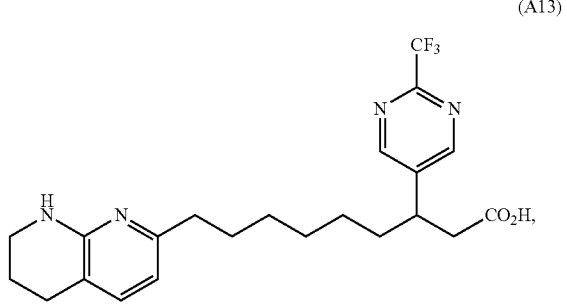

-continued (A14)
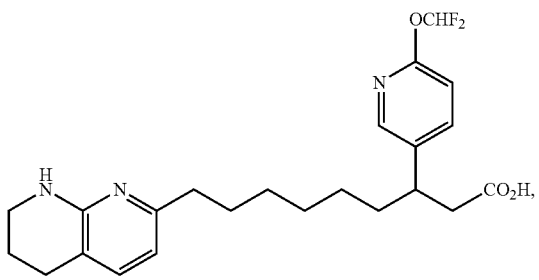

(A15)
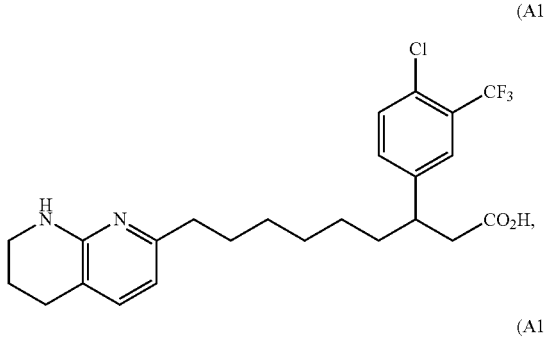

(A16)
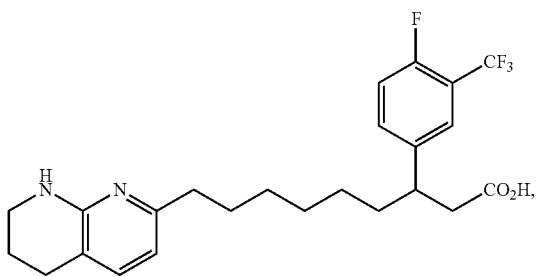

(A17)
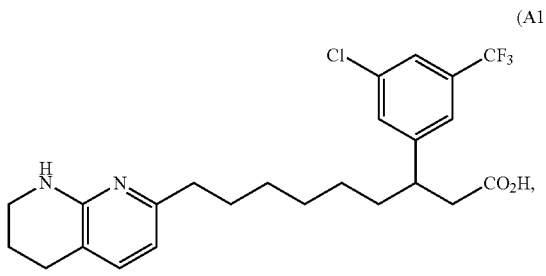

(A18)
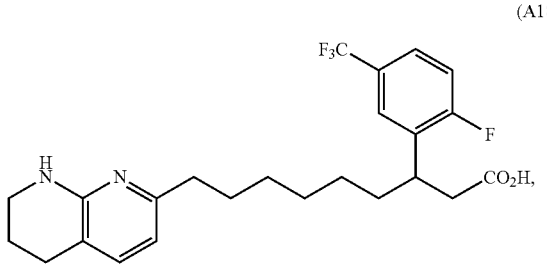

(A19)
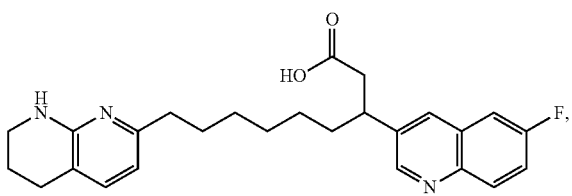

-continued (A20)
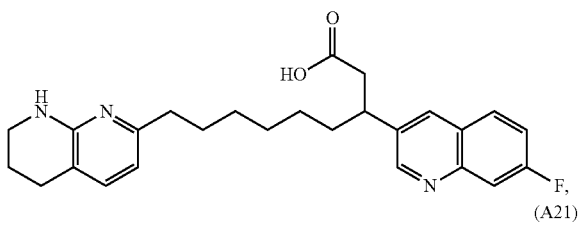

(A21)
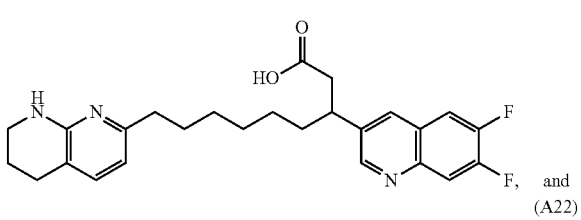
and (A22)
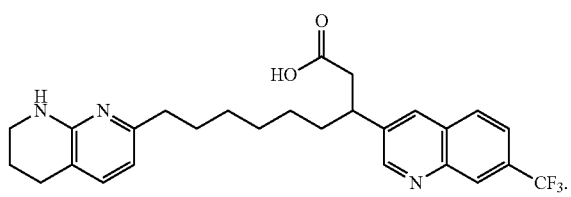

In some embodiments, Step 1 comprises adding a non-nucleophilic base to Compound B. In some embodiments, the non-nucleophilic base is added to Compound B in the presence of an aprotic solvent. In some embodiments, the aprotic solvent is tetrahydrofuran ("THF"). In some embodiments, Step 1 further comprises reacting Compound B with the non-nucleophilic base. In some embodiments, the non-nucleophilic base is potassium bis(trimethylsilyl)amide ("KHMDS") or sodium bis(trimethylsilyl)amide ("NaHMDS"). In some embodiments, the non-nucleophilic base is KHMDS.

In some embodiments, Step 1 comprises reacting the non-nucleophilic base with Compound B at a temperature below 0° C., e.g., about −10° C., about −20° C., about −30° C., about −40° C., about −50° C., about −60° C., about −70° C., about −80° C., about −90° C., or about −100° C. In some embodiments, the non-nucleophilic base is reacted with Compound B for less than 2 hours, less than 90 minutes, less than 60 minutes, less than 50 minutes, less than 40 minutes, less than 30 minutes, or less than 20 minutes. In some embodiments, the non-nucleophilic base is reacted with Compound B for about 30 minutes, about 20 minutes, about 15 minutes, or about 10 minutes. Specifically, the reaction of the non-nucleophilic base with Compound B produces a ylide.

In some embodiments, Step 1 further comprises adding Compound A to the reaction mixture comprising Compound B and the non-nucleophilic base. In some embodiments, Step 1 comprises reacting Compound A with the reaction mixture comprising Compound B and the non-nucleophilic base at a temperature below 0° C., e.g., about −10° C., about −20° C., about −30° C., about −40° C., about −50° C., about −60° C., about −70° C., about −80° C., about −90° C., or about −100° C. In some embodiments, Compound A is reacted with the reaction mixture comprising Compound B and the non-nucleophilic base for less than 2 hours, less than 90 minutes, less than 60 minutes, less than 50 minutes, less than 40 minutes, less than 30 minutes, or less than 20 minutes. In some embodiments, Compound A is reacted with the reaction mixture comprising Compound B and the non-nucleophilic base for about 30 minutes, about 20 minutes, about 15 minutes, or about 10 minutes.

In some embodiments, Step 1 further comprises raising the temperature of the reaction between Compound A and the mixture comprising Compound B and the non-nucleophilic base to a temperature above 0° C., e.g., about 5° C., about 10° C., about 15° C., about 20° C., about 25° C., or about 30° C. In some embodiments, Step 1 further comprises one or more steps to extract and/or purify Compound 1 from the final reaction mixture.

In some embodiments, Step 2 comprises reacting Compound 1 with a hydrogen source, optionally in the presence of a catalyst. The catalyst can be added to Compound 1 prior to, concurrently, or after the addition of the hydrogen source. Examples of hydrogen sources include, but are not limited to, H$_2$, hydrazine, dihydronaphthalene, dihydroanthracene, isopropanol, and formic acid. The catalyst can be a homogeneous catalyst or a heterogeneous catalyst. Examples of catalysts include, but are not limited to, platinum, palladium, rhodium, ruthenium, nickel, gold, and a combination thereof. The catalyst can be an organometallic compound in which a metal (e.g., platinum, palladium, rhodium, ruthenium, nickel, or gold) is complexed with one or more organic ligands. In some embodiments, the catalyst is selected from Pd(OH)$_2$/C, Pd(OAc)$_2$, PdCl$_2$(tBu$_2$PhP)$_2$[dichlorobis(di-tert-butylphenylphosphine palladium (II)], and PdCl$_2$(DPEPhos)[bis(diphenylphosphinophenyl)ether palladium (II) chloride].

In some embodiments, the hydrogen source is H$_2$. Accordingly, Step 2 comprises adding H$_2$ to Compound 1 in the presence of a protic solvent. In some embodiments, the protic solvent is an alcohol selected from methanol, ethanol, isopropanol, butanol, and t-butanol. In some embodiments, the protic solvent is methanol. In some embodiments, the catalyst includes palladium, such as palladium on barium sulfate and palladium on carbon. In some embodiments, the catalyst is Pd(OH)$_2$/C. In some embodiments, the catalyst is PdCl$_2$/C. In some embodiments, H$_2$ is reacted with Compound 1 at a temperature above 0° C., e.g., about 5° C., about 10° C., about 15° C., about 20° C., about 25° C., or about 30° C. In some embodiments, H$_2$ is reacted with Compound 1 for about 1-24 hours, about 5-20 hours, or about 10-15 hours. In some embodiments, H$_2$ is reacted with Compound 1 for about 5 hours, about 8 hours, about 10 hours, about 12 hours, or about 14 hours.

In some embodiments, Step 2 further comprises adding a base to the reaction of H$_2$ and Compound 1, followed by the addition of an acid after stirring for a period of time (e.g., about 1 hour, about 1.5 hours, about 2 hours, about 2.5 hours, about 3 hours, about 3.5 hours, or about 4 hours). In some embodiments, the base is KOH, NaOH, or a combination thereof. In some embodiments, the base is NaOH. In some embodiments, the acid is HNO$_3$, HCl, H$_2$SO$_4$, or a combination thereof. In some embodiments, the acid is HCl. In some embodiments, Step 2 further comprises one or more steps to extract and/or purify the compound of formula I from the reaction mixture.

In some embodiments, the method further comprises one or more steps of making Compound A. In some embodiment, the method of making Compound A comprises the following step:

Step A1: reacting Compound 2:

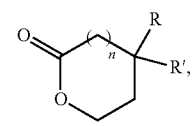

(2)

with Compound 3:

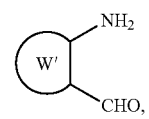

(3)

wherein W' is an unsaturated, partially saturated, or aromatic 5- to 7-membered ring optionally comprising 1-4 heteroatoms selected from the group consisting of N, O, and S, to form Compound 4:

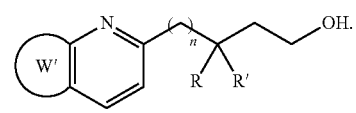

(4)

In some embodiments, Step A1 comprises adding n-butyllithium to dimethyl methylphosphonate to generate a mixture. In some embodiments, n-butyllithium is added to dimethyl methylphosphonate in the presence of an aprotic solvent. In some embodiments, the aprotic solvent is THF. In some embodiments, n-butyllithium is added to dimethyl methylphosphonate at a temperature below 0° C., e.g., about −10° C., about −20° C., about −30° C., about −40° C., about −50° C., about −60° C., about −70° C., about −80° C., about −90° C., or about −100° C. In some embodiments, the reaction of n-butyllithium with dimethyl methylphosphonate produces a carbanion.

In some embodiments, Step A1 comprises adding Compound 2 to the mixture of n-butyllithium and dimethyl methylphosphonate, optionally followed by the addition of NH$_4$Cl. In some embodiments, Step A1 comprises separating an organic phase from the reaction mixture. In some embodiments, Step A1 comprises removing excess dimethyl methylphosphonate from the organic phase to afford crude β-ketophosphonate. In some embodiments, Step A1 comprises adding Compound 3 to the crude β-ketophosphonate. In some embodiments, Compound 3 is added to the crude β-ketophosphonate in the presence of a protic solvent, optionally at a temperature above 0° C., e.g., about 5° C., about 10° C., about 15° C., about 20° C., about 25° C., or about 30° C. In some embodiments, the protic solvent is an alcohol selected from methanol, ethanol, isopropanol, butanol, and t-butanol. In some embodiments, the protic solvent is methanol. In some embodiments, Step A1 comprises adding a base to the crude β-ketophosphonate. In some embodiments, the base is NaOH, KOH, or a combination thereof. In some embodiments, the base is NaOH. In some embodiments, Step A1 further comprises one or more steps to extract and/or purify Compound 4 from the reaction mixture.

In some embodiments, the method of making Compound A comprises the following step:

Step A2: reducing Compound 4:

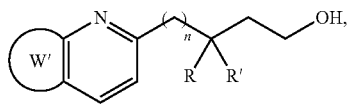
(4)

optionally in the presence of a catalyst, followed by a reaction with acetic anhydride to form Compound 5:

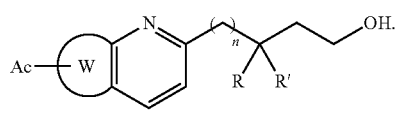
(5)

In some embodiments, Step A2 comprises reacting Compound 4 with a hydrogen source, optionally in the presence of a catalyst. The catalyst can be added to Compound 4 prior to, concurrently, or after the addition of the hydrogen source. Examples of hydrogen sources include, but are not limited to, $H_2$, hydrazine, dihydronaphthalene, dihydroanthracene, isopropanol, and formic acid. The catalyst can be a homogeneous catalyst or a heterogeneous catalyst. Examples of catalysts include, but are not limited to, platinum, palladium, rhodium, ruthenium, nickel, gold, and a combination thereof. The catalyst can be an organometallic compound in which a metal (e.g., platinum, palladium, rhodium, ruthenium, nickel, or gold) is complexed with one or more organic ligands. In some embodiments, the catalyst is selected from $Pd(OH)_2/C$, $Pd(OAc)_2$, $PdCl_2(tBu_2PhP)_2$[dichlorobis(di-tert-butylphenylphosphine palladium (II)], and $PdCl_2$(DPEPhos)[bis(diphenylphosphinophenyl)ether palladium (II) chloride].

In some embodiments, the hydrogen source is $H_2$. Accordingly, Step A2 comprises adding $H_2$ to Compound 4 in the presence of a protic solvent. In some embodiments, the protic solvent is an alcohol selected from methanol, ethanol, isopropanol, butanol, and t-butanol. In some embodiments, the protic solvent is methanol. In some embodiments, the catalyst includes palladium, such as palladium on barium sulfate and palladium on carbon. In some embodiments, the catalyst is $Pd(OH)_2/C$. In some embodiments, the catalyst is $PdCl_2/C$.

In some embodiments, $H_2$ is reacted with Compound 4 at a temperature above 0° C., e.g., about 5° C., about 10° C., about 15° C., about 20° C., about 25° C., or about 30° C. In some embodiments, $H_2$ is reacted with Compound 4 for about 1-24 hours, about 5-20 hours, or about 10-18 hours. In some embodiments, $H_2$ is reacted with Compound 4 for about 5 hours, about 8 hours, about 10 hours, about 12 hours, about 14 hours, about 16 hours, about 18 hours, or about 20 hours. $H_2$ is reacted with Compound 4 to generate a reaction mixture, to which 4-(dimethylamino)pyridine ("DMAP") is added. In some embodiments, DMAP is added to the reaction mixture in the presence of pyridine and $Ac_2O$. In some embodiments, Step A2 further comprises adding potassium carbonate or sodium carbonate after the addition of DMAP, optionally in the presence of a protic solvent (e.g., methanol). In some embodiments, Step A2 further comprises adding $NH_4Cl$ after the addition of potassium carbonate or sodium carbonate. In some embodiments, Step A2 further comprises one or more steps to extract and/or purify Compound 5 from the reaction mixture.

In some embodiments, the method of making Compound A comprises the following step:

Step A3: converting Compound 5:

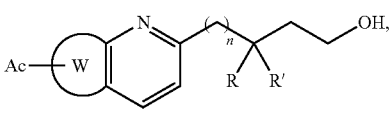
(5)

to Compound A:

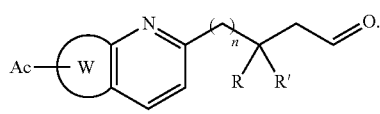
(A)

In some embodiments, Step A3 comprises adding, to Compound 5, a compound capable of transforming primary alcohols to aldehydes. Compounds capable of transforming primary alcohols to aldehydes include, but are not limited to, chromium-based reagents, such as Collins reagent ($CRO_3.Py2$), PDC or PCC; activated DMSO, resulting from reaction of DMSO with electrophiles, such as oxalyl chloride (Swern oxidation), a carbodiimide (Pfitzner-Moffatt oxidation) or the complex SO3.Py (Parikh-Doering oxidation); hypervalent iodine compounds, such as Dess-Martin periodinane or 2-Iodoxybenzoic acid; catalytic TPAP in presence of excess of NMO (Ley oxidation); and catalytic TEMPO in the presence of excess bleach (NaOCl) (Oxoammonium-catalyzed oxidation).

In some embodiments, the compound capable of transforming primary alcohols to aldehydes is Dess-Martin periodinane. In some embodiments, Dess-Martin periodinane is added to Compound 5 in the presence of an aprotic solvent. In some embodiments, the aprotic solvent is $CH_2Cl_2$. In some embodiments, Dess-Martin periodinane is reacted with Compound 5 at a temperature above 0° C., e.g., about 5° C., about 10° C., about 15° C., about 20° C., about 25° C., or about 30° C. In some embodiments, Dess-Martin periodinane is reacted with Compound 5 for about 1-10 hours. In some embodiments, Dess-Martin periodinane is reacted with Compound 5 for about 30 minutes, about 60 minutes, about 90 minutes, about 2 hours, about 2.5 hours, about 3 hours, about 3.5 hours, or about 4 hours. In some embodiments, Step A3 further comprises adding a base to the mixture comprising Dess-Martin periodinane and Compound 5. In some embodiments, Step A3 further comprises one or more steps to extract and/or purify Compound A from the reaction mixture.

In some embodiments, the method further comprises one or more steps of making Compound B1. In some embodiments, the method of making Compound B1 comprises the following step:

Step B1: reacting Compound 6a:

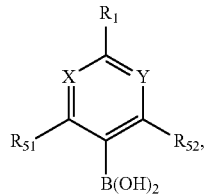

(6a)

with Compound 7:

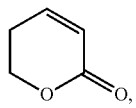

(7)

to form Compound 8a:

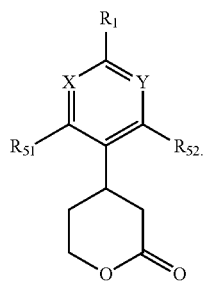

(8a)

In some embodiments, Step B1 comprises adding Compound 6a, a chiral ligand, a metal catalyst, and optionally a base (e.g., NaOH or KOH), to Compound 7. In some embodiments, Compound 6a, the chiral ligand, and the metal catalyst are added to Compound 7 in the presence of a solvent comprising dioxane and water. Examples of chiral ligands applicable in Step B1 include, but are not limited to, the structures shown in Table 1.

TABLE 1

Examples of chiral ligands

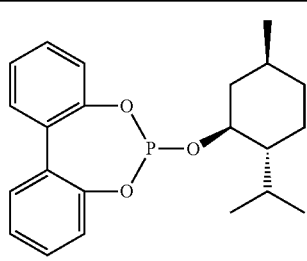

1-P(O)$_2$O

TABLE 1-continued

Examples of chiral ligands

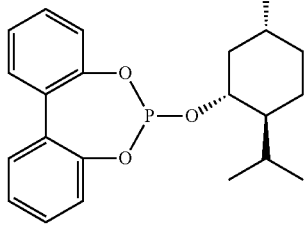

2-P(O)$_2$O

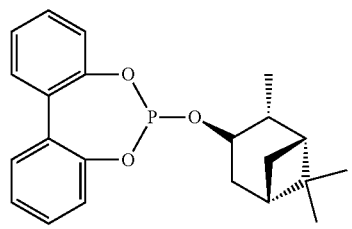

3-P(O)$_2$O

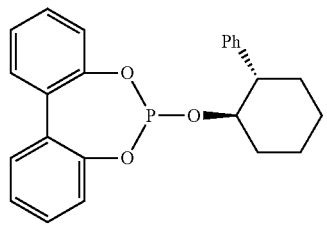

4-P(O)$_2$O

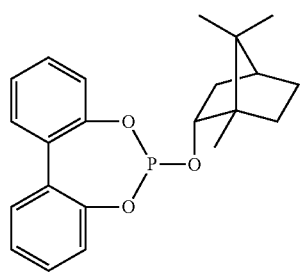

5-P(O)$_2$O

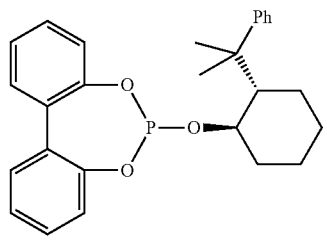

6-P(O)$_2$O

TABLE 1-continued
Examples of chiral ligands
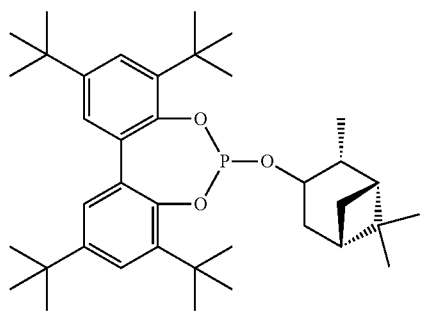
7-P(O)₂O
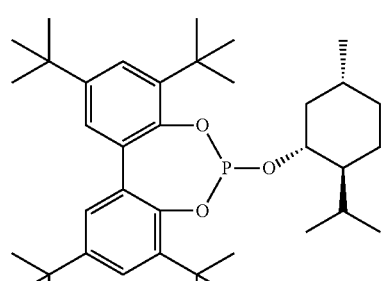
8-P(O)₂O
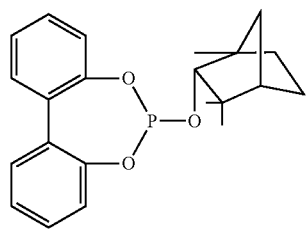
9-P(O)₂O
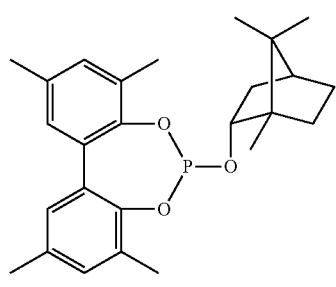
10-P(O)₂O
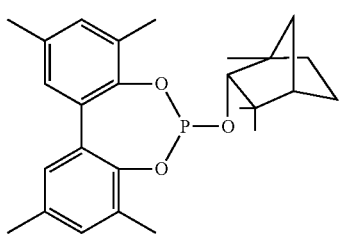
11-P(O)₂O
TABLE 1-continued
Examples of chiral ligands
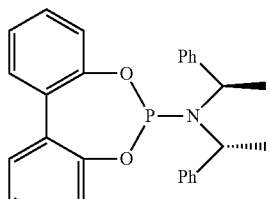
12-P(O)₂N
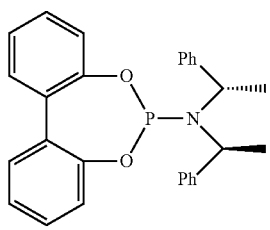
13-P(O)₂N
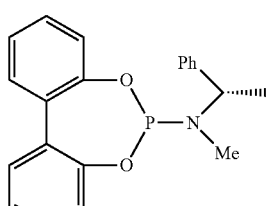
14-P(O)₂N
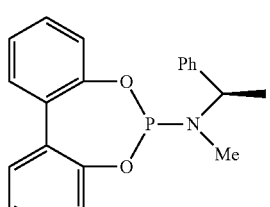
15-P(O)₂N
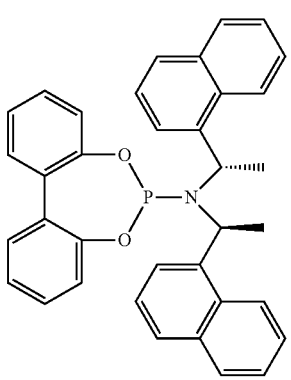
16-P(O)₂N TABLE 1-continued
Examples of chiral ligands
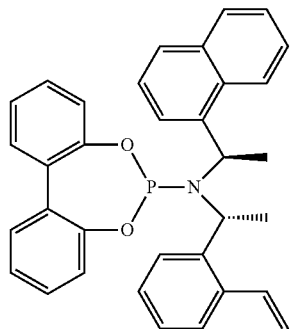
17-P(O)₂N
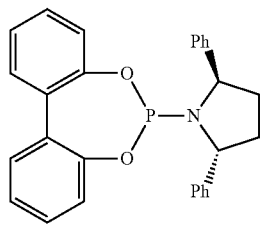
18-P(O)₂N
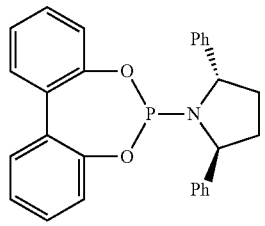
19-P(O)₂N
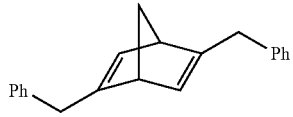 [SMILES: C1=C(Cc2ccccc2)C2C=C(Cc3ccccc3)C1C2]
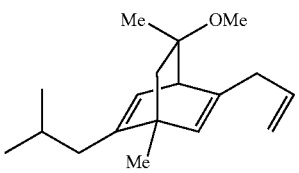 [SMILES: C=CCC1=CC2(C)CCC(C)(OC)C1C=C2CC(C)C]
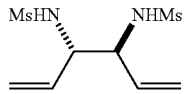
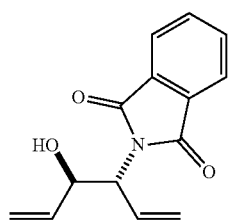 [SMILES: C=C[C@@H](O)[C@@H](C=C)N1C(=O)c2ccccc2C1=O]
TABLE 1-continued
Examples of chiral ligands
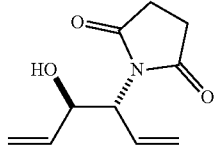
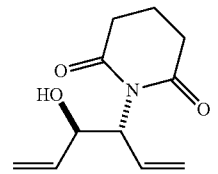
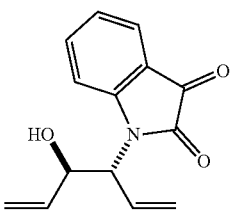 [SMILES: C=C[C@@H](O)[C@@H](C=C)N1C(=O)C(=O)c2ccccc21]
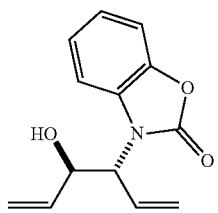 [SMILES: C=C[C@@H](O)[C@@H](C=C)n1c(=O)oc2ccccc21]
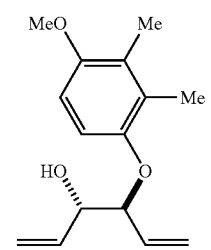 [SMILES: C=C[C@H](Oc1ccc(OC)c(C)c1C)[C@@H](O)C=C]
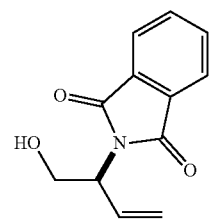

TABLE 1-continued
Examples of chiral ligands
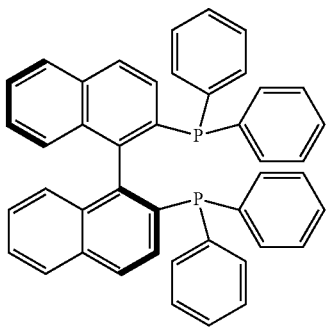
(S)-BINAP
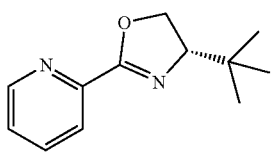
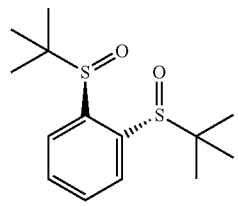 [SMILES: CC(C)(C)[S@@](=O)c1ccccc1[S@](=O)C(C)(C)C]
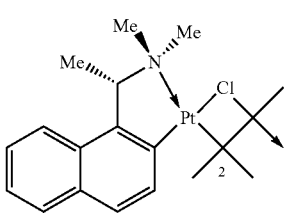
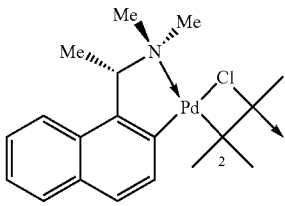
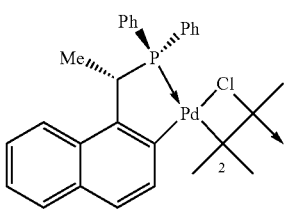
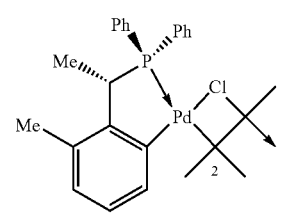
TABLE 1-continued
Examples of chiral ligands
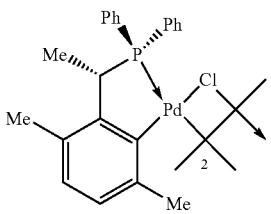
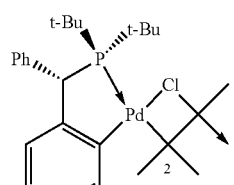
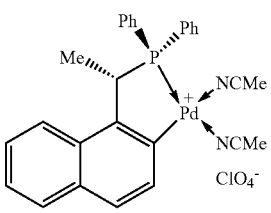
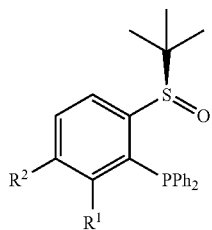
3a, R¹ = MOMO, R² = H
3b, R¹ = OCH₃, R² = H
3c, R¹ = H, R² = OCH₃
3d, R¹ = R² = OCH₃
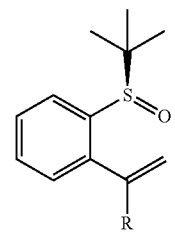
1a, R = H
1b, R = CH₃
1c, R = Ph
1d, R = 4-CH₃OC₆H₄

TABLE 1-continued

Examples of chiral ligands

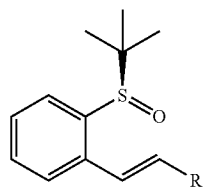

1e, R = CH₃
1f, R = Ph

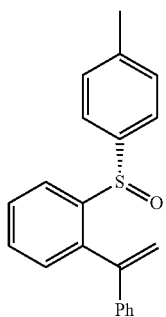 [SMILES: C=C(c1ccccc1)c1ccccc1[S@@](=O)c1ccc(C)cc1]

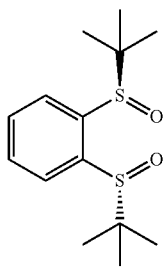 [SMILES: CC(C)(C)[S@@](=O)c1ccccc1[S@](=O)C(C)(C)C]

TABLE 1-continued

Examples of chiral ligands

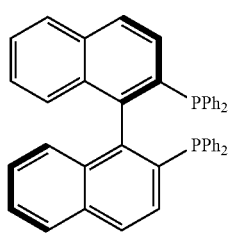

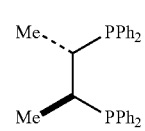

(S,S)-CHIRAPHOS

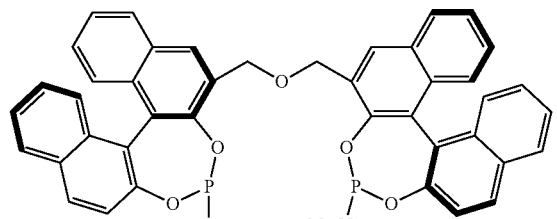

In some embodiments, the chiral ligand is (S)-BINAP.

Metal catalysts applicable in Step B1 can include palladium, rhodium, and copper. Examples of metal catalysts include, but are not limited to, the structures shown in Table 2.

TABLE 2

Examples of metal catalysts

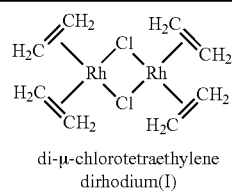

di-μ-chlorotetraethylene
dirhodium(I)

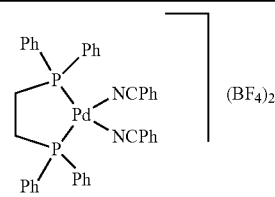

2a
[Pd(dppe)(PhCN)₂](BF₄)₂

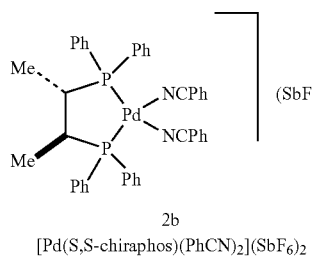

2b
[Pd(S,S-chiraphos)(PhCN)₂](SbF₆)₂

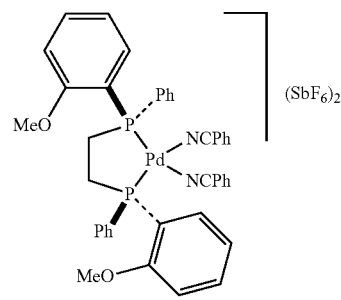

2c
[Pd(S,S-dipamp)(PhCN)₂](SbF₆)₂

TABLE 2-continued

Examples of metal catalysts

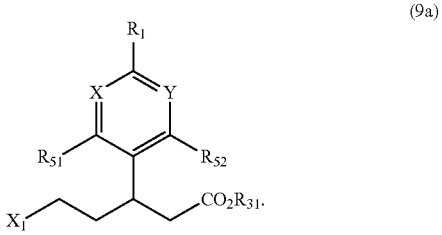

2d
[Pd(R,R-diphosphonite)(PhCN)₂](SbF₆)₂

2e
[Pd(R,R-norphos)(PhCN)₂](SbF₆)₂

Pd(OCOCF₃)₂
Bis(1,5-cyclooctadiene)rhodium(I) tetrafluoroborate
Hydroxy(cyclooctadiene)rhodium(I) dimer
Bis(norbornadiene)rhodium(I) tetrafluoroborate
Chlorobis(cyclooctene)rhodium(I), dimer Examples of copper catalysts include, but are not limited to, CuCl, CuBr, CuI, CuCN, Cu(OTf)₂, Cu(OTf), Cu(OAc), Cu(OAc)₂, and Cu(acac)₂.

In some embodiments, the metal catalyst is di-μ-chlorotetraethylene dirhodium(I).

In some embodiments, the chiral ligand is (S)-BINAP and the metal catalyst is di-μ-chlorotetraethylene dirhodium(I).

In some embodiments, Compound 6a is reacted with Compound 7 at a temperature above 0° C., e.g., about 20° C., about 30° C., about 40° C., about 50° C., about 60° C., or about 70° C., about 80° C., about 85° C., or about 90° C. In some embodiments, Compound 6a is reacted with Compound 7 for about 10 minutes, about 20 minutes, about 30 minutes, about 40 minutes, about 50 minutes, or about 60 minutes.

In some embodiments, Step B1 further comprises adding brine to the reaction between Compound 6a and Compound 7. In some embodiments, Step B1 further comprises one or more steps to extract and/or purify Compound 8a from the reaction mixture.

In some embodiments, the method of making Compound B1 comprises the following step:

Step B2: converting Compound 8a:

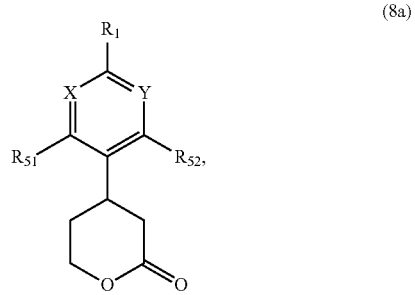

(8a)

to Compound 9a:

(9a)

In some embodiments, $X_1$ is F, Cl, Br, or I. In some embodiments, $X_1$ is F. In some embodiments, $X_1$ is Cl. In some embodiments, $X_1$ is Br. In some embodiments, $X_1$ is I.

In some embodiments, $R_{31}$ is optionally substituted alkyl, e.g., $C_1$-$C_6$ alkyl. In some embodiments, $R_{31}$ is methyl. In some embodiments, $R_{31}$ is ethyl. In some embodiments, $R_{31}$ is isopropyl. In some embodiments, $R_{31}$ is n-propyl. In some embodiments, $R_{31}$ is optionally substituted alkenyl, e.g., $C_2$-$C_6$ alkenyl. In some embodiments, $R_{31}$ is optionally substituted alkynyl, e.g., $C_2$-$C_6$ alkynyl. In some embodiments, $R_{31}$ is optionally substituted aryl, e.g., phenyl or benzyl. In some embodiments, $R_{31}$ is 2-iodophenyl.

In some embodiments, Step B2 comprises adding a metal halide and silyl halide to Compound 8a. In some embodiments, the metal halide and silyl halide are added to Compound 8a in the presence of an aprotic solvent. In some embodiments, the aprotic solvent is $CH_2Cl_2$. The metal halide can be LiF, KF, NaF, LiCl, KCl, NaCl, LiBr, KBr, NaBr, LiI, KI, or NaI. The silyl halide can be trimethylsilyl fluoride, trimethylsilyl chloride, trimethylsilyl bromide, or trimethylsilyl iodide. In some embodiments, the silyl halide is trimethylsilyl chloride. In some embodiments, Step B2 further comprises adding a protic solvent (e.g., an alcohol) to the reaction mixture comprising metal halide, silyl halide, and Compound 8a. In some embodiments, the protic solvent is methanol. In some embodiments, Step B2 further comprises warming the mixture after the addition of the protic solvent (e.g., to above 0° C., e.g., about 20° C., about 30° C., about 40° C.). In some embodiments, Step B2 further comprises stirring the reaction mixture after the addition of the protic solvent for about 10 minutes, about 20 minutes, about 30 minutes, about 40 minutes, about 50 minutes, about 60 minutes, or about 70 minutes. In some embodiments, Step B2 further comprises one or more steps to extract and/or purify Compound 9a from the reaction mixture.

In some embodiments, after the addition of the metal halide and silyl halide to Compound 8a, the delta-lactone ring on Compound 8a is opened, and an acid (Compound 9a') can be formed in the absence of any protic solvent. The structure of Compound 9a' is shown below:

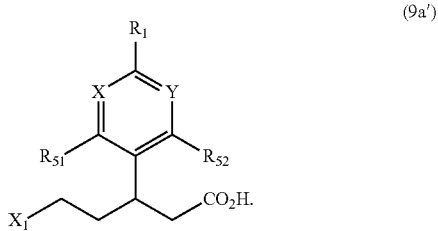

(9a')

Compound 9a' can then be converted to Compound 9a under known alkylation or esterification conditions. Known methods for the esterification of carboxylic acids include, but are not limited to, Fischer esterification, Steglich esterification, and the Mitsunobu reaction. For example, Compound 9a' can be treated with an alcohol in the presence of a dehydrating agent (e.g., sulfuric acid or molecular sieves) to be converted to Compound 9a.

In some embodiments, the method of making Compound B1 comprises the following step:

Step B3: reacting Compound 9a:

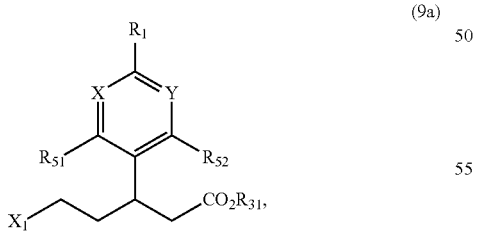

(9a)

with a phosphine compound

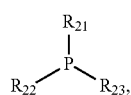

to form Compound B1:

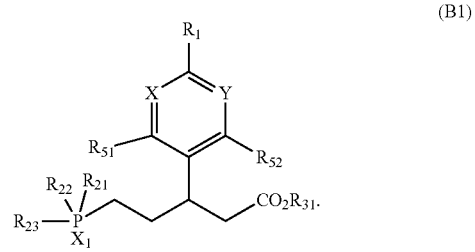

(B1)

In some embodiments, $R_{21}$, $R_{22}$, and $R_{23}$ are each independently $C_1$-$C_6$ alkyl, $C_2$-$C_6$ alkenyl, $C_2$-$C_6$ alkynyl, or phenyl. In some embodiments, $R_{21}$, $R_{22}$, and $R_{23}$ are each independently $C_1$-$C_6$ alkyl, $C_2$-$C_6$ alkenyl, or $C_2$-$C_6$ alkynyl. In some embodiments, $R_{21}$, $R_{22}$, and $R_{23}$ are each $C_1$-$C_6$ alkyl. In some embodiments, $R_{21}$, $R_{22}$, and $R_{23}$ are each $C_2$-$C_6$ alkenyl. In some embodiments, $R_{21}$, $R_{22}$, and $R_{23}$ are each $C_2$-$C_6$ alkynyl. In some embodiments, $R_{21}$, $R_{22}$, and $R_{23}$ are each phenyl. In some embodiments, the phosphine compound is triphenylphosphine ("$PPh_3$").

In some embodiments, Step B3 comprises adding the phosphine compound (e.g., $PPh_3$) to Compound 9a. In some embodiments, the phosphine compound is added to Compound 9a in the presence of an aromatic solvent. In some embodiments, the aromatic solvent is toluene. In some embodiments, the aromatic solvent is xylene. In some embodiments, the aromatic solvent is benzene. In some embodiments, the phosphine compound is reacted with Compound 9a at a temperature above 0° C., e.g., about 20° C., about 30° C., about 40° C., about 50° C., about 60° C., or about 70° C., about 80° C., about 90° C., about 100° C., about 110° C., about 120° C., or about 130° C. In some embodiments, the phosphine compound is reacted with Compound 9a for about 1-24 hours, about 5-20 hours, or about 5-15 hours. In some embodiments, Step B3 further comprises one or more steps to extract and/or purify Compound B1 from the reaction mixture. In some embodiments, the method further comprises one or more steps of making Compound B2. In some embodiments, the method of making Compound B2 comprises the following step:

Step C1: reacting Compound 6b:

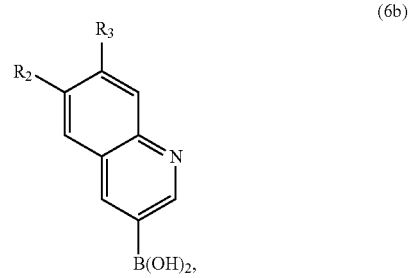

(6b)

with Compound 7:

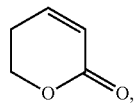

(7)

to form Compound 8b:

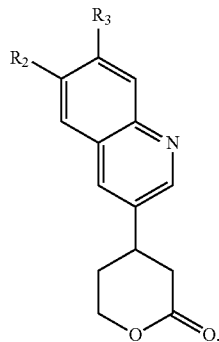
(8b)

In some embodiments, Step C1 comprises adding Compound 6b, a chiral ligand, a metal catalyst, and optionally a base (e.g., NaOH or KOH), to Compound 7. In some embodiments, Compound 6b, the chiral ligand, and the metal catalyst are added to Compound 7 in the presence of a solvent comprising dioxane and water. Examples of chiral ligands applicable in Step C1 include, but are not limited to, the structures shown in Table 1.

In some embodiments, the chiral ligand is (S)-BINAP.

Metal catalysts applicable in Step C1 can include palladium, rhodium, and copper. Examples of metal catalysts include, but are not limited to the structures shown in Table 2.

Examples of copper catalysts include, but are not limited to, CuCl, CuBr, CuI, CuCN, Cu(OTf)$_2$, Cu(OTf), Cu(OAc), Cu(OAc)$_2$, and Cu(acac)$_2$.

In some embodiments, the metal catalyst is di-μ-chlorotetraethylene dirhodium(I).

In some embodiments, the chiral ligand is (S)-BINAP and the metal catalyst is chlorotetraethylene dirhodium(I).

In some embodiments, Compound 6b is reacted with Compound 7 at a temperature above 0° C., e.g., about 20° C., about 30° C., about 40° C., about 50° C., about 60° C., or about 70° C., about 80° C., about 85° C., or about 90° C. In some embodiments, Compound 6b is reacted with Compound 7 for about 10 minutes, about 20 minutes, about 30 minutes, about 40 minutes, about 50 minutes, or about 60 minutes.

In some embodiments, Step C1 further comprises adding brine to the reaction between Compound 6b and Compound 7. In some embodiments, Step C1 further comprises one or more steps to extract and/or purify Compound 8b from the reaction mixture.

In some embodiments, the method of making Compound B2 comprises the following step:

Step C2: converting Compound 8b:

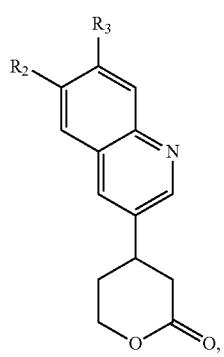
(8b)

to Compound 9b:

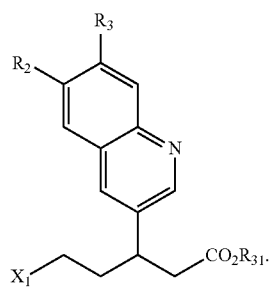
(9b)

In some embodiments, $X_1$ is F, Cl, Br, or I. In some embodiments, $X_1$ is F. In some embodiments, $X_1$ is Cl. In some embodiments, $X_1$ is Br. In some embodiments, $X_1$ is I.

In some embodiments, $R_{31}$ is optionally substituted alkyl, e.g., $C_1$-$C_6$ alkyl. In some embodiments, $R_{31}$ is methyl. In some embodiments, $R_{31}$ is ethyl. In some embodiments, $R_{31}$ is isopropyl. In some embodiments, $R_{31}$ is n-propyl. In some embodiments, $R_{31}$ is optionally substituted alkenyl, e.g., $C_2$-$C_6$ alkenyl. In some embodiments, $R_{31}$ is optionally substituted alkynyl, e.g., $C_2$-$C_6$ alkynyl. In some embodiments, $R_{31}$ is optionally substituted aryl, e.g., phenyl or benzyl. In some embodiments, $R_{31}$ is 2-iodophenyl.

In some embodiments, Step C2 comprises adding a metal halide and silyl halide to Compound 8b. In some embodiments, the metal halide and silyl halide are added to Compound 8b in the presence of an aprotic solvent. In some embodiments, the aprotic solvent is $CH_2Cl_2$. The metal halide can be LiF, KF, NaF, LiCl, KCl, NaCl, LiBr, KBr, NaBr, LiI, KI, or NaI. The silyl halide can be trimethylsilyl fluoride, trimethylsilyl chloride, trimethylsilyl bromide, or trimethylsilyl iodide. In some embodiments, the silyl halide is trimethylsilyl chloride. In some embodiments, Step C2 further comprises adding a protic solvent (e.g., an alcohol) to the reaction mixture comprising metal halide, silyl halide, and Compound 8b. In some embodiments, the protic solvent is methanol. In some embodiments, Step C2 further comprises warming the mixture after the addition of the protic solvent (e.g., to above 0° C., e.g., about 20° C., about 30° C., about 40° C.). In some embodiments, Step C2 further comprises stirring the reaction mixture after the addition of the protic solvent for about 10 minutes, about 20 minutes, about 30 minutes, about 40 minutes, about 50 minutes, about 60 minutes, or about 70 minutes. In some embodiments, Step C2 further comprises one or more steps to extract and/or purify Compound 9b from the reaction mixture.

In some embodiments, after the addition of the metal halide and silyl halide to Compound 8b, the delta-lactone ring on Compound 8b is opened, and an acid (Compound 9b') can be formed in the absence of any protic solvent. The structure of Compound 9b' is shown below:

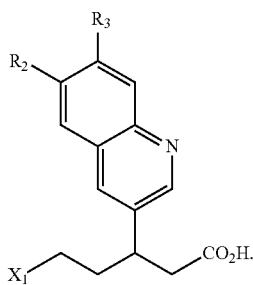

(9b')

Compound 9b' can then be converted to Compound 9b under known alkylation or esterification conditions. Known methods for the esterification of carboxylic acids include, but are not limited to, Fischer esterification, Steglich esterification, and the Mitsunobu reaction. For example, Compound 9b' can be treated with an alcohol in the presence of a dehydrating agent (e.g., sulfuric acid or molecular sieves) to be converted to Compound 9b.

In some embodiments, the method of making Compound B2 comprises the following step:

Step C3: reacting Compound 9b:

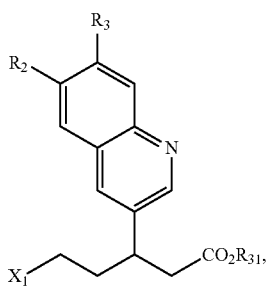

(9b)

with a phosphine compound

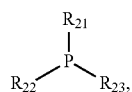

to form Compound B2:

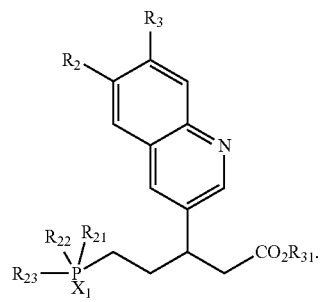

(B2)

In some embodiments, Step C3 comprises adding the phosphine compound (e.g., $PPh_3$) to Compound 9b. In some embodiments, the phosphine compound is added to Compound 9b in the presence of an aromatic solvent. In some embodiments, the aromatic solvent is toluene. In some embodiments, the aromatic solvent is xylene. In some embodiments, the aromatic solvent is benzene. In some embodiments, the phosphine compound is reacted with Compound 9b at a temperature above 0° C., e.g., about 20° C., about 30° C., about 40° C., about 50° C., about 60° C., or about 70° C., about 80° C., about 90° C., about 100° C., about 110° C., about 120° C., or about 130° C. In some embodiments, the phosphine compound is reacted with Compound 9b for about 1-24 hours, about 5-20 hours, or about 5-15 hours. In some embodiments, Step C3 further comprises one or more steps to extract and/or purify Compound B2 from the reaction mixture.

In another aspect, the present disclosure provides a method of making Compound Y:

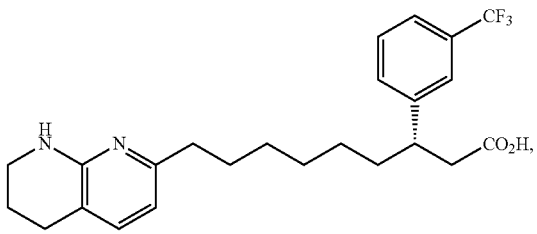

(Y)

or a salt thereof, comprising:

Step 1': reacting Compound A3:

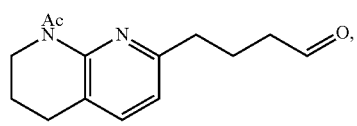

(A3)

with Compound B3:

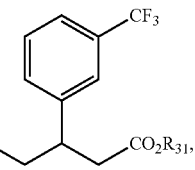

(B3)

wherein $X_1$ is halogen, and $R_{21}$, $R_{22}$, $R_{23}$, and $R_{31}$ are each independently selected from the group consisting of optionally substituted alkyl, optionally substituted alkenyl, optionally substituted alkynyl, and optionally substituted aryl, to form Compound 1A:

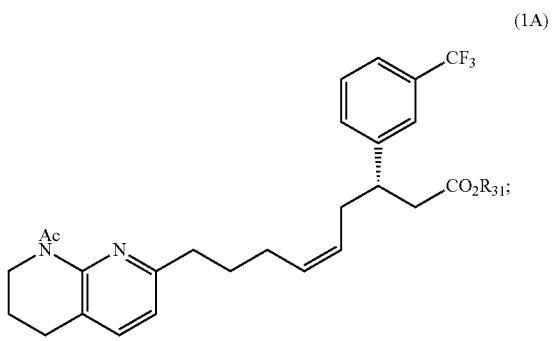

(1A)

and

Step 2': reducing Compound 1A:

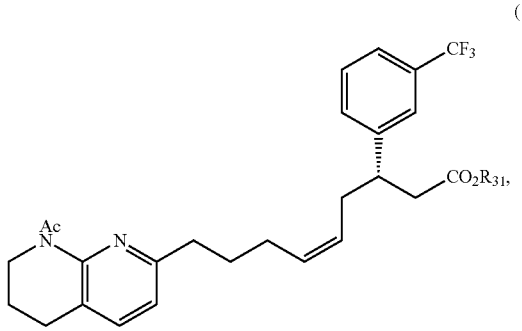

(1A)

optionally in the presence of a catalyst, to form Compound Y:

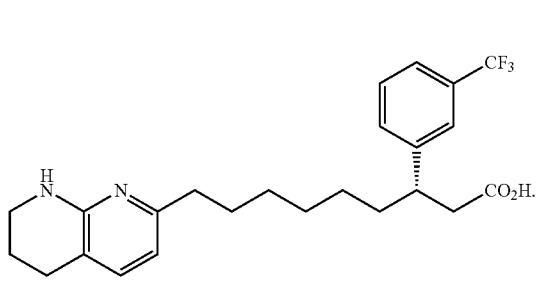

(Y)

In some embodiments, $X_1$ is F, Cl, Br, or I. In some embodiments, $X_1$ is F. In some embodiments, $X_1$ is Cl. In some embodiments, $X_1$ is Br. In some embodiments, $X_1$ is I.

In some embodiments, $R_{21}$, $R_{22}$, $R_{23}$, and $R_{31}$ are each independently $C_1$-$C_6$ alkyl, $C_2$-$C_6$ alkenyl, $C_2$-$C_6$ alkynyl, or phenyl. In some embodiments, $R_{21}$, $R_{22}$, $R_{23}$, and $R_{31}$ are each independently $C_1$-$C_6$ alkyl, $C_2$-$C_6$ alkenyl, or $C_2$-$C_6$ alkynyl. In some embodiments, $R_{21}$, $R_{22}$, $R_{23}$, and $R_{31}$ are each $C_1$-$C_6$ alkyl. In some embodiments, $R_{21}$, $R_{22}$, $R_{23}$, and $R_{31}$ are each $C_2$-$C_6$ alkenyl. In some embodiments, $R_{21}$, $R_{22}$, $R_{23}$, and $R_{31}$ are each $C_2$-$C_6$ alkynyl. In some embodiments, $R_{21}$, $R_{22}$, $R_{23}$, and $R_{31}$ are each phenyl. In some embodiments, $R_{31}$ is methyl, ethyl, isopropyl, n-propyl, phenyl, benzyl, or 2-iodophenyl.

In some embodiments, Step 1' comprises adding a non-nucleophilic base to Compound B3. In some embodiments, the non-nucleophilic base is added to Compound B3 in the presence of an aprotic solvent. In some embodiments, the aprotic solvent is tetrahydrofuran ("THF"). In some embodiments, Step 1' further comprises reacting Compound B3 with the non-nucleophilic base. In some embodiments, the non-nucleophilic base is potassium bis(trimethylsilyl)amide ("KHMDS") or sodium bis(trimethylsilyl)amide ("NaHMDS"). In some embodiments, the non-nucleophilic base is KHMDS.

In some embodiments, Step 1' comprises reacting the non-nucleophilic base with Compound B3 at a temperature below 0° C., e.g., about −10° C., about −20° C., about −30° C., about −40° C., about −50° C., about −60° C., about −70° C., about −80° C., about −90° C., or about −100° C. In some embodiments, the non-nucleophilic base is reacted with Compound B3 for less than 2 hours, less than 90 minutes, less than 60 minutes, less than 50 minutes, less than 40 minutes, less than 30 minutes, or less than 20 minutes. In some embodiments, the non-nucleophilic base is reacted with Compound B3 for about 30 minutes, about 20 minutes, about 15 minutes, or about 10 minutes. Specifically, the reaction of the non-nucleophilic base with Compound B3 produces a ylide.

In some embodiments, Step 1' further comprises adding Compound A3 to the reaction mixture comprising Compound B3 and the non-nucleophilic base. In some embodiments, Step 1' comprises reacting Compound A3 with the reaction mixture comprising Compound B3 and the non-nucleophilic base at a temperature below 0° C., e.g., about −10° C., about −20° C., about −30° C., about −40° C., about −50° C., about −60° C., about −70° C., about −80° C., about −90° C., or about −100° C. In some embodiments, Compound A3 is reacted with the reaction mixture comprising Compound B3 and the non-nucleophilic base for less than 2 hours, less than 90 minutes, less than 60 minutes, less than 50 minutes, less than 40 minutes, less than 30 minutes, or less than 20 minutes. In some embodiments, Compound A3 is reacted with the reaction mixture comprising Compound B3 and the non-nucleophilic base for about 30 minutes, about 20 minutes, about 15 minutes, or about 10 minutes.

In some embodiments, Step 1' further comprises raising the temperature of the reaction between Compound A3 and the mixture comprising Compound B3 and the non-nucleophilic base to a temperature above 0° C., e.g., about 5° C., about 10° C., about 15° C., about 20° C., about 25° C., or about 30° C. In some embodiments, Step 1' further comprise one or more steps to extract and/or purify Compound 1A from the final reaction mixture.

In some embodiments, Step 2' comprises reacting Compound 1A with a hydrogen source, optionally in the presence of a catalyst. The catalyst can be added to Compound 1A prior to, concurrently, or after the addition of the hydrogen source. Examples of hydrogen sources include, but are not limited to, $H_2$, hydrazine, dihydronaphthalene, dihydroanthracene, isopropanol, and formic acid. The catalyst can be a homogeneous catalyst or a heterogeneous catalyst. Examples of catalysts include, but are not limited to, platinum, palladium, rhodium, ruthenium, nickel, gold, and a combination thereof. The catalyst can be an organometallic compound in which a metal (e.g., platinum, palladium, rhodium, ruthenium, nickel, or gold) is complexed with one or more organic ligands. In some embodiments, the catalyst is selected from Pd(OH)$_2$/C, Pd(OAc)$_2$, PdCl$_2$(tBu$_2$PhP)$_2$ [dichlorobis(di-tert-butylphenylphosphine palladium (II)], and PdCl$_2$(DPEPhos)[bis(diphenylphosphinophenyl)ether palladium (II) chloride].

In some embodiments, the hydrogen source is $H_2$. Accordingly, Step 2' comprises adding $H_2$ to Compound 1A in the presence of a protic solvent. In some embodiments, the protic solvent is an alcohol selected from methanol, ethanol, isopropanol, butanol, and t-butanol. In some embodiments, the protic solvent is methanol. In some embodiments, the catalyst includes palladium, such as palladium on barium sulfate and palladium on carbon. In some embodiments, the catalyst is $Pd(OH)_2/C$. In some embodiments, the catalyst is $PdCl_2/C$. In some embodiments, $H_2$ is reacted with Compound 1A at a temperature above 0° C., e.g., about 5° C., about 10° C., about 15° C., about 20° C., about 25° C., or about 30° C. In some embodiments, $H_2$ is reacted with Compound 1A for about 1-24 hours, about 5-20 hours, or about 10-15 hours. In some embodiments, $H_2$ is reacted with Compound 1A for about 5 hours, about 8 hours, about 10 hours, about 12 hours, or about 14 hours. In some embodiments, Step 2' further comprises adding a base to the reaction of $H_2$ and Compound 1A, followed by the addition of an acid after stirring for a period of time (e.g., about 1 hour, about 1.5 hours, about 2 hours, about 2.5 hours, about 3 hours, about 3.5 hours, or about 4 hours). In some embodiments, the base is KOH, NaOH, or a combination thereof. In some embodiments, the base is NaOH. In some embodiments, the acid is $HNO_3$, HCl, $H_2SO_4$, or a combination thereof. In some embodiments, the acid is HCl. In some embodiments, Step 2' further comprises one or more steps to extract and/or purify Compound Y from the reaction mixture.

In some embodiments, the method further comprises mixing Compound Y with a solvent and forming a solvate. In some embodiments, the solvate forms a crystalline solid. "Solvate" means a solvent addition form that contains either a stoichiometric or non-stoichiometric amounts of the solvent molecules. Some compounds have a tendency to trap a fixed molar ratio of the solvent molecules in the crystalline solid state, thus forming a solvate. For example, the solvent is 2-amino-iso-butanol and the solvate is Compound Z:

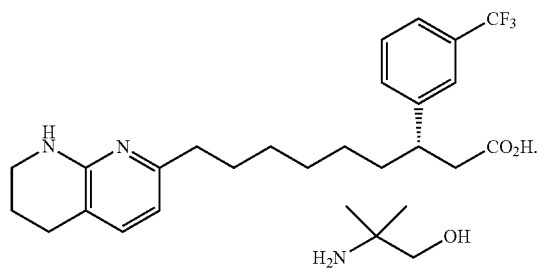

(Z)

In some embodiments, Compound Z forms a crystalline solid.

In some embodiments, the mixture of Compound Y and the solvent is heated to a first temperature to make a homogeneous solution, which is then cooled to a second temperature to produce crystals. The first temperature can be above 0° C., e.g., about 10° C., about 20° C., about 30° C., about 40° C., about 50° C., about 60° C., about 70° C., about 80° C., about 90° C. The second temperature can be below 0° C., e.g., about −10° C., about −20° C., or about −30° C.

In some embodiments, the method further comprises one or more steps of making Compound A3. In some embodiments, the method of making Compound A3 comprises the following step:

Step A1': reacting Compound 22:

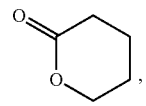

(22)

with Compound 23:

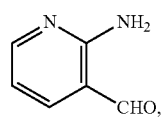

(23)

to form Compound 24:

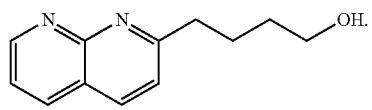

(24)

In some embodiments, Step A1' comprises adding n-butyllithium to dimethyl methylphosphonate to generate a mixture. In some embodiments, n-butyllithium is added to dimethyl methylphosphonate in the presence of an aprotic solvent. In some embodiments, the aprotic solvent is THF. In some embodiments, n-butyllithium is added to dimethyl methylphosphonate at a temperature below 0° C., e.g., about −10° C., about −20° C., about −30° C., about −40° C., about −50° C., about −60° C., about −70° C., about −80° C., about −90° C., or about −100° C. In some embodiments, the reaction of n-butyllithium with dimethyl methylphosphonate produces a carbanion.

In some embodiments, Step A1' comprises adding Compound 22 to the mixture of n-butyllithium and dimethyl methylphosphonate, optionally followed by the addition of $NH_4Cl$. In some embodiments, Step A1' comprises separating an organic phase from the reaction mixture. In some embodiments, Step A1' comprises removing excess dimethyl methylphosphonate from the organic phase to afford crude β-ketophosphonate. In some embodiments, Step A1' comprises adding Compound 23 to the crude β-ketophosphonate. In some embodiments, Compound 23 is added to the crude β-ketophosphonate in the presence of a protic solvent, optionally at a temperature above 0° C., e.g., about 5° C., about 10° C., about 15° C., about 20° C., about 25° C., or about 30° C. In some embodiments, the protic solvent is an alcohol selected from methanol, ethanol, isopropanol, butanol, and t-butanol. In some embodiments, the protic solvent is methanol. In some embodiments, Step A1' comprises adding a base to the crude β-ketophosphonate. In some embodiments, the base is NaOH, KOH, or a combination thereof. In some embodiments, the base is NaOH. In some embodiments, Step A1' further comprises one or more steps to extract and/or purify Compound 24 from the reaction mixture.

In some embodiments, the method of making Compound A3 comprises the following step:

Step A2': reducing Compound 24:

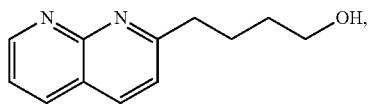
(24)

optionally in the presence of a catalyst. In some embodiments, the reduction of Compound 24 results in a tetrahydronaphthyridine. In some embodiment, the reduction is followed by reacting the tetrahydronaphthyridine with acetic anhydride ("Ac$_2$O") to form Compound 25:

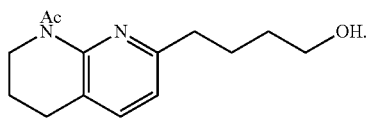
(25)

In some embodiments, Step A2' comprises reacting Compound 24 with a hydrogen source, optionally in the presence of a catalyst. The catalyst can be added to Compound 24 prior to, concurrently, or after the addition of the hydrogen source. Examples of hydrogen sources include, but are not limited to, H$_2$, hydrazine, dihydronaphthalene, dihydroanthracene, isopropanol, and formic acid. The catalyst can be a homogeneous catalyst or a heterogeneous catalyst. Examples of catalysts include, but are not limited to, platinum, palladium, rhodium, ruthenium, nickel, gold, and a combination thereof. The catalyst can be an organometallic compound in which a metal (e.g., platinum, palladium, rhodium, ruthenium, nickel, or gold) is complexed with one or more organic ligands. In some embodiments, the catalyst is selected from Pd(OH)$_2$/C, Pd(OAc)$_2$, PdCl$_2$(tBu$_2$PhP)$_2$ [dichlorobis(di-tert-butylphenylphosphine palladium (II)], and PdCl$_2$(DPEPhos)[bis(diphenylphosphinophenyl)ether palladium (II) chloride].

In some embodiments, the hydrogen source is H$_2$. Accordingly, Step A2' comprises adding H$_2$ to Compound 24 in the presence of a protic solvent. In some embodiments, the protic solvent is an alcohol selected from methanol, ethanol, isopropanol, butanol, and t-butanol. In some embodiments, the protic solvent is methanol. In some embodiments, the catalyst includes palladium, such as palladium on barium sulfate and palladium on carbon. In some embodiments, the catalyst is Pd(OH)$_2$/C. In some embodiments, the catalyst is PdCl$_2$/C.

In some embodiments, H$_2$ is reacted with Compound 24 at a temperature above 0° C., e.g., about 5° C., about 10° C., about 15° C., about 20° C., about 25° C., or about 30° C. In some embodiments, H$_2$ is reacted with Compound 24 for about 1-24 hours, about 5-20 hours, or about 10-18 hours. In some embodiments, H$_2$ is reacted with Compound 24 for about 5 hours, about 8 hours, about 10 hours, about 12 hours, about 14 hours, about 16 hours, about 18 hours, or about 20 hours. H$_2$ is reacted with Compound 24 to generate a tetrahydronaphthyridine, to which 4-(dimethylamino)pyridine ("DMAP") is added. In some embodiments, DMAP is added to the tetrahydronaphthyridine in the presence of pyridine and Ac$_2$O. In some embodiments, Step A2' further comprises adding potassium carbonate or sodium carbonate to the mixture comprising DMAP and tetrahydronaphthyridine, optionally in the presence of a protic solvent (e.g., methanol). In some embodiments, Step A2' further comprises adding NH$_4$Cl after the addition of potassium carbonate or sodium carbonate. In some embodiments, Step A2' further comprises one or more steps to extract and/or purify Compound 25 from the reaction mixture.

In some embodiments, the method of making Compound A3 comprises the following step:

Step A3': converting Compound 25:

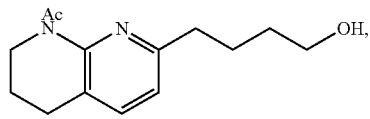
(25)

to Compound A3:

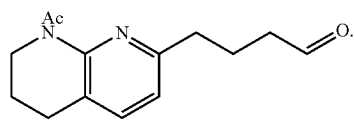
(A3)

In some embodiments, Step A3' comprising adding, to Compound 25, a compound capable of transforming primary alcohols to aldehydes. Compounds capable of transforming primary alcohols to aldehydes include, but are not limited to, chromium-based reagents, such as Collins reagent (CRO$_3$.Py2), PDC or PCC; activated DMSO, resulting from reaction of DMSO with electrophiles, such as oxalyl chloride (Swern oxidation), a carbodiimide (Pfitzner-Moffatt oxidation) or the complex SO3.Py (Parikh-Doering oxidation); hypervalent iodine compounds, such as Dess-Martin periodinane or 2-Iodoxybenzoic acid; catalytic TPAP in presence of excess of NMO (Ley oxidation); and catalytic TEMPO in the presence of excess bleach (NaOCl) (Oxoammonium-catalyzed oxidation).

In some embodiments, the compound capable of transforming primary alcohols to aldehydes is Dess-Martin periodinane. In some embodiments, Dess-Martin periodinane is added to Compound 25 in the presence of an aprotic solvent. In some embodiments, the aprotic solvent is CH$_2$Cl$_2$. In some embodiments, Dess-Martin periodinane is reacted with Compound 25 at a temperature above 0° C., e.g., about 5° C., about 10° C., about 15° C., about 20° C., about 25° C., or about 30° C. In some embodiments, Dess-Martin periodinane is reacted with Compound 25 for about 1-10 hours. In some embodiments, Dess-Martin periodinane is reacted with Compound 25 for about 30 minutes, about 60 minutes, about 90 minutes, about 2 hours, about 2.5 hours, about 3 hours, about 3.5 hours, or about 4 hours. In some embodiments, Step A3' further comprises adding a base to the mixture comprising Dess-Martin periodinane and Compound 25. In some embodiments, Step A3' further comprises one or more steps to extract and/or purify Compound A3 from the reaction mixture.

In some embodiments, the method further comprises one or more steps of making Compound B3. In some embodiments, the method of making Compound B3 comprises the following step:

Step B1': reacting Compound 26:

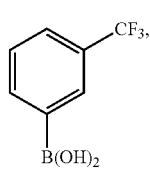
(26)

with Compound 27:

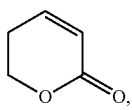
(27)

to form Compound 28:

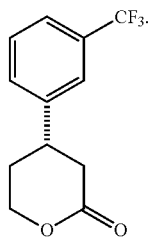
(28)

In some embodiments, Step B1' comprises adding Compound 26, a chiral ligand, a metal catalyst, and optionally a base (e.g., NaOH or KOH), to Compound 27. In some embodiments, Compound 26, the chiral ligand and the metal catalyst are added to Compound 27 in the presence of a solvent comprising dioxane and water. Examples of chiral ligands applicable in Step B1' include, but are not limited to, the structures shown in Table 1. In some embodiments, the chiral ligand is (S)-BINAP.

Metal catalysts applicable in Step B1' can include palladium, rhodium, and copper. Examples of metal catalysts include, but are not limited to the structures shown in Table 2.

In some embodiments, the metal catalyst is di-μ-chlorotetraethylene dirhodium(I).

In some embodiments, the chiral ligand is (S)-BINAP and the metal catalyst is di-μ-chlorotetraethylene dirhodium(I).

In some embodiments, Compound 26 is reacted with Compound 27 at a temperature above 0° C., e.g., about 20° C., about 30° C., about 40° C., about 50° C., about 60° C., or about 70° C., about 80° C., about 85° C., or about 90° C. In some embodiments, Compound 26 is reacted with Compound 27 for about 10 minutes, about 20 minutes, about 30 minutes, about 40 minutes, about 50 minutes, or about 60 minutes.

In some embodiments, Step B1' further comprises adding brine to the reaction between Compound 26 and Compound 27. In some embodiments, Step B1' further comprises one or more steps to extract and/or purify Compound 28 from the reaction mixture.

In some embodiments, the method of making Compound B3 comprises the following step:

Step B2': converting Compound 28:

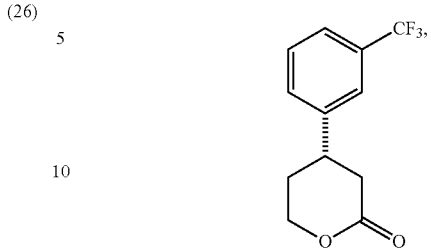
(28)

to Compound 29:

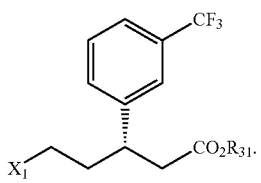
(29)

In some embodiments, $X_1$ is F, Cl, Br, or I. In some embodiments, $X_1$ is F. In some embodiments, $X_1$ is Cl. In some embodiments, $X_1$ is Br. In some embodiments, $X_1$ is I.

In some embodiments, $R_{31}$ is optionally substituted alkyl, e.g., $C_1$-$C_6$ alkyl. In some embodiments, $R_{31}$ is methyl. In some embodiments, $R_{31}$ is ethyl. In some embodiments, $R_{31}$ is isopropyl. In some embodiments, $R_{31}$ is n-propyl. In some embodiments, $R_{31}$ is optionally substituted alkenyl, e.g., $C_2$-$C_6$ alkenyl. In some embodiments, $R_{31}$ is optionally substituted alkynyl, e.g., $C_2$-$C_6$ alkynyl. In some embodiments, $R_{31}$ is optionally substituted aryl, e.g., phenyl or benzyl. In some embodiments, $R_{31}$ is 2-iodophenyl.

In some embodiments, Step B2' comprises adding a metal halide and silyl halide to Compound 28. In some embodiments, the metal halide and silyl halide are added to Compound 28 in the presence of an aprotic solvent. In some embodiments, the aprotic solvent is $CH_2Cl_2$. The metal halide can be LiF, KF, NaF, LiCl, KCl, NaCl, LiBr, KBr, NaBr, LiI, KI, or NaI. The silyl halide can be trimethylsilyl fluoride, trimethylsilyl chloride, trimethylsilyl bromide, or trimethylsilyl iodide. In some embodiments, the silyl halide is trimethylsilyl chloride. In some embodiments, Step B2' further comprises adding a protic solvent (e.g., an alcohol) to the reaction mixture comprising metal halide, silyl halide, and Compound 28. In some embodiments, the protic solvent is methanol. In some embodiments, Step B2' further comprises warming the mixture after the addition of the protic solvent (e.g., to above 0° C., e.g., about 20° C., about 30° C., about 40° C.). In some embodiments, Step B2' further comprises stirring the reaction mixture after the addition of the protic solvent for about 10 minutes, about 20 minutes, about 30 minutes, about 40 minutes, about 50 minutes, about 60 minutes, or about 70 minutes. In some embodiments, Step B2' further comprises one or more steps to extract and/or purify Compound 29 from the reaction mixture.

In some embodiments, after the addition of the metal halide and silyl halide to Compound 28, the delta-lactone ring on Compound 28 is opened, and an acid (Compound 29') can be formed in the absence of any protic solvent. The structure of Compound 29' is shown below:

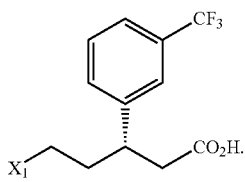

(29')

Compound 29' can then be converted to Compound 29 under known alkylation or esterification conditions. Known methods for the esterification of carboxylic acids include, but are not limited to, Fischer esterification, Steglich esterification, and the Mitsunobu reaction. For example, Compound 29' can be treated with an alcohol in the presence of a dehydrating agent (e.g., sulfuric acid or molecular sieves) to be converted to Compound 29.

In some embodiments, the method of making Compound B3 comprises the following step:

Step B3': reacting Compound 29:

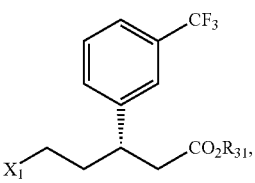

(29)

with a phosphine compound

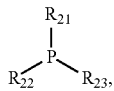

to form Compound B3:

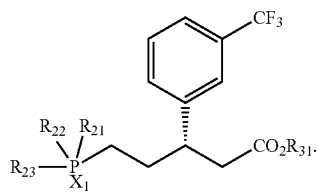

(B3)

In some embodiments, $R_{21}$, $R_{22}$, and $R_{23}$ are each independently $C_1$-$C_6$ alkyl, $C_2$-$C_6$ alkenyl, $C_2$-$C_6$ alkynyl, or phenyl. In some embodiments, $R_{21}$, $R_{22}$, and $R_{23}$ are each independently $C_1$-$C_6$ alkyl, $C_2$-$C_6$ alkenyl, or $C_2$-$C_6$ alkynyl. In some embodiments, $R_{21}$, $R_{22}$, and $R_{23}$ are each $C_1$-$C_6$ alkyl. In some embodiments, $R_{21}$, $R_{22}$, and $R_{23}$ are each $C_2$-$C_6$ alkenyl. In some embodiments, $R_{21}$, $R_{22}$, and $R_{23}$ are each $C_2$-$C_6$ alkynyl. In some embodiments, $R_{21}$, $R_{22}$, and $R_{23}$ are each phenyl. In some embodiments, the phosphine compound is triphenylphosphine ("$PPh_3$").

In some embodiments, Step B3' comprises adding the phosphine compound (e.g., $PPh_3$) to Compound 29. In some embodiments, the phosphine compound is added to Compound 29 in the presence of an aromatic solvent. In some embodiments, the aromatic solvent is toluene. In some embodiments, the aromatic solvent is xylene. In some embodiments, the aromatic solvent is benzene. In some embodiments, the phosphine compound is reacted with Compound 29 at a temperature above 0° C., e.g., about 20° C., about 30° C., about 40° C., about 50° C., about 60° C., or about 70° C., about 80° C., about 90° C., about 100° C., about 110° C., about 120° C., or about 130° C. In some embodiments, the phosphine compound is reacted with Compound 29 for about 1-24 hours, about 5-20 hours, or about 5-15 hours. In some embodiments, Step B3' further comprises one or more steps to extract and/or purify Compound B3 from the reaction mixture.

For use in medicine, the salts of Compound Y of the present disclosure refer to non-toxic "pharmaceutically acceptable salts". Other salts may, however, be useful in the preparation of Compound Y or pharmaceutically acceptable salts thereof. Salts encompassed within the term "pharmaceutically acceptable salts" refer to non-toxic salts of Compound Y which can be prepared by reacting the free base with a suitable organic or inorganic acid. Representative salts include the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamottle (embonate), palmitate, pantothenate, phosphate/diphosphate, polygalacturonate, salicylate, stearate, sulfate, subacetate, succinate, tannate, tartrate, teoclate, tosylate, triethiodide, and valerate. Furthermore, suitable pharmaceutically acceptable salts of Compound Y may include alkali metal salts, e.g., sodium or potassium salts; alkaline earth metal salts, e.g., calcium or magnesium salts; and salts formed with suitable organic ligands, e.g., quaternary ammonium salts which may be derived from ammonia or organic amines, such as, for example, diethylamine, triethylamine, ethyldiisopropylamine, procaine, dibenzylamine, N-methylmorpholine, dihydroabietylamine, or methylpiperidine.

In some embodiments, the methods of the present disclosure produce (i.e., without further purification) substantially pure compound of the present application. The term "purity" as used herein refers to the amount of a compound of the present application based on analytic methods commonly used in the art (e.g., HPLC). Purity is based on the "organic" purity of the compound, and does not include a measure of any amount of water, solvent, etc. In some embodiments, the purity of a compound of the present application is compared to the purity of a reference standard, e.g., a known sample of Compound Y by comparing the area under the peak in HPLC. In some embodiments, a compound of the present application prepared according to the methods of the present disclosure has a purity of greater than about 96%, e.g., greater than about 98% or greater than about 99%. For example, the purity of a compound of the present application prepared according to the methods of the present disclosure is 96.0%, 96.1%, 96.2%, 96.3%, 96.4%, 96.5%, 96.6%, 96.7%, 96.8%, 96.9%, 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8%, or 99.9%. For example, the purity of a compound of the present application prepared according to the methods of the present disclosure is 98.0%, 98.5%, 99.0%, 99.5%, 99.6%, 99.7%, 99.8%, or 99.9%.

In some embodiments, the methods of the present disclosure produce highly pure compound of the present application on a large scale (e.g., commercial scale). The term "commercial scale" refers to yield of a single batch of at least about 100 g. In some embodiments, the methods of the present disclosure produce highly pure compound of the present application in a large amount of at least 100 g, at least 200 g, at least 500 g, at least 1 kg, at least 2 kg, or at least 5 kg.

Characterization Methods and Assays

Methods for characterizing compounds or intermediates are well-known in the art, including HPLC, NMR spectrometry, mass spectrometry, elemental analysis, infrared spectroscopy, and X-ray diffraction. For example, instrumentation for chiral chromatography is shown in Table 3.

TABLE 3

| System | HPLC with UV detector or equivalent |
|---|---|
| Pump | Constant flow HPLC pump capable of running the gradient program |
| Detector | DAD/VWD |
| Balance | Analytical Balance capable of weighing (±) 0.01 mg accuracy |

As an example, the chromatographic conditions are shown in Table 4.

TABLE 4

| Column | CHIRAL PAK AD-H, 250 × 4.6 mm, 5 μm |
|---|---|
| Flow rate | 0.8 mL/min |
| Column Temperature | 40° C. |
| Wavelength | 205 nm |
| Run Time | 25 minutes |
| Injection volume | 10 μL |
| Diluent | Ethanol:Methanol (1:1) |
| Mode | Isocratic |
| Mobile phase A | n-Hexane |
| Mobile phase B | 0.1% DEA in Ethanol |
| Mobile phase composition | MPA:MPB::85:15 |

Mobile phase A (n-hexane) is prepared by transferring 1000 mL of n-hexane into a clean and dry one liter mobile phase bottle. Mobile phase B (0.1% DEA in ethanol) is prepared by (1) transferring 1000 ml of Ethanol into a clean and dry one liter mobile phase bottle, (2) adding 1.0 mL of diethylamine, and (3) sonicating to degas.

Biological Assays
Cell Adhesion Assays

The ability of the compound of formula I to block cell adhesion to vitronectin and/or fibronectin may be tested with methods or techniques known in the art, for example, the procedure described below.

Adhesion plates preparation: Cell culture plates are coated with vitronectin or fibronectin.

Cell culturing and loading: Exemplary cells (e.g., HMVEC cells, RLMVEC cells, and RAEC cells) are used for the compound testing. Cells are grown and then suspended for testing.

Adhesion assay: Test compounds are added to the cell suspension. After incubation, the cells that do not adhere to vitronectin- or fibronectin-coated plates are removed by gentle washing. The number of the remaining cells is measured. IC50 values are calculated.

αV/β6/αVβ8-LAP-TGF β1 Binding Assay

Integrins αVβ6/αVβ8 coupled beads are treated with an αVβ6/αVβ8 ligand (e.g., LAP TGF-β1 (LAP1)), and the complex is incubated with a primary antibody (Ab), which can be labeled for detection (e.g., fluorescently labeled), and optionally with a secondary antibody, which can be labeled for detection (e.g., fluorescently labeled). Reaction between integrin coupled beads and the ligand was considered as the full reaction, and reaction without the ligand or a compound of the disclosure was considered as the blank reaction. The complex is analyzed, e.g., by either plate reader or Flow Cytometer, to determine modulation of binding between αVβ6/αVβ8 and the ligand (e.g., LAP-TGF β1) by the compounds of the present disclsoure.

αVβ3/αVβ5-LAP-TGF β1 Binding Assay

Integrins αVβ3/αVβ5 coupled beads are treated with an αVβ3/αVβ5 ligand (e.g., vitronectin), and the complex is treated with a primary antibody (Ab), which can be labeled for detection (e.g., fluorescently labeled), and optionally with a secondary antibody, which can be labeled for detection (e.g., fluorescently labeled). Reaction between integrin coupled beads and the ligand was considered as the full reaction, and reaction without the ligand or a compound of the disclosure was considered as the blank reaction. The complex is analyzed, e.g., by either plate reader or Flow Cytometer, to determine modulation of binding between αVβ3/αVβ5 and the ligand (e.g., vitronectin) by the compounds of the present disclosure.

Anti-Angiogenic Activity Assay

The anti-angiogenic ability of the compound of formula I may be tested with methods or techniques known in the art, for example, the procedure described below.

Chick chorioallantoic membrane (CAM) is grafted with gelatin sponges impregnated with the test compounds and VEGF. Untreated CAM received only VEGF.

Albumin is removed from hen eggs and incubated. Grafts are placed on developing CAMs and further incubated. CAMs are then fixed, dissected and imaged for blood vessel growth.

Distribution in plasma, aqueous humor, vitreous humor, and retina of the compounds of the application, and the in vivo safety and efficacy of the compound of formula I may be tested using animals after administration of the compound to the animals.

Fibrosis can be generally recognized based on the distinct morphology of fibrous tissue in a biopsy of the organ in which fibrosis is suspected. Other means for detecting the presence of fibrosis or developing fibrosis include computerized axial tomography (CAT or CT) scan, ultrasound, magnetic resonance imaging (MRI), and monitoring the level of one or more serum markers known to be indicative of fibrosis (e.g., various types of collagens). The precise manner of diagnosing fibrosis also varies depending on the organ where the fibrotic process takes place. For instance, biopsies are generally effective for diagnosing fibrosis of most organs, whereas endoscopy involving a fiber optic instrument (e.g., a sigmoidoscope or a colonoscope) can be a less traumatic alternative to detect fibrosis of certain organs such as the intestine.

Biopsy for Detecting Fibrosis

Procedures for obtaining biopsy from a given organ or tissue are known, e.g., through exploratory surgery, or a biopsy needle. Upon obtaining a biopsy, the sample is examined and given a score to indicate the presence and level of fibrosis in the sample. Frequently used scoring systems include: the METAVIR scoring system, modified HAI (ISHAK) scoring system, and the Knodell scoring system. The criteria used in scoring are well established and known to those of skilled in the art.

Fibrosis Markers

There are numerous known serum markers whose level can be indicative of the presence and/or severity of fibrosis, including hyaluronic acid, laminin, undulin (type IV collagen) pro-peptides from types I, II, and IV collagens, lysyl oxidase, prolyl hydroxylase, lysyl hydroxylase, PIIINP, PICP, collagen VI, tenascin, collagen XIV, laminin P1, TIMP-1, MMP-2, α2 macroglobulin, haptoglobin, gamma glutamyl transpeptidase, γ globulin, total bilirubin, and apolipoprotein A1.

In vivo Bleomycin Induced Pulmonary Fibrosis Model.

Experimental animals are randomly and prospectively assigned to groups. On day 0 and prior to bleomycin induction, animals are administered the first dose of vehicle or a compound of the present disclosure. Following dosing, all animals are anesthetized. A small diameter cannula is inserted into the trachea and saline or bleomycin is slowly infused into the lungs. Group 1 serves as an untreated control group and receives saline only (no bleomycin) on day 0. The other groups receive bleomycin on day 0. Treatments with vehicle (e.g., methylcellulose), positive control (e.g., Pirfenidone), or a compound of the present disclosure are administered once or twice daily via oral gavage (PO). All animals are weighed and evaluated daily for respiratory distress.

Prior to sacrifice, animals are anesthetized and once the animal is determined to be non-responsive a shallow incision is made. The trachea is isolated and a transverse cut is made between tracheal rings approximately half-way through the trachea. A tracheotomy is performed by the insertion of a cannula through the incision secured with surgical suture to the trachea. Following cannulation, the adapter end of the cannula is attached to the mechanical ventilator. The animal is ventilated and following an acclimation period, lung volume is standardized and each animal undergoes a measure of total respiratory impedance.

Pharmaceutical Compositions

The present disclosure also relates to pharmaceutical compositions comprising a compound of the present disclosure as an active ingredient. In one aspect, the present disclosure provides a pharmaceutical composition comprising a compound of the present disclosure, or a pharmaceutically acceptable salt or solvate thereof and one or more pharmaceutically acceptable carriers or excipients. A compound of the present disclosure, or a pharmaceutically acceptable salt or solvate thereof can be either amorphous or crystalline. In some embodiments, a compound of the present disclosure is Compound Y. In some embodiments, the solvate is Compound Z.

As used herein, the term "composition" is intended to encompass a product comprising the specified ingredients in the specified amounts, as well as any product which results, directly or indirectly, from combination of the specified ingredients in the specified amounts.

A compound of the present disclosure, or a pharmaceutically acceptable salt or solvate thereof, can be formulated for oral administration in forms such as tablets, capsules (each of which includes sustained release or timed release formulations), pills, powders, granules, elixirs, tinctures, suspensions, syrups and emulsions. A compound of the present disclosure, or a pharmaceutically acceptable salt or solvate thereof can also be formulated for intravenous (bolus or in-fusion), intraperitoneal, topical (e.g., ocular eye-drop), subcutaneous, intramuscular or transdermal (e.g., patch) administration, all using forms well known to those of ordinary skill in the pharmaceutical arts. For example, a compound of the present disclosure, or a pharmaceutically acceptable salt or solvate thereof for the treatment of macular degeneration, DR, DME, or macular edema following RVO, are formulated for topical administration, for example, in the form of eye-drops.

For topical ocular administration, the compositions are provided as ophthalmic formulation comprising a compound of the present disclosure, or a pharmaceutically acceptable salt or solvate thereof in concentration between about 0.01 and about 5 weight percent.

The ophthalmic formulation of the present disclosure may be in the form of an aqueous solution comprising an aqueous vehicle. The aqueous vehicle component of the ophthalmic formulation may comprise water and at least one ophthalmically acceptable excipient. Preferably, the aqueous vehicle comprises a solution of the one or more ophthalmically acceptable excipients in water.

Suitable ophthalmically acceptable excipients include those selected from the group consisting of a solubility enhancing agent, chelating agent, preservative, tonicity agent, viscosity/suspending agent, buffer, and pH modifying agent, and a mixture thereof. Preferably, the ophthalmically acceptable excipient is selected from the group consisting of a solubility enhancing agent, chelating agent, preservative, tonicity agent, viscosity/suspending agent, and pH modifying agent, and a mixture thereof.

Any suitable ophthalmically acceptable solubility enhancing agent can be used. Examples of a solubility enhancing agent include cyclodextrin, such as those selected from the group consisting of hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-β-(trimethylammonio)propyl-β-cyclodextrin, glucosyl-β-cyclodextrin, sulphated β-cyclodextrin S-β-CD), maltosyl-β-cyclodextrin, β-cyclodextrin sulfobutyl ether, branched-β-cyclodextrin, hydroxypropyl-γ-cyclodextrin, randomly methylated-γ-cyclodextrin, and trimethyl-γ-cyclodextrin, and mixtures thereof. Preferably, solubility enhancing agent includes β-cyclodextrin sulfobutyl ether, hyrdoxypropyl-β-cyclodextrin, sulphated β-cyclodextrin (S-β-CD), and maltosyl-β-cyclodextrin, and mixtures thereof. β-cyclodextrin sulfobutyl ether is a particularly preferred solubility enhancing agent.

Any suitable ophthalmically acceptable chelating agent can be used. Examples of a suitable ophthalmically acceptable chelating agent include those selected from the group consisting of ethylenediaminetetraacetic acid and metal salts thereof, disodium edetate, trisodium edetate, and tetrasodium edetate, and mixtures thereof. Disodium edetate is a particularly preferred chelating agent.

Preferably, the aqueous vehicle includes a preservative. Preferred preservatives include those selected from the group consisting of quaternary ammonium salts such as benzalkonium halides (preferably benzalkonium chloride), chlorhexidine gluconate, benzethonium chloride, cetyl pyridinium chloride, benzyl bromide, phenylmercury nitrate, phenylmercury acetate, phenylmercury neodecanoate, merthiolate, methylparaben, propylparaben, sorbic acid, potassium sorbate, sodium benzoate, sodium propionate, ethyl p-hydroxybenzoate, propylaminopropyl biguanide, and butyl-p-hydroxybenzoate, sorbic acid, and mixtures thereof. More preferably, the preservative is a quaternary ammonium salt such as benzalkonium halides (preferably benzalkoniurn chloride), chlorhexidine gluconate, benzethonium chloride, cetyl pyridinium chloride, potassium sorbate, sodium benzoate, ethyl p-hydroxybenzoate, butyl p-hydroxybenzoate, or propylaminopropyl biguanide, or mixtures thereof. Propylaminopropyl biguanide is an especially preferred preservative.

The aqueous vehicle may also include a tonicity agent to adjust the tonicity (osmotic pressure) in order to achieve an ophthalmically compatible formulation. The tonicity agent can be selected from the group consisting of a glycol (such as propylene glycol, diethylene glycol, triethylene glycol), glycerol, dextrose, glycerin, mannitol, potassium chloride, and sodium chloride, and a mixture thereof. Preferably, the tonicity agent is selected from the group consisting of glycerin, mannitol, potassium chloride, and sodium chloride. More preferably mannitol and/or sodium chloride (and most preferably a mixture thereof) are employed.

The aqueous vehicle preferably also contains a viscosity/suspending agent. Suitable viscosity/suspending agents include those selected from the group consisting of cellulose derivatives, such as methyl cellulose, ethyl cellulose, hydroxyethylcellulose, polyethylene glycols (such as polyethylene glycol 300, polyethylene glycol 400), carboxymethyl cellulose, hydroxypropylmethyl cellulose, and cross-linked acrylic acid polymers (carbomers), such as polymers of acrylic acid cross-linked with polyalkenyl ethers or divinyl glycol (Carbopols—such as Carbopol 934, Carbopol 934P, Carbopol 971, Carbopol 974 and Carbopol 974P), and a mixture thereof. In preferred embodiments of the present disclosure, the viscosity/suspending agent is a carbomer, more preferably Carbopol 974P.

In order to adjust the formulation to an ophthalmically acceptable pH (typically a pH range of about 5.0 to about 9.0, more preferably about 5.5 to about 8.5, particularly about 6.0 to about 8.5, about 7.0 to about 8.5, about 7.2 to about 7.7, about 7.1 to about 7.9, or about 7.5 to about 8.0), the formulation may contain a pH modifying agent. The pH modifying agent is typically a mineral acid or metal hydroxide base, selected from the group of potassium hydroxide, sodium hydroxide, and hydrochloric acid, and mixtures thereof, and preferably sodium hydroxide and/or hydrochloric acid. These acidic and/or basic pH modifying agents are added to adjust the formulation to the target ophthalmically acceptable pH range. Hence it may not be necessary to use both acid and base—depending on the formulation, the addition of one of the acid or base may be sufficient to bring the mixture to the desired pH range.

The aqueous vehicle may also contain a buffering agent to stabilize the pH. When used, the buffer is selected from the group consisting of a phosphate buffer (such as sodium dihydrogen phosphate and disodium hydrogen phosphate), a borate buffer (such as boric acid, or salts thereof including disodium tetraborate), a citrate buffer (such as citric acid, or salts thereof including sodium citrate), and ε-aminocaproic acid, and mixtures thereof.

The ophthalmic formulation for topical administration to the eye may further comprise a wetting agent. In any embodiment of the present disclosure, the wetting agent is preferably a non-ionic wetting agent. More preferably, the wetting agent is water soluble or swellable. Most preferably the wetting agent is water soluble. "Water soluble" is to be understood in the manner used in standard texts such as the "Handbook of Pharmaceutical Excipients" (Raymond C Rowe, Paul J Sheskey and Sian C Owen, Fifth Edition, Pharmaceutical Press and American Pharmacists Association 2006). Suitable classes of wetting agents include those selected from the group consisting of polyoxypropylene-polyoxyethylene block copolymers (poloxamers), polyethoxylated ethers of castor oils, polyoxyethylenated sorbitan esters (polysorbates), polymers of oxyethylated octyl phenol (Tyloxapol), polyoxyl 40 stearate, fatty acid glycol esters, fatty acid glyceryl esters, sucrose fatty esters, and polyoxyethylene fatty esters, and mixtures thereof.

Specific examples of suitable wetting agents include those selected from the group consisting of: polyoxyethylene-polyoxypropylene block copolymers (poloxamers) such as: polyoxyethylene (160) polyoxypropylene (30) glycol [Pluronic F68], polyoxyethylene (42) polyoxypropylene (67) glycol [Pluronic P123], polyoxyethylene (54) polyoxypropylene (39) glycol [Pluronic P85], polyoxyethylene (196) polyoxypropylene (67) glycol [Poloxamer 407, Pluronic F127], polyoxyethylene (20) polyoxypropylene (20) glycol [Pluronic L44], polyoxyethylenated sorbitan esters (polysorbates) such as poly(oxyethylene)sorbitan monopalmitate (polysorbate 40), poly(oxyethylene)sorbitan monostearate (polysorbate 60), poly(oxyethylene)sorbitan tristearate (polysorbate 65), poly(oxyethylene) sorbitan monooleate (polysorbate 80), poly(oxyethylene) sorbitan monolaurate, poly(oxyethylene) sorbitan trioleate, polyethoxylated ethers of castor oils such as polyoxyethylene hydrogenated castor oil 10, polyoxyethylene hydrogenated castor oil 40, polyoxyethylene hydrogenated castor oil 50 and polyoxyethylene hydrogenated castor oil 60, polyoxyl 40 stearate, sucrose fatty esters, and polyoxyethylene fatty esters, and mixtures thereof.

Preferably, the wetting agent is selected from the group consisting of: polyoxyethylene-polyoxypropylene block copolymers (poloxamers) such as: polyoxyethylene (160) polyoxypropylene (30) glycol [Pluronic F68], polyoxyethylene (42) polyoxypropylene (67) glycol [Pluronic P123], polyoxyethylene (54) polyoxypropylene (39) glycol [Pluronic P85], polyoxyethylene (196) polyoxypropylene (67) glycol [Poloxamer 407, Pluronic F127], and polyoxyethylene (20) polyoxypropylene (20) glycol [Pluronic L44], polyoxyethylenated sorbitan esters (polysorbates) such as poly(oxyethylene)sorbitan monopalmitate (polysorbate 40), poly(oxyethylene)sorbitan monosteaxate (polysorbate 60), poly(oxyethylene)sorbitan tristearate (polysorbate 65), poly(oxyethylene) sorbitan monooleate (polysorbate 80), poly(oxyethylene) sorbitan monolaurate, and poly(oxyethylene) sorbitan trioleate and mixtures thereof.

More preferably, the wetting agent is a polyoxyethylene-polyoxypropylene block copolymer (poloxamer). Examples of suitable poloxamers include: polyoxyethylene (160) polyoxypropylene (30) glycol [Pluronic F68], polyoxyethylene (42) polyoxypropylene (67) glycol [Pluronic P123], polyoxyethylene (54) polyoxypropylene (39) glycol [Pluronic P85], polyoxyethylene (196) polyoxypropylene (67) glycol [Poloxamer 407, Pluronic F127] and polyoxyethylene (20) polyoxypropylene (20) glycol [Pluronic L44] or a mixture thereof.

Further preferred are wetting agents selected from the group consisting of polyoxyethylene (42) polyoxypropylene (67) glycol [Pluronic PI 23], polyoxyethylene (54) polyoxypropylene (39) glycol [Pluronic P85], polyoxyethylene (196) polyoxypropylene (67) glycol [Poloxamer 407, Pluronic F127] and mixtures thereof.

An especially preferred wetting agent is polyoxyethylene (196) polyoxypropylene (67) glycol [Poloxamer 407, Pluronic F127].

Particularly preferred formulations for topical administration to the eye of the present disclosure comprise a compound of the present disclosure, or a pharmaceutically acceptable salt or solvate thereof, a solubility enhancing agent, a cheating agent, a preservative, a tonicity agent, a viscosity/suspending agent, a buffer, and a pH modifying agent. More particularly preferred formulations are comprised of an aqueous solution of a β-cyclodextrin, a borate salt, boric acid, sodium chloride, disodium edetate, and propylaminopropyl biguanide.

The ophthalmic formulation of the present disclosure may also be in the form of a gel or a semi-gel, or both; a jelly; a suspension; an emulsion; an oil; an ointment; a cream; or a spray.

The ophthalmic gel, semi-gel, jelly, suspension, emulsion, oil, ointment, cream, or spray may contain various additives incorporated ordinarily, such as buffering agents (e.g., phosphate buffers, borate buffers, citrate buffers, tartrate buffers, acetate buffers, amino acids, sodium acetate, sodium citrate and the like), tonicity agents (e.g., saccharides such as sorbitol, glucose and mannitol, polyhydric alcohols such as glycerin, concentrated glycerin, PEG and propylene glycol, salts such as sodium chloride), preservatives or antiseptics (e.g., benzalkonium chloride, benzalkonium chloride, P-oxybenzoates such as methyl p-oxybenzoate or ethyl p-oxybenzoate, benzyl alcohol, phenethyl alcohol, sorbic acid or its salt, thimerosal, chlorobutanol and the like), solubilizing enhancing agents (e.g., cyclodextrins and their derivative, water-soluble polymers such as polyvinyl pyrrolidone, surfactants such as tyloxapol, polysorbates), pH modifiers (e.g., hydrochloric acid, acetic acid, phosphoric acid, sodium hydroxide, potassium hydroxide, ammonium hydroxide and the like), thickening agents (e.g., HEC, hydroxypropyl cellulose, methyl cellulose, HPMC, carboxymethyl cellulose and their salts), chelating agents (e.g., sodium edetate, sodium citrate, condensed sodium phosphate) and the like. Each of these additives may be in the amount or concentration similar to those described for the ophthalmic formulation in the form of a solution above.

Furthermore, a compound of the present disclosure, or a pharmaceutically acceptable salt or solvate thereof may be formulated for topical administration by incorporation into novel ophthamlic formulations including but not limited to: microemulsions, liposomes, niosomes, gels, hydrogel, nanoparticles, and nanosuspension.

1. Microemulsions

Microemulsions are dispersion of water and oil facilitated by a combination of surfactant and cosurfactant in a manner to reduce interfacial tension. These systems are usually characterized by higher thermodynamic stability, small droplet size (approximately 100 nm) and clear appearance. Their transparent appearance is due to the high level of dispersion of the internal phase, and the size of it ranges from 100-1000 angstroms. Processes for forming microemulsions suitable for use in ophthalmic formulations are described in Vandamne, T. F. Prog Retinal Eye Res 2002; 21:15-34, which is incorporated by reference.

2. Liposomes

Liposomes are lipid vesicles containing aqueous core and have been widely exploited in ocular delivery for various drug substances. Depending on the nature of the lipid composition selected, liposomes can provide extended release of the drug.

3. Niosomes

Niosomes are bilayered structural vesicles made up of nonionic surfactant and are capable of encapsulating both lipophilic and hydrophilic compounds. They can release the drug independent of pH and enhance ocular bioavailability. Niosomes are microscopic lamellar structures that are formed on the admixture of nonionic surfactant of the alkyl or dialkyl polyglycerol ether class and cholesterol with subsequent hydration in aqueous media. Structurally niosomes are similar to liposomes, in that they are also made up of a bilayer. However, the bilayer in the case of nisomes is made up of nonionic surface-active agents rather than phospholipids as in the case of liposomes. Niosomes may be unilamellar or multilamellar depending on the method used to prepare them. They are capable of entrapping hydrophilic and hydrophobic solutes. They possess great stability and lack many disadvantages associate with liposomes such as high cost and the variable purity of phospholipids. The properties of niosomes and process for preparing them are well known in the art, see e.g., Wagh, V. D. et al., *J Pharm Res* 2010; 3(7):1558-1563; Kaur, H. et al., *Int J Pharin Sci Rev Res* 2012; 15(1):113-120, each of which is incorporated by reference.

4. Gels

Ophthalmic gels are composed of mucoadhesive polymers that provide localized delivery of an active ingredient to the eye. Such polymers have a property known as bioadhesion, meaning attachment of a drug carrier to a specific biological tissue. These polymers are able to extend the contact time of the drug with the biological tissues and thereby improve ocular bioavailability. The choice of the polymer plays a critical role in the release kinetics of the drug from the dosage form. Several bioadhesive polymers are available with varying degree of mucoadhesive performance. Some examples are carboxymethylcellulose, carbopol, polycarbophil, and sodium alginate. The use of gel formulations in ocular drug deliver has been reviewed in Ali, Y. et al., *Adv Drug Deliv Rev* 2006; 58: 1258-1268, which is incorporated by reference.

5. Hydrogels

Hydrogels are three-dimensional, hydrophilic, polymeric networks capable of taking in large amounts of water or biological fluids. Residence time can be significantly enhanced with a hydrogel formulation. The gelation can be obtained by changing temperature and pH. Poloxamers, the most widely used polymer, contains the hydrophobic part in the center surrounded by a hydrophilic part. Though they are widely employed to enhance the residence time. Recent perspectives in the use of hydrogels in ocular drug deliver are described by Gaudana, R., Jwala, J., Boddu, S. H. S., Mitra, A. K. *Pharm Res.* 2009; 26(5):1197-1216 which is incorporated by reference.

6. Nanoparticles

Nanoparticles are defined as particles with a diameter of less than 1 μm, comprising of various biodegradable or non biodegradable polymers, lipids, phospholipids or metals. They can be classified as nanospheres or nanocapsules depending upon whether the drug has been uniformly dispersed or coated within polymeric material. The uptake and distribution of nanoparticles is dependent on their size. The use of nanoparticles in ocular drug delivery has recently been reviewed by Hing et al., *Int. J. Ophthalmol* 2013; 6:390-396, which is incorporated by reference.

7. Nanosuspensions

Nanosuspensions are defined as sub-micron colloidal systems that consist of poorly water soluble drugs suspended in an appropriate dispersion medium stabilized by surfactants. Usually, nanosuspensions consist of colloidal carriers like polymeric resins which are inert in nature. Nanosuspensions enhance drug solubility and thus bioavailability. Unlike microemulsions, nanosuspensions are non-irritant. Charge on the surface of nanoparticles facilitates their adhesion to the cornea. The use of nanosuspensions in drug delivery is reviewed in Rabinow, *Nature Rev Drug Disc* 2004; 785-796, which is incorporated by reference.

A compound of the present disclosure, or a pharmaceutically acceptable salt or solvate thereof can also be administered in the form of a formulation suitable for ocular topical delivery. Detailed descriptions of formulation suitable for ocular topical delivery are described in Bartlett, J. D. and Jaanus, S. D., *Clinical Ocular Pharmacology*, 2008, Elsevier Health Sciences, which is incorporated by reference.

A compound of the present disclosure, or a pharmaceutically acceptable salt or solvate thereof may also be coupled with soluble polymers as targetable drug carriers. Such polymers can include polyvinylpyrrolidone, pyran copolymer, polyhydroxypropylmethacrylamide-phenol, polyhydroxyethylaspartamide-phenol, and polyethyleneoxide-polylysine substituted with palmitoyl residues. Furthermore, the compounds of the present disclosure may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The present disclosure also provides a pharmaceutical composition comprising a compound of the present disclosure or a pharmaceutically acceptable salt or solvate thereof, and a pharmaceutically acceptable carrier or excipient, and further an active ingredient selected from the group consisting of a) an antagonist of integrin $\alpha 5\beta 1$, b) a cytotoxic/antiproliferative agent, c) an inhibitor of epidermal-derived, fibroblast-derived, or platelet-derived growth factor, d) an inhibitor of VEGF, e) an inhibitor of Flk-1/KDR, Flt-1, Tck/Tie-2, or Tic-1, and f) an inhibitor of phosphoinositide 3-kinase, and a mixture thereof.

The present disclosure further provides a pharmaceutical composition comprising a compound of the present disclosure or a pharmaceutically acceptable salt or solvate thereof, and a pharmaceutically acceptable carrier or excipient, and further an active ingredient selected from the group consisting of a) an antagonist of integrin $\alpha 5\beta 1$, b) a cytotoxic/antiproliferative agent, c) an inhibitor of epidermal-derived, fibroblast-derived, or platelet-derived growth factors, d) an inhibitor of VEGF, and e) an inhibitor of phosphoinositide 3-kinase, and a mixture thereof.

Non-limiting examples of antagonists of integrin $\alpha 5\beta 1$ are (S)-2-((R)-2-((S)-2-((S)-2-((S)-1-acetylpyrrolidine-2-carboxamido)-3-(1H-imidazol-5-yl)propanamido)-3-hydroxypropanamido)-3-mercaptopropanamido)succinamide, and JSM6427.

Non-limiting examples of cytotoxic/antiproliferative agents are taxol, vincristine, vinblastine, and doxorubicin.

Non-limiting examples of inhibitors of epidermal-derived, fibroblast-derived, or platelet-derived growth factors are pazopanib, and sunitinib, Non-limiting examples of inhibitors of vascular endothelial derived growth factor (VEGF) are bevacizumab and ranibizumab, Non-limiting examples of inhibitors of phosphoinositide 3-kinase are indelalisib and 2-morpholin-4-yl-8-phenylchroman-4-one.

Methods of Use

"Fibrosis" refers to a condition involving the development of excessive fibrous connective tissue, e.g., scar tissue, in a tissue or organ. Such generation of scar tissue may occur in response to infection, inflammation, or injury of the organ due to a disease, trauma, chemical toxicity, and so on. Fibrosis may develop in a variety of different tissues and organs, including the liver, kidney, intestine, lung, heart, etc.

Fibrosis of organs or tissues is involved in various diseases or disorders, such as (1) renal diseases (e.g., tubulointerstitial nephritis), (2) respiratory diseases (e.g., interstitial pneumonia (pulmonary fibrosis)), (3) gastrointestinal diseases (e.g., hepatocirrhosis, chronic pancreatitis and scirrhous gastric cancer), (4) cardiovascular diseases (myocardial fibrosis), (5) bone and articular diseases (e.g., bone marrow fibrosis and rheumatoid arthritis), (6) skin diseases (e.g., post surgical scar, burn scar, keloid, hypertrophic scar and scleroderma), (7) obstetric diseases (e.g., hysteromyoma), (8) urologic diseases (prostatic hypertrophy), (9) other diseases (e.g., Alzheimer's disease, sclerosing peritonitis, type I diabetes and post surgical adhesion). Accordingly, the tissue fibrosis may be cardiac fibrosis, scleroderma, skeletal muscle fibrosis, hepatic fibrosis, kidney fibrosis, pulmonary fibrosis, intestinal fibrosis, or diabetic fibrosis. For example, a fibrosis may be ongenital hepatic fibrosis (CHF); renal tubulointerstitial fibrosis; pulmonary fibrosis associated with an autoimmune disorder (e.g., rheumatoid arthritis, lupus and sarcoidosis); interstitial fibrosis associated with diabetic cardiomyopathy; skeletal muscle fibrosis associated with muscular dystrophies (e.g., Becker muscular dystrophy and Duchenne muscular dystrophy), denervation atrophies, neuromuscular diseases (e.g., acute polyneuritis, poliomyelitis, Werdig/Hoffman disease, amyotrophic lateral sclerosis, progressive bulbar atrophy disease), Mediastinal fibrosis (soft tissue of the mediastinum), myelofibrosis (bone marrow), retroperitoneal fibrosis (soft tissue of the retroperitoneum), progressive massive fibrosis (lungs), nephrogenic systemic fibrosis (skin), Crohn's Disease (intestine), Keloid (skin), scleroderma/systemic sclerosis (skin, lungs), arthrofibrosis (knee, shoulder, other joints), Peyronie's disease (penis), dupuytren's contracture (hands or fingers), Some forms of adhesive capsulitis (shoulder).

"Hepatic fibrosis" or "fibrosis of the liver" is the excessive accumulation of extracellular matrix proteins including collagen that occurs in most types of chronic liver diseases. Advanced liver fibrosis results in cirrhosis, liver failure, and portal hypertension and often requires liver transplantation. Activated hepatic stellate cells, portal fibroblasts, and myofibroblasts of bone marrow origin have been identified as major collagen-producing cells in the injured liver. These cells are activated by fibrogenic cytokines such as TGF-01, angiotensin II, and leptin. The main causes of liver fibrosis in industrialized countries include chronic alcohol abuse, nonalcoholic steatohepatitis (NASH), iron and copper overload, alcohol-induced liver injury, chronic infection of hepatitis C, B, and D, hemochromatosis, secondary biliary cirrhosis, NASH, and autoimmune hepatitis.

"Pulmonary fibrosis" or "fibrosis of the lung" is a respiratory disease in which scars are formed in the lung tissues, leading to serious breathing problems. The accumulation of excess fibrous connective tissue leads to thickening of the walls, and causes reduced oxygen supply in the blood. As a consequence patients suffer from perpetual shortness of breath. Pulmonary fibrosis may be a secondary effect of other diseases. Most of these are classified as interstitial lung diseases. Examples include autoimmune disorders, viral infections and bacterial infection like tuberculosis which may cause fibrotic changes in both lungs upper or lower lobes and other microscopic injuries to the lung. Idiopathic pulmonary fibrosis can also appear without any known cause. Diseases and conditions that may cause pulmonary fibrosis as a secondary effect include: inhalation of environmental and occupational pollutants, hypersensitivity pneumonitis, cigarette smoking, some typical connective tissue diseases (such as rheumatoid arthritis, SLE and scleroderma), other diseases that involve connective tissue (such as sarcoidosis and Wegener's granulomatosis), infections, and certain medications (e.g., amiodarone, bleomycin (pingyangmycin), busulfan, methotrexate, apomorphine, and nitrofurantoin).

"Cardiac fibrosis" or "fibrosis of the heart" may refer to an abnormal thickening of the heart valves due to inappropriate proliferation of cardiac fibroblasts, but more commonly refers to the proliferation of fibroblasts in the cardiac muscle. Fibrotic cardiac muscle is stiffer and less compliant and is seen in the progression to heart failure. Fibrocyte cells normally secrete collagen, and function to provide structural support for the heart. When over-activated this process causes thickening and fibrosis of the valve, with white tissue building up primarily on the tricuspid valve, but also occurring on the pulmonary valve. The thickening and loss of flexibility eventually may lead to valvular dysfunction and right-sided heart failure.

"Renal fibrosis" or "fibrosis of the kidney", characterized by glomerulosclerosis and tubulointerstitial fibrosis, is the final common manifestation of a wide variety of chronic kidney diseases (CKD). Progressive CKD often results in widespread tissue scarring that leads to the complete destruction of kidney parenchyma and end-stage renal failure.

Cystic fibrosis (CF) is a genetic disorder that affects mostly the lungs but also the pancreas, liver, kidneys and intestine. Patients experience symptoms including difficulty breathing and coughing up sputum as a result of frequent lung infections. CF is an autosomal recessive disorder, caused by mutations in both copies of the gene for the protein cystic fibrosis transmembrane conductance regulator (CFTR). CFTR is involved in production of sweat, digestive fluids, and mucus.

A compound of the present disclosure modulates (e.g., inhibits the activity of, decreases the expression of, and/or increases the degradation of) a factor (e.g., collagen, TGF-$\beta$1) that is involved in the regulation of the fibrosis process. For example, a compound of the present disclosure, or a pharmaceutically acceptable salt or solvate thereof is capable of reducing collagen synthesis. In another example, a compound of the present disclosure, or a pharmaceutically acceptable salt or solvate thereof can decrease the production of fibrogenic cytokines (e.g., TGF-$\beta$1). In another example, a compound of the present disclosure, or a pharmaceutically acceptable salt or solvate thereof can reduce the accumulation of extracellular matrix protein. In yet another example, a compound of the present disclosure, or a pharmaceutically acceptable salt or solvate thereof can inhibit the proliferation of fibroblast cells.

In another example, a compound of the present disclosure, or a pharmaceutically acceptable salt or solvate thereof may inhibit processes mediated by $\alpha$v integrins. Inhibition and blockade of $\alpha$v$\beta$6 and/or $\alpha$v$\beta$8 result in a phenotype similar to all of the development effects of loss of TGF-$\beta$1 and TFG-$\beta$3, suggesting that these integrins are required for most or all important roles of these TGF-$\beta$ isoforms in development of fibrosis. Antagonists of the integrins $\alpha$v$\beta$6 and/or $\alpha$v$\beta$8 are thus useful for treating and preventing fibrotic activity. For example, TGF-$\beta$ activation by the $\alpha$v$\beta$6 integrin has been shown to play an important role in models of fibrosis in the lungs, biliary tract, and kidney. The $\alpha$v$\beta$6 integrin has further been shown to be overexpressed in human kidney epithelium in membranous glomerulonephritis, diabetes mellitus, IgA nephropathy, Goodpasture's syndrome, and Alport syndrome renal epithelium. In one aspect, Compound Y, or a pharmaceutically acceptable salt or solvate thereof treats or prevents fibrosis by inhibiting $\alpha$v$\beta$6 and/or $\alpha$v$\beta$8.

Over expression of the $\alpha$v$\beta$6 integrin has also been shown to play a role in certain cancers, including but not limited to colorectal carcinomas, thyroid carcinomas, cervical squamous cell carcinomas, and certain breast carcinomas. Over expression of the $\alpha$v$\beta$8 integrin has been associated with a variety of Th17-drive autoimmune diseases, including psoriasis, multiple sclerosis, rheumatoid arthritis, and inflammatory bowel disease. A number of integrin receptors have also been shown to play a role in foot and mouth disease virus (FMDV).

Thus, in one aspect, the present disclosure provides a method of treating or preventing a fibrosis, comprising administering to a subject in need thereof a therapeutically effective amount of a compound of the present disclosure or a pharmaceutically acceptable salt or solvate thereof or a therapeutically effective amount of a pharmaceutical composition of the present disclosure. In one aspect, the present disclosure provides treating a fibrosis. In one aspect, the present disclosure provides preventing a fibrosis. In some embodiments, a compound of the present disclosure is Compound Y. In some embodiments, the solvate is Compound Z.

In another aspect, the present disclosure also provides the use of a compound of the present disclosure or a pharmaceutically acceptable salt or solvate thereof in the manufacture of a medicament for the treatment or prevention of a fibrosis in a subject. The present application also provides the use of a compound of the present disclosure or a pharmaceutically acceptable salt or solvate thereof in treating or preventing a fibrosis in a subject.

In one aspect, the fibrosis is fibrosis of the liver, kidney, intestine, lung, or heart. In a further aspect, the fibrosis is involved in various diseases or disorders, such as (1) renal diseases (e.g., tubulointerstitial nephritis), (2) respiratory diseases (e.g., interstitial pneumonia (pulmonary fibrosis)), (3) gastrointestinal diseases (e.g., hepatocirrhosis, chronic pancreatitis and scirrhous gastric cancer), (4) cardiovascular diseases (myocardial fibrosis), (5) bone and articular diseases (e.g., bone marrow fibrosis and rheumatoid arthritis), (6) skin diseases (e.g., post surgical scar, burn scar, keloid, hypertrophic scar and scleroderma), (7) obstetric diseases (e.g., hysteromyoma), (8) urologic diseases (prostatic hypertrophy), (9) other diseases (e.g., Alzheimer's disease, sclerosing peritonitis, type I diabetes and post surgical adhesion).

Diabetic retinopathy, a closely related condition, is the result of microvascular retinal changes. Hyperglycemia-induced intramural pericyte death and thickening of the basement membrane lead to incompetence of the vascular walls in the retina, which affects the blood-retinal barrier and makes the retinal blood vessels more permeable. Damaged blood vessels leak fluid and lipids onto the macula, the part of the retina that provides us with detailed vision, causing the macula to swell. Eventually this can progress to develop a condition called macular edema.

Accordingly, AMD, DR, DME, and macular edema following central retinal vein occlusion (thrombosis) can be treated or prevented through administration (e.g., topical administration) of Compound Y, or a pharmaceutically acceptable salt or solvate thereof or pharmaceutical compositions of the present disclosure.

The present disclosure provides a method of treating or preventing a disease or condition in a subject, comprising administering to a subject in need thereof a therapeutically effective amount of Compound Y or a pharmaceutically acceptable salt or solvate thereof or a therapeutically effective amount of a pharmaceutical composition of the disclosure. In one aspect, the present disclosure provides treating a disease or condition. In one aspect, the present disclosure provides preventing a disease or condition.

In one aspect, the compound or pharmaceutical composition of the present disclosure is administered topically. In a further aspect, the compound or pharmaceutical composition of the present disclosure is administered as an ophthalmic solution. In another aspect, the compound or pharmaceutical composition of the present disclosure is administered as an ophthalmic emulsion, suspension, gel, or semi-gel. In another aspect, the compound or pharmaceutical composition of the present disclosure is administered as an ophthalmic jelly, oil, ointment, cream, or spray.

The compounds or pharmaceutical compositions of the present disclosure are administered in dosages effective to inhibit the function of $\alpha v\beta 3$, $\alpha v\beta 5$, $\alpha v\beta 6$ and/or $\alpha v\beta 8$ integrins and thus treat or prevent a disease condition mediated by the $\alpha v\beta 3$, $\alpha v\beta 5$, $\alpha v\beta 6$ and/or $\alpha v\beta 8$ integrin.

The present disclosure provides a method of treating or preventing a disease or condition mediated by an $\alpha v$ integrin in a subject, comprising administering to a subject in need thereof a therapeutically effective amount of a compound of the present disclosure or a pharmaceutically acceptable salt or solvate thereof or a therapeutically effective amount of a pharmaceutical composition of the present disclosure. In one aspect, the disease or condition is a disease or condition in which angiogenesis is involved. In a further aspect, the disease or condition is a disease or condition in which ocular angiogenesis is involved. The present disclosure also provides a method of treating or preventing an $\alpha v\beta 3$, $\alpha v\beta 5$, $\alpha v\beta 6$ and/or $\alpha v\beta 8$ integrin-mediated disease or condition in a subject, comprising administering to a subject in need thereof a therapeutically effective amount of a compound of the present disclosure or a pharmaceutically acceptable salt or solvate thereof or a therapeutically effective amount of a pharmaceutical composition of the present disclosure. In one aspect, the disease or condition is a disease or condition in which ocular angiogenesis is involved. In one aspect, the disease or condition is macular degeneration. In one aspect, the disease or condition is age-related macular degeneration (AMD). In one aspect, the disease or condition is diabetic retinopathy (DR). In one aspect, the disease or condition is diabetic macular edema (DME). In one aspect, the disease or condition is macular edema following retinal vein occlusion (RVO). In one aspect, the condition is fibrosis of the liver, kidney, intestine, lung, and heart. In one aspect, the disease is a renal disease, a respiratory disease, a gastrointestinal disease, a cardiovascular disease, a bone and articular disease, a skin disease, an obstetric disease, or a urologic disease.

The present disclosure also provides a method of treating or preventing an $\alpha v\beta 3$ and/or $\alpha v\beta 5$ integrin-mediated disease or condition in a subject, comprising administering to a subject in need thereof a therapeutically effective amount of a compound of the present disclosure or a pharmaceutically acceptable salt or solvate thereof or a therapeutically effective amount of a pharmaceutical composition of the present disclosure. In one aspect, the disease or condition is a disease or condition in which ocular angiogenesis is involved. In one aspect, the disease or condition is macular degeneration. In one aspect, the disease or condition is age-related macular degeneration (AMD). In one aspect, the disease or condition is diabetic retinopathy (DR). In one aspect, the disease or condition is diabetic macular edema (DME). In one aspect, the disease or condition is macular edema following retinal vein occlusion (RVO).

The present disclosure provides the use of a compound of the present disclosure or a pharmaceutically acceptable salt or solvate thereof in the manufacture of a medicament for the treatment or prevention of a disease or condition in a subject. The present disclosure provides the use of a compound of the present disclosure or a pharmaceutically acceptable salt or solvate thereof in treating or preventing a disease or condition in a subject.

The present disclosure provides the use of a compound of the present disclosure or a pharmaceutically acceptable salt or solvate thereof in the manufacture of a medicament for the treatment or prevention of a disease or condition mediated by an $\alpha v$ integrin in a subject. The present disclosure provides the use of a compound of the present disclosure or a pharmaceutically acceptable salt or solvate thereof in treating or preventing a disease or condition mediated by an $\alpha v$ integrin in a subject. In one aspect, the disease or condition is a disease or condition in which angiogenesis is involved. In a further aspect, the disease or condition is a disease or condition in which ocular angiogenesis is involved.

The present disclosure also provides the use of a compound of the present disclosure or a pharmaceutically acceptable salt or solvate thereof in the manufacture of a medicament for the treatment or prevention of an $\alpha v\beta 3$, $\alpha v\beta 5$, $\alpha v\beta 6$ and/or $\alpha v\beta 8$ integrin-mediated disease or condition in a subject. The present disclosure provides the use of a compound of the present disclosure or a pharmaceutically acceptable salt or solvate thereof in treating or preventing of an $\alpha v\beta 3$, $\alpha v\beta 5$, $\alpha v\beta 6$ and/or $\alpha v\beta 8$ integrin-mediated disease or condition in a subject. In one aspect, the disease or condition is a disease or condition in which ocular angiogenesis is involved. In one aspect, the disease or condition is macular degeneration. In one aspect, the disease or condition is age-related macular degeneration (AMD). In one aspect, the disease or condition is diabetic retinopathy (DR). In one aspect, the disease or condition is diabetic macular edema (DME). In one aspect, the disease or condition is macular edema following retinal vein occlusion (RVO). In one aspect, the condition is fibrosis of the liver, kidney, intestine, lung, and heart. In one aspect, the disease is a renal disease, a respiratory disease, a gastrointestinal disease, a cardiovascular disease, a bone and articular disease, a skin disease, an obstetric disease, or a urologic disease.

The present disclosure provides a compound of the present disclosure or a pharmaceutically acceptable salt or solvate thereof for use in treating or preventing a disease or condition mediated by an $\alpha v$ integrin in a subject. In one aspect, the disease or condition is a disease or condition in which angiogenesis is involved. In a further aspect, the disease or condition is a disease or condition in which ocular angiogenesis is involved.

The present disclosure also provides a compound of the present disclosure or a pharmaceutically acceptable salt or solvate thereof for use in treating or preventing of an $\alpha v\beta 3$, $\alpha v\beta 5$, $\alpha v\beta 6$ and/or $\alpha v\beta 8$ integrin-mediated disease or condition in a subject. In one aspect, the disease or condition is a disease or condition in which ocular angiogenesis is involved. In one aspect, the disease or condition is macular degeneration. In one aspect, the disease or condition is age-related macular degeneration (AMD). In one aspect, the disease or condition is diabetic retinopathy (DR). In one aspect, the disease or condition is diabetic macular edema (DME). In one aspect, the disease or condition is macular edema following retinal vein occlusion (RVO). In one aspect, the condition is fibrosis of the liver, kidney, intestine, lung, and heart. In one aspect, the disease is a renal disease, a respiratory disease, a gastrointestinal disease, a cardiovascular disease, a bone and articular disease, a skin disease, an obstetric disease, or a urologic disease.

Administration of the second therapy in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations of the present disclosure. "Combination therapy" is intended to embrace administration of these therapeutic agents in a sequential manner, wherein each therapeutic agent is administered at a different time, as well as administration of these therapeutic agents, or at least two of the therapeutic agents, in a substantially simultaneous manner.

In accordance with the method of the present disclosure, the individual components of the combination can be administered separately at different times during the course of therapy or concurrently in divided or single combination forms. The instant disclosure is therefore to be understood as embracing all such regimens of simultaneous or alternating treatment, and the term "administering" is to be interpreted accordingly. It will be understood that the scope of combinations of a compound of the present disclosure or a pharmaceutically acceptable salt or solvate thereof with other agents useful for treating αv integrin-mediated conditions includes in principle any combination with any pharmaceutical composition useful for treating fibrosis, macular degeneration, DR, DME, or macular edema following RVO. When the method of the present disclosure is a combination treatment of a formulation of the present disclosure topically administered to the eyes and an anti-VEGF protein or aptamer, the procedures, dosages and frequencies of the anti-VEGF protein or aptamer are as described in the package inserts for those agents.

The dosage regimen utilizing a compound of the present disclosure, or a pharmaceutically acceptable salt or solvate thereof is selected in accordance with a variety of factors including type, species, age, weight, sex and medical condition of the patient; the severity of the condition to be treated; and the particular compound or salt thereof employed. An ordinary skilled physician, veterinarian or clinician can readily determine and prescribe the effective amount of the drug required to prevent, counter or arrest the progress of the condition.

In the methods of the present disclosure, the compounds herein described in detail can form the active ingredient, and are typically administered in admixture with suitable pharmaceutical diluents, excipients or carriers (collectively referred to herein as "carrier") suitably selected with respect to the intended topical administration to the eye and consistent with conventional pharmaceutical practices.

For purposes of the present disclosure, the following definitions will be used (unless expressly stated otherwise):

"Alkyl" refers to a saturated straight or branched hydrocarbon chain radical consisting solely of carbon and hydrogen atoms having from one to twelve carbon atoms ($C_1$-$C_{12}$ alkyl), one to eight carbon atoms ($C_1$-$C_8$ alkyl), or one to six carbon atoms ($C_1$-$C_6$ alkyl), e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

The term "cycloalkyl" as used herein refers to a monocyclic saturated carbon ring, wherein the number of ring atoms is indicated by a range of numbers. In exemplary embodiments, "cycloalkyl" refers to a carbon ring as defined above containing 3, 4, 5, 6, 7, or 8 ring atoms (i.e., C3-C8 cycloalkyl). Examples of a cycloalkyl group include, but are not limited to, cyclopropyl, cyclobutyl, cyclopentyl, cyclohexyl, cycloheptyl, and cyclooctyl.

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms. Unless stated otherwise specifically in the specification, an alkenyl group may be optionally substituted.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms. Unless stated otherwise specifically in the specification, an alkynyl group may be optionally substituted.

The term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, -halogen, —O—$C_1$-$C_6$alkyl, —$C_1$-$C_6$alkyl, —$OC_2$-$C_6$alkenyl, —$OC_2$-$C_6$alkynyl, —$C_2$-$C_6$alkenyl, —$C_2$-$C_6$alkynyl, —OH, —OP(O)(OH)$_2$, —OC(O)$C_1$-$C_6$alkyl, —C(O)$C_1$-$C_6$alkyl, —OC(O)O$C_1$-$C_6$alkyl, —NH$_2$, —NH($C_1$-$C_6$alkyl), —N($C_1$-$C_6$alkyl)$_2$, —S(O)$_2$—$C_1$-$C_6$alkyl, —S(O)NH$C_1$-$C_6$alkyl, and —S(O)N($C_1$-$C_6$alkyl)$_2$. The substituents can themselves be optionally substituted. Furthermore when containing two fused rings the aryl groups herein defined may have an unsaturated or partially saturated ring fused with a fully saturated ring. Exemplary ring systems of these aryl groups include indanyl, indenyl, tetrahydronaphthalenyl, and tetrahydrobenzoannulenyl.

The term "heteroaryl" as used herein refers to a cyclic hydrocarbon, where at least one of the ring atoms is an O, N, or S, the ring is characterized by delocalized π electrons (aromaticity) shared among the ring members, and wherein the number of ring atoms is indicated by a range of numbers. Heteroaryl moieties as defined herein have C or N bonding hands through which the heteroaryl ring is connected to an adjacent moiety. For example, in some embodiments, a ring N atom from the heteroaryl is the bonding atom of the heteroaryl moiety. In exemplary embodiments, "heteroaryl" refers to a cyclic hydrocarbon as described above containing 5 or 6 ring atoms (i.e., $C_5$-$C_6$ heteroaryl). Examples of a heteroaryl group include, but are not limited to, pyrrole, furan, thiene, oxazole, thiazole, isoxazole, isothiazole, imidazole, pyrazole, oxadiazole, thiadiazole, triazole, tetrazole, pyridine, pyrimidine, pyrazine, pyridazine, and triazine.

The term "alkoxy," as used herein, refers to straight chain or branched alkoxides of the number of carbon atoms specified (e.g., $C_1$-$C_4$ alkoxy), or any number within this range (methoxy, ethoxy, propoxy, i-propoxy, butoxy, i-butoxy, t-butoxy, etc.).

"Carbocyclic ring" refers to saturated cycloalkyl of the number of carbon atoms specified (i.e., $C_3$ or $C_4$), such as cyclopropyl and cyclobutyl.

The term "heterocyclyl," or "heterocycloalkyl," as used herein, refers to a non-aromatic 3-, 4-, 5-, 6- or 7-membered ring or a bi- or tri-cyclic group fused of non-fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, and (iv) the nitrogen heteroatom may optionally be quaternized. Representative heterocycloalkyl groups include, but are not limited to, [1,3]dioxolane, pyrrolidinyl, pyrazolinyl, pyrazolidinyl, imidazolinyl, imidazolidinyl, benzimidazolyl, piperidinyl, piperazinyl, oxazolidinyl, isoxazolidinyl, morpholinyl, thiazolidinyl, isothiazolidinyl, and tetrahydrofuryl.

The term "substituted," as used herein, means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

"Protic solvent" refers to a solvent or solvent mixtures that is capable of functioning as an acid for purposes of protonating any unreacted, strongly basic reaction intermediates. Non-limiting examples of protic solvents include water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, glycerol, and the like.

"Aprotic solvent" refers to an organic solvent that lacks an acidic hydrogen. Aprotic solvents cannot donate hydrogen, and generally have high dielectric constants and high polarity. An aprotic solvent can be either polar or nonpolar. Non-limiting examples of aprotic solvents include ether solvents, acetone, acetonitrile, benzene, diethoxymethane, N,N-dimethylformamide (DMF), dimethyl sulfoxide (DMSO), N,N-dimethylpropionamide, 1,3-dimethyl-3,4,5, 6-tetrahydro-2(1H)-pyrimidinone (DMPU), 1,3-dimethyl-2-imidazolidinone (DMI), 1,2-dimethoxyethane (DME), N,N-dimethylacetamide (DMAC), N-methylpyrrolidinone (NMP), ethyl acetate, ethyl formate, ethyl methyl ketone, formamide, hexamethylphosphoramide, methyl acetate, N-methylacetamide, N-methylformamide, methylene chloride, nitrobenzene, nitromethane, propionitrile, sulfolane, tetramethylurea, tetrahydrofuran (THF), toluene, and trichloromethane.

"Base" refers to a substance whose molecule or ion can combine with a proton (hydrogen ion), or a substance capable of donating a pair of electrons (to an acid) for the formation of a coordinate covalent bond. A base can be inorganic or organic. Examples of base include, but are not limited to, sodium hydroxide, sodium hydride, potassium hydroxide, potassium hydride, ammonia, 1,8-diazabicyclo [5.4.0]undec-7-ene (DBU), and 4-dimethylaminopyridine (DMAP), sodium hexamethyldisilazane (NaHMDS), potassium hexamethyldisilazane (KHMDS), sodium tert-butoxide (NaO$^t$Bu), potassium tert-butoxide (KO$^t$Bu), calcium hydroxide, sodium methoxide, sodium ethoxide, sodium tert-butoxide, and a mixture thereof.

A "non-nucleophilic base" refers to a base that is capable of abstracting an acidic hydrogen, e.g., from an —OH or —NH—moiety, but does not readily take part in a nucleophilic substitution reaction. Examples of non-nucleophilic bases include, but are not limited to, N,N-diisopropylethylamine, 1,8-diazabicycloundec-7-ene, 2,6-di-tert-butylpyridine, phosphazene bases, lithium diisopropylamide, silicon-based amides (e.g., potassium bis(trimethylsilyl)amide or sodium bis(trimethylsilyl)amide), lithium tetramethylpiperidide, sodium hydride, and potassium hydride.

"Acid" refers to a substance that tends to release a proton. The term "acid" contemplates all inorganic or organic acids. Acids include, but are not limited to, mineral acids, such as hydrogen halides and their solutions (hydrochloric acid (HCl), hydrobromic acid (HBr), hydroiodic acid (HI)), hypochloric acid (HClO), chloric acid (HClO$_3$), perchloric acid (HClO$_4$), hypobromous acid (HBrO), bromic acid (HBrO$_3$), perbromic acid (HBrO$_4$), hyopiodous acid (HIO), iodic acid (HIO$_3$), periodic acid (HIO$_4$), sulfuric acid (H$_2$SO$_4$), nitric acid (HNO$_3$), phosphoric acid (H$_3$PO$_4$), fluoroboric acid, sulfonic acids, such as methanesulfonic acid (or mesylic acid, CH$_3$SO$_3$H), ethanesulfonic acid (or esylic acid, CH$_3$CH$_2$SO$_3$H), benzenesulfonic acid (or besylic acid, C$_6$H$_5$SO$_3$H), p-toluenesulfonic acid (or tosylic acid, CH$_3$C$_6$H$_4$SO$_3$H), trifluoromethanesulfonic acid (or triflic acid, CF$_3$SO$_3$H), carboxylic acids, such as acetic acid, trifluoroacetic, citric acid, formic acid, gluconic acid, lactic acid, oxalic acid, tartaric acid, succinic acid, and malic acid.

"Silyl halide" refers to a structure represented by a formula $X^1SiA^1A^2A^3$ or $X^1X^2SiA^1A^2$ or $X^1X^2X^3SiA^1$ or $X^1X^2X^3X^4$ Si, wherein $X^1$, $X^2$, $X^3$, and $X^4$ are independently fluorine, chlorine, bromine, or iodine, and where $A^1$, $A^2$, and $A^3$ are independently hydrogen or a substituted or unsubstituted alkyl, cycloalkyl, alkoxy, alkenyl, cycloalkenyl, alkynyl, cycloalkynyl, aryl, or heteroaryl group as described herein.

"Pharmaceutical" or "pharmaceutically acceptable" when used herein as an adjective, means substantially non-toxic and substantially non-deleterious to the recipient.

By "pharmaceutical composition" it is further meant that the carrier, diluent, solvent, excipient, and salt must be compatible with the active ingredient of the formulation (e.g., a compound of the present application). It is understood by those of ordinary skill in this art that the terms "pharmaceutical formulation" and "pharmaceutical composition" are generally interchangeable, and they are so used for the purposes of this disclosure.

"Solution" refers to a clear, homogeneous liquid dosage form that contains one or more chemical substances dissolved in a solvent or mixture of mutually miscible solvents. Because molecules of a therapeutic agent substance in solution are uniformly dispersed, the use of solutions as dosage forms generally provides assurance of uniform dosage upon administration and good accuracy when the solution is diluted or otherwise mixed. "Solution" as disclosed herein contemplates any variations based on the current state of the art or variations achieved by one skilled in the art.

"Suspension" refers to a liquid dosage form that contains solid particles dispersed in a liquid vehicle. "Suspension" as disclosed herein contemplates any variations based on the current state of the art or variations achieved by one skilled in the art.

"Excipient" is used herein to include any other compound that is not a therapeutically or biologically active compound and may be contained in or combined with one or more of the compounds of the present disclosure. As such, an excipient should be pharmaceutically or biologically acceptable or relevant (for example, an excipient should generally be non-toxic to the subject). "Excipient" includes a single such compound and is also intended to include a plurality of excipients. For the purposes of the present disclosure the term "excipient" and "carrier" are used interchangeably throughout the description of the present application.

"Therapeutically effective amount" refers to that amount of a drug or pharmaceutical agent that will elicit the biological or medical response of a tissue, system, animal, or human that is being sought by a researcher or clinician.

"Treat," "treating," or "treatment" refers to decreasing the symptoms, markers, and/or any negative effects of a disease or condition in any appreciable degree in a subject who currently has the disease or condition. In some embodiments, treatment may be administered to a subject who exhibits only early signs of a disease or condition for the purpose of decreasing the risk of developing the disease or condition. In some embodiments, "Treat," "treating," or "treatment" refers to amelioration of one or more symptoms of a disease or condition. For example, amelioration of one or more symptoms of a disease or condition includes a decrease in the severity, frequency, and/or length of one or more symptoms of a disease or condition.

"Prevent," "prevention," or "preventing" refers to any method used to partially or completely prevent or delay the onset of one or more symptoms or features of a disease or condition. Prevention may be administered to a subject who does not exhibit any sign of a disease or condition.

"Subject" means a human or animal (in the case of an animal, more typically a mammal). In one aspect, the subject is a human.

The term "symptom" is defined as an indication of disease, illness, injury, or that something is not right in the body. Symptoms are felt or noticed by the individual experiencing the symptom, but may not easily be noticed by others. Others are defined as non-health-care professionals.

"αv integrin antagonist" refers to a compound which binds to and inhibits or interferes with the function of one or more of αvβ3, αvβ5, αvβ6, and αvβ8, a compound which binds to and inhibits or interferes with the function of both αvβ3 and αvβ5 (i.e., a dual αvβ3/αvβ5 antagonist), or a compound which binds to and inhibits or interferes with the function of both αvβ6 and αvβ8 (i.e., a dual αvβ6/αvβ8 antagonist). The compounds bind to the receptors as antagonists, blocking or interfering with the binding of the native agonist, such as vitronectin, while not provoking a biological response themselves.

The term "about" refers to a range of values which can be 15%, 10%, 8%, 5%, 3%, 2%, 1%, or 0.5% more or less than the specified value. For example, "about 10%" can be from 8.5% to 11.5%. In one embodiment, the term "about" refers to a range of values which are 5% more or less than the specified value. In another embodiment, the term "about" refers to a range of values which are 2% more or less than the specified value. In another embodiment, the term "about" refers to a range of values which are 1% more or less than the specified value.

EXAMPLES

Abbreviations used in the Following Examples and Elsewhere Herein are:
Ac$_2$O acetic anhydride
equiv equivalent(s)
DMAP 4-(dimethylamino)pyridine
TMSCl trimethylsilyl chloride
PPh$_3$ triphenylphosphine
KHMDS potassium bis(trimethylsilyl)amide
MeOH methanol
Et$_2$O diethyl ether
EtOAc ethyl acetate
hr hour(s)
wt weight
HPLC high-performance liquid chromatography
MeCN acetonitrile
n-BuLi n-butyl lithium
THF tetrahydrofuran
DEA Diethanolamine Example 1. Overall Synthetic Scheme for Intermediates and (S)-9-(5,6,7,8-tetrahydro-1,8-naphthyridin-2-yl)-3-(3-(trifluoromethyl)phenyl)nonanoic acid 2-amino-iso-butanol salt Synthesis of intermediate A:

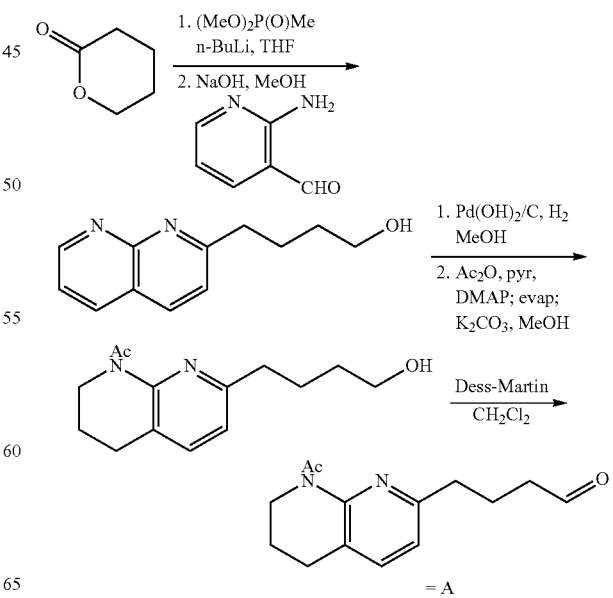

Synthesis of intermediate B:

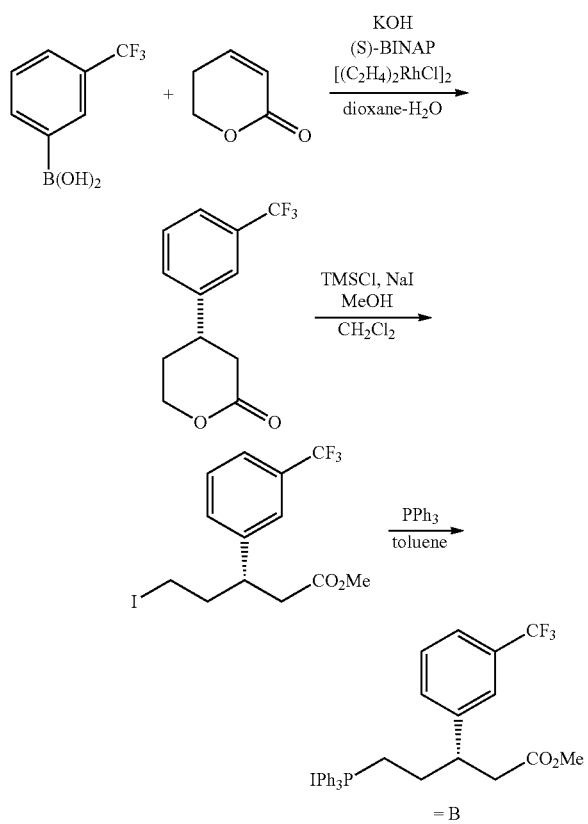

Coupling of A and B followed by the final step:

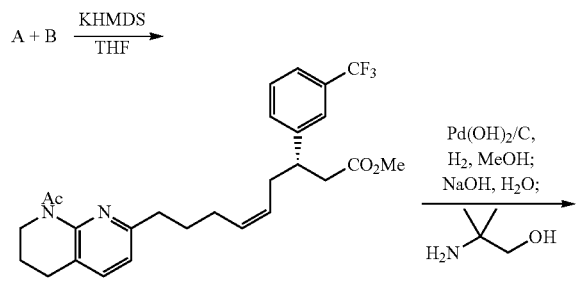

Example 2. Preparation of 4-(1,8-naphthyridin-2-yl)butan-1-ol

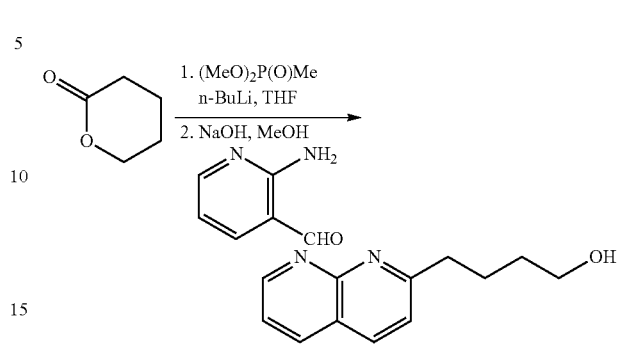

Under nitrogen, to dimethyl methylphosphonate (37.2 g, 300 mmol, 3.00 equiv) in THF (600 mL) at −78° C. was added n-BuLi (2.5 M, 120 mL, 300 mmol, 3.00 equiv) dropwise over 30 min. After stirring for 10 min at −78° C., δ-valerolactone (10.0 g, 100 mmol, 1.00 equiv) in THF (100 mL) was added dropwise over 30 min. After stirring for 10 min at −78° C., saturated NH$_4$Cl (aq) (500 mL) was added and the reaction mixture was warmed to 23° C. The phases were separated and the aqueous phase was extracted with EtOAc (2×500 mL). The combined organic phases were dried (MgSO$_4$) and the filtrate was concentrated in vacuo. The residue was azeotroped with toluene until the majority of unreacted dimethyl methylphosphonate was removed to afford crude β-ketophosphonate, which was used in the next step without further purification.

Under air, to the above-obtained β-ketophosphonate (<100 mmol, 1.00 equiv) in MeOH (130 mL) at 23° C. were added 2-amino-3-pyridinecarboxaldehyde (8.14 g, 66.7 mmol, 0.667 equiv) and 50% wt NaOH (aq) (5.34 g, 66.7 mmol, 0.667 equiv). After stirring for 1.5 hr at 50° C., the reaction mixture was concentrated in vacuo. Water (300 mL) was added to the residue, and the reaction mixture was extracted with CH$_2$Cl$_2$ (3×300 mL). The combined organic phases were dried (MgSO$_4$) and the filtrate was concentrated in vacuo. The residue was purified by column chromatography on silica gel eluting with hexanes/EtOAc to afford 12.0 g of the title compound (59% yield).

NMR Spectroscopy: $^1$H NMR (300 MH$_2$, CDCl$_3$, 23° C., δ): 9.07 (dd, J=3.9 Hz, 1.5 Hz, 1H), 8.16 (d, J=7.8 Hz, 1H), 8.10 (d, J=7.8 Hz, 1H), 7.47-7.36 (m, 2H), 3.70 (t, J=6.6 Hz, 2H), 3.10 (t, J=7.8 Hz, 2H), 2.08-1.94 (m, 2H), 1.77-1.64 (m, 2H).

Example 3. Preparation of 1-(7-(4-hydroxybutyl)-3,4-dihydro-1,8-naphthyridin-1(2H)-yl)ethanone

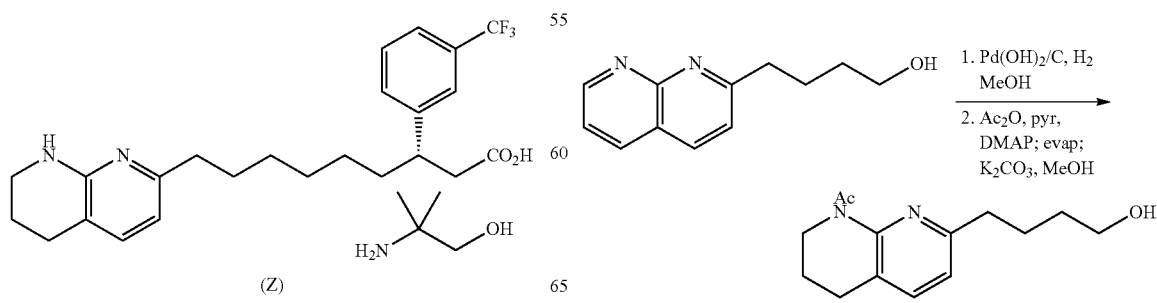

Under air, to 4-(1,8-naphthyridin-2-yl)butan-1-ol (12.0 g, 59.3 mmol, 1.00 equiv) in MeOH (300 mL) at 23° C. was added 20% Pd(OH)$_2$/C (4.17 g, 5.93 mmol, 0.100 equiv) and H$_2$ was introduced with a balloon. After stirring for 18 hr at 23° C., the reaction mixture was concentrated in vacuo to afford crude tetrahydronaphthyridine, which was used in the next step without further purification.

Under air, to the above-obtained tetrahydronaphthyridine (<59.3 mmol, 1.00 equiv) in pyridine-Ac$_2$O (59 mL-59 mL) at 23° C. was added 4-(dimethylamino)pyridine (362 mg, 2.97 mmol, 0.0500 equiv). After stirring for 1.5 hr at 50° C., the reaction mixture was concentrated in vacuo. The residue was dissolved in MeOH (300 mL) and potassium carbonate (24.6 g, 178 mmol, 3.00 equiv) was added at 23° C. After stirring for 40 min at 23° C., saturated NH$_4$Cl (aq) (200 mL) was added and the reaction mixture was concentrated in vacuo to remove MeOH. The aqueous solution was extracted with EtOAc (2×300 mL). The combined organic phases were dried (MgSO$_4$) and the filtrate was concentrated in vacuo. The residue was purified by column chromatography on silica gel eluting with hexanes/EtOAc to afford 10.1 g of the title compound (69% yield).

NMR Spectroscopy: $^1$H NMR (300 MH$_2$, CDCl$_3$, 23° C., δ): 7.34 (d, J=7.5 Hz, 1H), 6.85 (d, J=7.5 Hz, 1H), 3.88 (t, J=6.0 Hz, 2H), 3.67 (t, J=6.6 Hz, 2H), 2.80-2.69 (m, 4H), 2.48 (s, 3H), 1.99-1.57 (m, 6H).

Example 4. Preparation of 4-(8-acetyl-5,6,7,8-tetrahydro-1,8-naphthyridin-2-yl)butanal

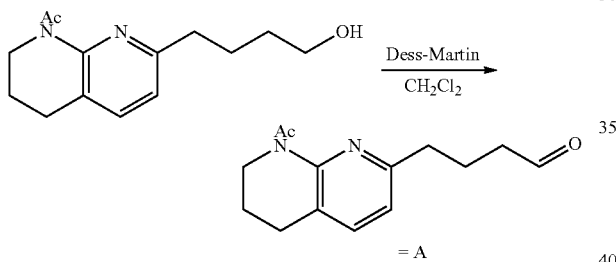

Under nitrogen, to 1-(7-(4-hydroxybutyl)-3,4-dihydro-1,8-naphthyridin-1(2H)-yl)ethanone (13.7 g, 55.0 mmol, 1.00 equiv) in CH$_2$Cl$_2$ (220 mL) at 0° C. was added Dess-Martin periodinane (28.0 g, 66.0 mmol, 1.20 equiv). After stirring for 2 hr at 23° C., 0.5M NaOH (aq) (400 mL) was added and the reaction mixture was extracted with CH$_2$Cl$_2$ (2×300 mL). The combined organic phases were dried (MgSO$_4$) and the filtrate was concentrated in vacuo to afford 12.8 g of the title compound (94% yield).

NMR Spectroscopy: $^1$H NMR (300 MH$_2$, CDCl$_3$, 23° C., δ): 9.77 (s, 1H), 7.34 (d, J=7.5 Hz, 1H), 6.84 (d, J=7.5 Hz, 1H), 3.88 (t, J=6.0 Hz, 2H), 2.79-2.70 (m, 4H), 2.54-2.43 (m, 5H), 2.10-1.89 (m, 4H).

Example 5. Preparation of (S)-4-(3-(trifluoromethyl)phenyl)tetrahydro-2H-pyran-2-one

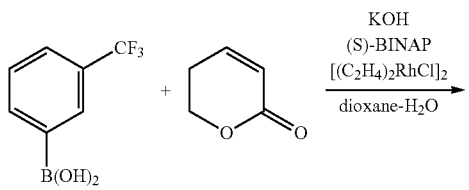

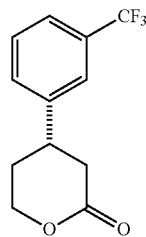

Under air, to 5,6-dihydro-2H-pyran-2-one (90% pure, 10.0 g, 91.7 mmol, 1.00 equiv) at 23° C. in dioxane-water (100 mL-10 mL) were added 3-(trifluoromethyl)phenylboronic acid (26.1 g, 138 mmol, 1.50 equiv), potassium hydroxide (5.15 g, 91.7 mmol, 1.00 equiv), (S)-BINAP (2.28 g, 3.67 mmol, 4.00 mol %), and di-µ-chlorotetraethylene dirhodium(I) (714 mg, 1.83 mmol, 2.00 mol %). After stirring for 30 min at 80° C., the reaction mixture was cooled to 23° C. and diluted brine (200 mL) was added. The phases were separated and the aqueous phase was extracted with Et2O (2×300 mL). The combined organic phases were washed with brine (100 mL) and dried (MgSO$_4$). The filtrate was concentrated in vacuo and the residue was purified by column chromatography on silica gel eluting with hexanes/EtOAc to afford 15.6 g of the title compound (70% yield).

NMR Spectroscopy: $^1$H NMR (300 MH$_2$, CDCl$_3$, 23° C., δ): 7.59-7.37 (m, 4H), 4.59-4.50 (m, 1H), 4.48-4.38 (m, 1H), 3.40-3.26 (m, 1H), 3.02-2.91 (m, 1H), 2.70-2.58 (m, 1H), 2.28-2.00 (m, 2H). $^{19}$F NMR (282 MH$_2$, CDCl$_3$, 23° C., δ): −62.5 (s, 3F).

Example 6. Preparation of (R)-methyl 5-iodo-3-(3-(trifluoromethyl)phenyl)pentanoate

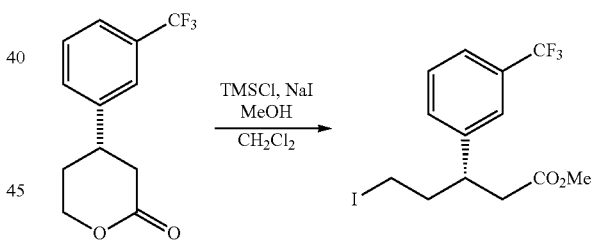

Under nitrogen, to (S)-4-(3-(trifluoromethyl)phenyl)tetrahydro-2H-pyran-2-one (13.0 g, 53.2 mmol, 1.00 equiv) and NaI (20.0 g, 133 mmol, 2.50 equiv) at 0° C. in CH$_2$Cl$_2$ (220 mL) was added TMSC1 (16.9 mL, 133 mmol, 2.50 equiv). After stirring for 10 min at 0° C., MeOH (6.46 mL, 160 mmol, 3.00 equiv) was added and the reaction mixture was warmed to 23° C. After stirring for 50 min at 23° C., saturated Na$_2$S$_2$O$_3$ (aq) (300 mL) was added. The phases were separated and the aqueous phase was extracted with CH$_2$Cl$_2$ (2×300 mL). The combined organic phases were washed with brine (100 mL) and dried (MgSO$_4$). The filtrate was concentrated in vacuo and the residue was purified by column chromatography on silica gel eluting with hexanes/EtOAc to afford 14.9 g of the title compound (72% yield).

NMR Spectroscopy: $^1$H NMR (300 MH$_2$, CDCl$_3$, 23° C., δ): 7.55-7.40 (m, 4H), 3.60 (s, 3H), 3.42-3.35 (m, 1H), 3.10-3.00 (m, 1H), 2.86-2.78 (m, 1H), 2.69-2.62 (m, 2H), 2.29-2.10 (m, 2H). $^{19}$F NMR (282 MH$_2$, CDCl$_3$, 23° C., δ): −62.5 (s, 3F).

Example 7. Preparation of (R)-(5-methoxy-5-oxo-3-(3-(trifluoromethyl)phenyl)pentyl) triphenylphosphonium iodide

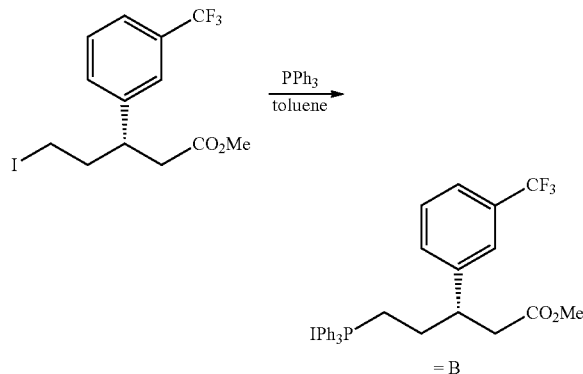

Under nitrogen, to (R)-methyl 5-iodo-3-(3-(trifluoromethyl)phenyl)pentanoate (14.9 g, 38.6 mmol, 1.00 equiv) in toluene (39 mL) at 23° C. was added triphenylphosphine (20.2 g, 77.2 mmol, 2.00 equiv). After stirring for 7 hr at 100° C., the reaction mixture was cooled to 23° C. and was concentrated in vacuo. The residue was purified by column chromatography on silica gel eluting with $CH_2Cl_2$/MeOH to afford 23.6 g of the title compound (94% yield).

NMR Spectroscopy: $^1H$ NMR (300 $MH_2$, $CDCl_3$, 23° C., δ): 7.82-7.40 (m, 19H), 4.38-4.20 (m, 1H), 3.72-3.61 (m, 1H), 3.52 (s, 3H), 3.06-2.68 (m, 3H), 2.34-2.20 (m, 1H), 2.04-1.90 (m, 1H). $^{19}F$ NMR (282 $MH_2$, $CDCl_3$, 23° C., δ): −62.5 (s, 3F).

Example 8. Preparation of (S,Z)-methyl 9-(8-acetyl-5,6,7,8-tetrahydro-1,8-naphthyridin-2-yl)-3-(3-(trifluoromethyl)phenyl)non-5-enoate

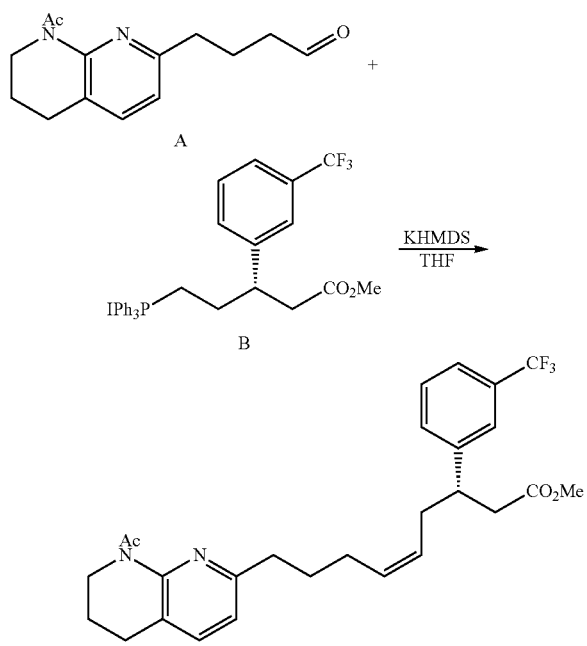

Under nitrogen, to (R)-(5-methoxy-5-oxo-3-(3-(trifluoromethyl)phenyl)pentyl) triphenylphosphonium iodide (211 mg, 0.325 mmol, 1.00 equiv) in THF (0.5 mL) at −78° C. was added KHMDS (1.0 M, 325 μL, 0.325 mmol, 1.00 equiv) dropwise over 5 min. After stirring for 15 min at −78° C., 4-(8-acetyl-5,6,7,8-tetrahydro-1,8-naphthyridin-2-yl)butanal in THF (0.5 mL) was added dropwise over 5 min. After stirring for 15 min at −78° C., the reaction mixture was warmed to 23° C. After stirring for 10 min at 23° C., water (2 mL) was added and the reaction mixture was extracted with EtOAc (3×2 mL). The combined organic phases were dried ($MgSO_4$) and the filtrate was concentrated in vacuo. The residue was purified by column chromatography on silica gel eluting with hexanes/EtOAc to afford 100 mg of the title compound (63% yield).

NMR Spectroscopy: $^1H$ NMR (300 $MH_2$, $CDCl_3$, 23° C., δ): 7.49-7.30 (m, 5H), 6.80 (d, J=7.2 Hz, 1H), 5.48-5.19 (m, 2H), 3.88 (t, J=6.0 Hz, 2H), 3.57 (s, 3H), 3.30-3.18 (m, 1H), 2.78-2.50 (m, 6H), 2.47 (s, 3H), 2.41-2.25 (m, 2H), 2.00-1.86 (m, 4H), 1.76-1.60 (m, 2H). $^{19}F$ NMR (282 $MH_2$, $CDCl_3$, 23° C., δ): −62.5 (s, 3F).

Example 9. Preparation of (S)-9-(5,6,7,8-tetrahydro-1,8-naphthyridin-2-yl)-3-(3-(trifluoromethyl)phenyl) nonanoic acid 2-amino-iso-butanol salt

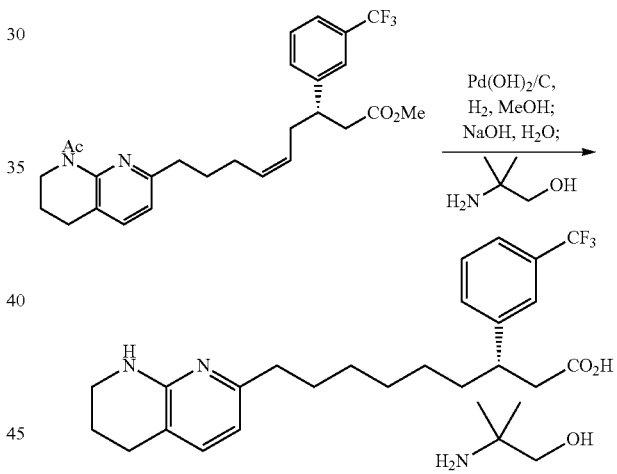

Under air, to (S,Z)-methyl 9-(8-acetyl-5,6,7,8-tetrahydro-1,8-naphthyridin-2-yl)-3-(3-(trifluoromethyl)phenyl)non-5-enoate (6.10 g, 12.5 mmol, 1.00 equiv) in MeOH (125 mL) at 23° C. was added 20% $Pd(OH)_2$/C (877 mg, 1.25 mmol, 0.100 equiv) and $H_2$ was introduced with a balloon. After stirring for 12 hr at 23° C., 15% wt NaOH (aq) (33.3 mL, 125 mmol, 10.0 equiv) was added. After stirring for 3 hr at 65° C., the reaction mixture was cooled to 23° C. and 1N HCl (aq) was added till the pH becomes ~5. The reaction mixture was filtered through a pad of celite. The filtrate was concentrated in vacuo to remove MeOH. The aqueous solution was extracted with EtOAc (3×200 mL). The combined organic phases were dried ($MgSO_4$) and the filtrate was concentrated in vacuo. The residue was filtered through a pad of silica gel and the filtrate was concentrated in vacuo. The residue was dissolved in MeCN (20 mL) and 2-amino-iso-butanol (1.19 mL, 12.5 mmol, 1.00 equiv) was added.

The reaction mixture was heated to 80° C. to make a homogeneous solution, which was slowly cooled to −20° C. and kept at −20° C. for 24 hr. The formed crystals were filtered off and washed with cold MeCN to afford 6.10 g of the title compound (93% yield). The enantiomeric excess was determined to be 99.8% ee using the chiral chromatography conditions shown below.

NMR Spectroscopy: $^1$H NMR (300 MH$_2$, CD$_3$OD, 23° C., δ): 7.50-7.40 (m, 4H), 7.11 (d, J=7.2 Hz, 1H), 6.30 (d, J=7.2 Hz, 1H), 3.43 (s, 2H), 3.40-3.32 (m, 2H), 3.21-3.10 (m, 1H), 2.70-2.61 (m, 2H), 2.50-2.38 (m, 4H), 1.90-1.20 (m, 18H). $^{19}$F NMR (282 MH$_2$, CD$_3$OD, 23° C., δ): −62.4 (s, 3F).

EQUIVALENTS

Those skilled in the art will recognize, or be able to ascertain, using no more than routine experimentation, numerous equivalents to the specific embodiments described specifically herein. Such equivalents are intended to be encompassed in the scope of the present application.

The invention claimed is:

1. A method of making a compound of formula I:

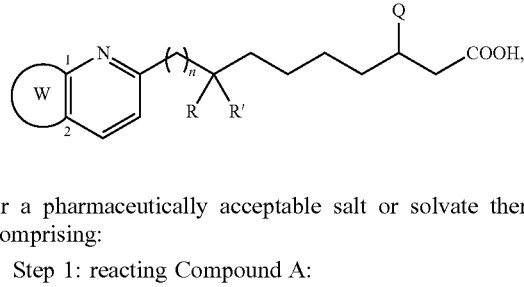

or a pharmaceutically acceptable salt or solvate thereof, comprising:

Step 1: reacting Compound A:

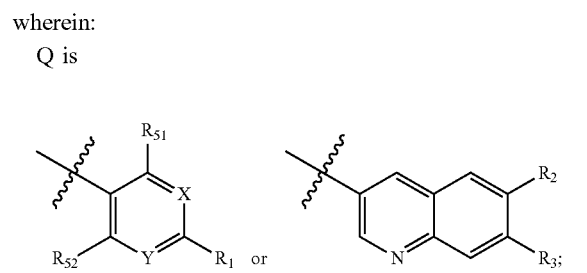

wherein "Ac" refers to an acetyl group and is a substituent on W, with Compound B:

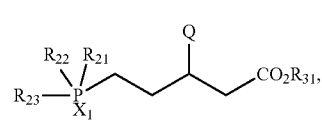

wherein $X_1$ is halogen, and $R_{21}$, $R_{22}$, $R_{23}$, and $R_{31}$ are each independently selected from the group consisting of optionally substituted alkyl, optionally substituted alkenyl, optionally substituted alkynyl, and optionally substituted aryl, to form Compound 1:

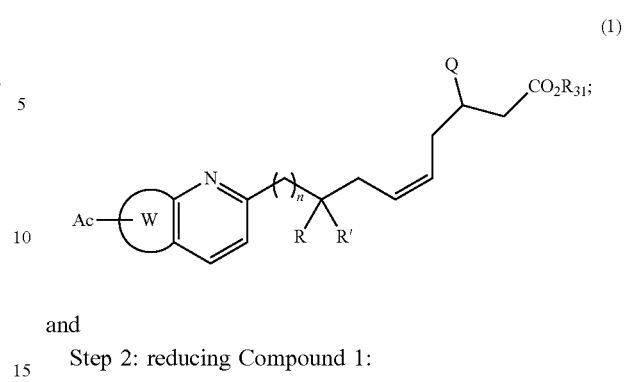

and

Step 2: reducing Compound 1:

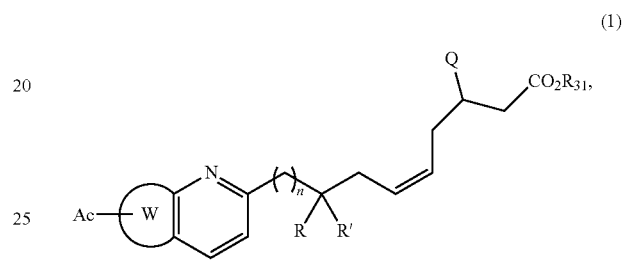

optionally in the presence of a catalyst, to form the compound of formula I:

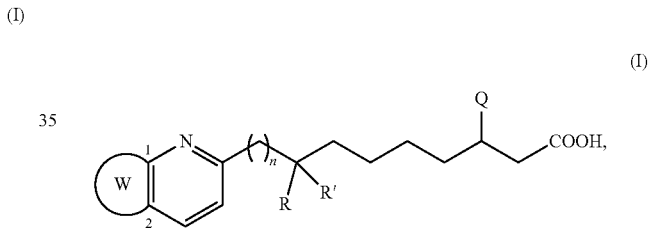

wherein:

Q is

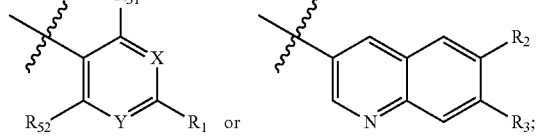

X is CR$_4$ or N;

Y is CR$_4$ or N;

R$_1$ is H, F, Cl, C$_1$-C$_4$ alkyl substituted with 1, 2, 3, 4, 5, 6, 7, 8, or 9 fluorine atoms, or C$_1$-C$_4$ alkoxy substituted with 0, 1, 2, 3, 4, 5, 6, or 7 fluorine atoms;

R$_2$ and R$_3$ are each independently H, F, CH$_2$F, CHF$_2$, or CF$_3$, provided that one of R$_2$ and R$_3$ is not H;

each R$_4$ is independently H, CH$_2$F, CHF$_2$, or CF$_3$; and

R$_{51}$ and R$_{52}$ are each independently H, F, or C$_1$;

W is fused to the pyridyl moiety at positions 1 and 2, and W is a 5- to 7-membered ring optionally comprising 1-4 heteroatoms selected from the group consisting of N, O, and S;

n is 1 or 2; and

R and R' are each independently H or F, or R and R', together with the carbon atom to which they are attached, form a 3- or 4-membered carbocyclic or heterocyclic ring.

2. The method of claim 1, wherein n is 1.

3. The method of claim 1, wherein R and R' are each H.

4. The method of claim 1, wherein Q is $$\text{(structure with } R_{51}, R_{52}, X, Y, R_1\text{)}$$

5. The method of claim 1, wherein $R_{51}$ and $R_{52}$ are each H.

6. The method of claim 1, wherein X is N and Y is $CR_4$.

7. The method of claim 1, wherein at least one $R_4$ is $CF_3$.

8. The method of claim 1, wherein $R_1$ is H.

9. The method of claim 1, wherein Q is $$\text{(quinoline structure with } R_2, R_3\text{)}$$

10. The method of claim 1, wherein $$\text{(ring structure with W, N)}$$

is selected from the group consisting of $$\text{(four bicyclic structures)}$$

11. The method of claim 1, further comprising one or more steps selected from:

Step A1: reacting Compound 2:

(2)

$$\text{(lactone structure with R, R', n)}$$

with Compound 3:

(3)

$$\text{(W' ring with } NH_2 \text{ and CHO)}$$

wherein W' is an unsaturated, partially saturated, or aromatic 5- to 7-membered ring optionally comprising 1-4 heteroatoms selected from the group consisting of N, O, and S, to form Compound 4:

(4)

$$\text{(structure with W', N, n, R, R', OH)}$$

Step A2: reducing Compound 4:

(4)

$$\text{(structure with W', N, n, R, R', OH)}$$

optionally in the presence of a catalyst, followed by a reaction with acetic anhydride to form Compound 5:

(5)

$$\text{(structure with Ac-W, N, n, R, R', OH)}$$

and

Step A3: converting Compound 5:

(5)

$$\text{(structure with Ac-W, N, n, R, R', OH)}$$

to Compound A:

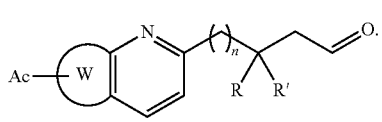

(A)

12. The method of claim 1, further comprising one or more steps selected from:

Step B1: reacting Compound 6a:

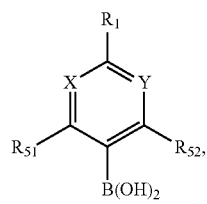

(6a)

with Compound 7:

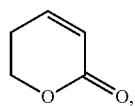

(7)

to form Compound 8a:

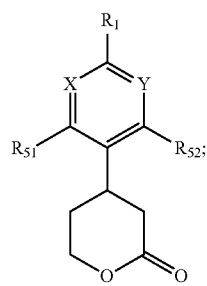

(8a)

Step B2: converting Compound 8a:

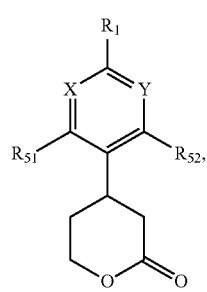

(8a)

to Compound 9a:

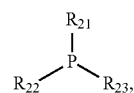

(9a)

wherein $X_1$ is halogen; and

Step B3: reacting Compound 9a:

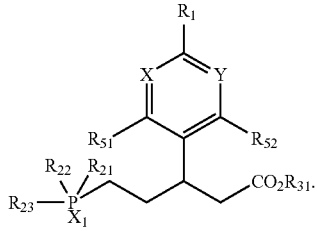

(9a)

with a phosphine compound $$R_{22} - P(R_{21})(R_{23})$$

to form Compound B1:

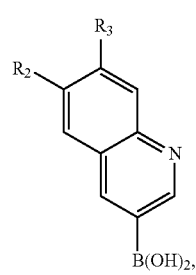

(B1)

13. The method of claim 1, further comprising one or more steps selected from:

Step C1: reacting Compound 6b:

(6b)

with Compound 7:

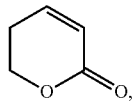

to form Compound 8b:

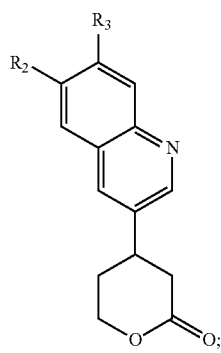

Step C$_2$: converting Compound 8b:

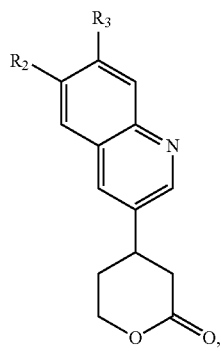

to Compound 9b:

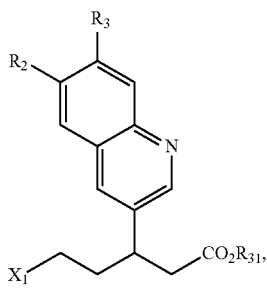

wherein X$_1$ is halogen;

Step C$_3$: reacting Compound 9b:

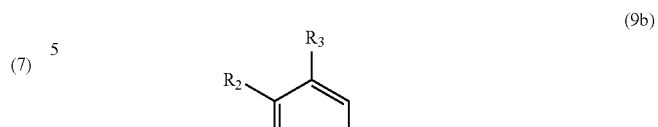

with a phosphine compound

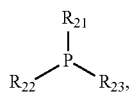

to form Compound B2:

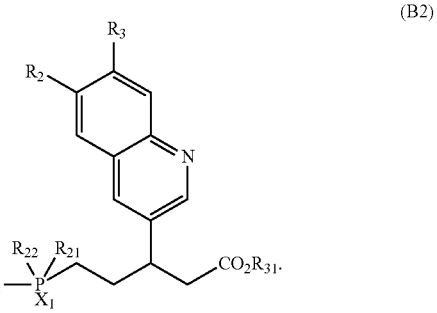

14. The method of claim 1, wherein Step 1 comprises:
 1a. adding a non-nucleophilic base to Compound B to generate a mixture; and
 1b. adding Compound A to the mixture from Step 1a.

15. The method of claim 1, wherein Step 2 comprises:
 2a. adding H$_2$ to Compound 1 in the presence of a protic solvent;
 2b. adding a base to the reaction mixture from Step 2a; and
 2c. adding an acid to the reaction mixture from Step 2b.

16. The method of claim 11, wherein:
 Step A1 comprises:
  A1a. adding n-butyllithium to dimethyl methylphosphonate;
  A1b. adding Compound 2 to the mixture from Step A1a; and
  A1c. adding Compound 3 to the mixture from Step A1b;
 Step A2 comprises:
  A2a. adding H$_2$ to Compound 4 in the presence of a protic solvent; and
  A2b. adding 4-(dimethylamino)pyridine to the reaction mixture from Step A2a; and
 Step A3 comprises:
  adding Dess-Martin periodinane to Compound 5.

17. The method of claim 12, wherein:
 Step B1 comprises:
  adding Compound 6a, a chiral ligand, and a metal catalyst to Compound 7; and Step B2 comprises:
- B2a. adding a metal halide and silyl halide to Compound 8a to generate a mixture; and
- B2b. adding a protic solvent to the mixture from Step B2a.

18. The method of claim 13, wherein:

Step C1 comprises:
- adding Compound 6b, a chiral ligand, and a metal catalyst to Compound 7; and Step $C_2$ comprises:
- C2a. adding a metal halide and silyl halide to Compound 8b; and
- C2b. adding a protic solvent to the mixture from Step C2a.

\* \* \* \* \*

UNITED STATES PATENT AND TRADEMARK OFFICE
CERTIFICATE OF CORRECTION

PATENT NO. : 10,752,625 B2
APPLICATION NO. : 16/288309
DATED : August 25, 2020
INVENTOR(S) : Takeru Furuya Page 1 of 1

It is certified that error appears in the above-identified patent and that said Letters Patent is hereby corrected as shown below:

In the Claims

At Column 76, Claim number 1, Line number 63:
$R_{51}$ and $R_{52}$ are each independently H, F, or $C_1$;
Should read:
$R_{51}$ and $R_{52}$ are each independently H, F, or Cl;

At Column 81, Claim number 13, Line number 33:
Step $C_2$: converting Compound 8b:
Should read:
Step C2: converting Compound 8b:

At Column 82, Claim number 13, Line number 1:
Step $C_3$: reacting Compound 9b:
Should read:
Step C3: reacting Compound 9b:

At Column 83, Claim number 18, Line number 10:
Step $C_2$ comprises:
Should read:
Step C2 comprises:

Signed and Sealed this
Fifteenth Day of December, 2020

Andrei Iancu
*Director of the United States Patent and Trademark Office*